(12) United States Patent
Liu et al.

(10) Patent No.: US 9,751,882 B2
(45) Date of Patent: Sep. 5, 2017

(54) DIARYL[A, G]QUINOLIZIDINE COMPOUND, PREPARATION METHOD THEREFOR, PHARMACEUTICAL COMPOSITION, AND USES THEREOF

(71) Applicant: SHANGHAI INSTITUTE OF MATERIA MEDICA, CHINESE ACADEMY OF SCIENCES, Pudong, Shanghai (CN)

(72) Inventors: Hong Liu, Shanghai (CN); Xuechu Zhen, Shanghai (CN); Haifeng Sun, Shanghai (CN); Liyuan Zhu, Shanghai (CN); Wangke Qian, Shanghai (CN); Leiping Yu, Shanghai (CN); Zeng Li, Shanghai (CN); Shengbin Zhou, Shanghai (CN); Wenxian Cai, Shanghai (CN); Hualiang Jiang, Shanghai (CN); Kaixian Chen, Shanghai (CN)

(73) Assignee: Kingsound & Partner, Beijing (CN)

( * ) Notice: Subject to any disclaimer, the term of this patent is extended or adjusted under 35 U.S.C. 154(b) by 0 days.

(21) Appl. No.: 14/400,203

(22) PCT Filed: May 9, 2013

(86) PCT No.: PCT/CN2013/000549
§ 371 (c)(1),
(2) Date: Nov. 10, 2014

(87) PCT Pub. No.: WO2013/166862
PCT Pub. Date: Nov. 14, 2013

(65) Prior Publication Data
US 2015/0141419 A1 May 21, 2015

(30) Foreign Application Priority Data
May 9, 2012 (CN) .......................... 2012 1 0142903

(51) Int. Cl.
| | | |
|---|---|---|
| *C07D 471/14* | (2006.01) | |
| *C07D 495/14* | (2006.01) | |
| *C07D 491/22* | (2006.01) | |
| *C07D 491/147* | (2006.01) | |
| *C07D 495/22* | (2006.01) | |
| *C07D 455/03* | (2006.01) | |

(52) U.S. Cl.
CPC ......... *C07D 471/14* (2013.01); *C07D 455/03* (2013.01); *C07D 491/147* (2013.01); *C07D 491/22* (2013.01); *C07D 495/14* (2013.01); *C07D 495/22* (2013.01)

(58) Field of Classification Search
None
See application file for complete search history.

(56) References Cited

FOREIGN PATENT DOCUMENTS

| CN | 1603324 | 4/2005 |
|---|---|---|
| CN | 1900076 | 1/2007 |
| EP | 0524004 | 1/1993 |
| JP | 50-24299 | 3/1975 |
| WO | 2008014661 | 2/2008 |
| WO | 2010/075469 | 7/2010 |

OTHER PUBLICATIONS

Bremner et al., 41(4) Australian J. of Chem. 575-83 (1988) (CAS Abstract).*
Bremner et al., 41(1) Australian J. of Chem. 111-26 (1988) (CAS Abstract).*
Elderfield, 19 J.O.C. 683-92 (1954) (CAS Abstract).*
Hahn & Hansel, 71B Berichte Der Deutschen Chemischen Gesellschaft [Abteilung] B: Abhandlungen 2192-7 (1938) (CAS Abstract).*
Pakrashi et al, 21(27) Tetrahedron Letts., 2667-70 (1980) (CAS Abstract).*
Onda et al, 76 Yakugaku Zasshi, 966-8 (1959) (CAS Abstract).*
Logemann et al., 88 Chemische Berichte, 1952-6 (1955) (CAS Abstract).*
Spangler, et al., "A new synthesis of benzocyclobutenes. Thermal and electron impact induced decomposition of 3-isochromanones", J. Org. Chem., vol. 42, No. 18, pp. 2989-2996, (1977).
Cushman, et al., "Synthesis of (±)-thalictricavine, berlambine, and (±)-canadine from a common intermediate", J. Org. Chem., vol. 44, No. 3, pp. 407-409, (1979).
Swan, et al., "The constitution of yohimbine and related alkaloids. Part IV. A synthesis of yohimbone", J. Chem. Soc., pp. 1534-1539, (1950).
Bremner, et al., "Derivatives of the Benzo[5,6]cyclohepta[1,2,3-Cd]thieno[3,2-C]pyridine System. X-Ray Crystal Structure of 8,9-Dimethoxy-1,2,3,6,11,11a-hexahydrobenzo[5,6]cyclohepta[1,2,3-Cd]thieno[3,2-C]pyridine-1-carbonitrile", vol. 41, No. 4, pp. 575-583 (1988).

(Continued)

*Primary Examiner* — Timothy R Rozof
(74) *Attorney, Agent, or Firm* — Ping Wang; Andrews Kurth Kenyon LLP

(57) ABSTRACT

The present invention relates to a diarylo[a,g]quinolizidine compound of formula (I), enantiomer, diastereoisomer, racemate, mixture, pharmaceutically acceptable salt, crystalline hydrate or solvate thereof; the preparation method thereof, and uses thereof in preparing an experimental model drugs related to dopamine receptors and 5-HT receptors or a medicament for treating or preventing a disease related to dopamine receptors and 5-HT receptors.

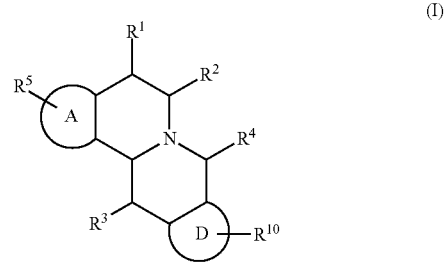

5 Claims, No Drawings

(56) References Cited

OTHER PUBLICATIONS

International Search Report of international application No. PCT/CN2013/000549 mailed Aug. 15, 2013.
Supplementary European Search Report of Application No. 13787305.5 mailed Jan. 22, 2015.
Bremner, J. B. et al., "Synthesis of Some Thieno Analogs of the Protoberberine and Protopine Skeletons. X-Ray Crystal Structure of 9,10-Dimethoxy-5-methyl-4,5,6,7,12,13-hexahydrothieno[3,2-e][3]benzazeci n-12-one", Australian Journal of Chemistry, 1988, vol. 41, Issue 1, pp. 111-126.
Potts, K. T. et al., "Synthesis of γ-carbolines", Chemical Communications, 1966, pp. 857-858.
Knölker, H. J. et al., "Transition metal complexes in organic synthesis. Part 62:1 Total synthesis of (±)-demethoxycarbonyldihydrogambirtannine and norketoyobyrine by an iron-mediated [2+2+1] cycloaddition", Tetrahedron Letters, 2000, vol. 41, Issue 26, pp. 5035-5038.
Diker, K. et al., "Trapping of iminiums by the indole nucleus during catalytic hydrogenation of nitriles: a rapid synthesis of tetrahydro-β-carbolines", Tetrahedron Letters, 1995, vol. 36, Issue 14, pp. 2497-2500.
Short, J. H. et al., "New Synthesis of 18-Hydroxy-17-methoxy-15,16,17,18,19,20-hexadehydroyohimbane Hydrochloride", Journal of Organic Chemistry., 1961, vol. 26, Issue 7, pp. 2560-2561.
Koepler, O. et al., "Synthesis and DNA binding properties of novel benzo[b]isoquino[2,3-h]-naphthyridines", Organic & Biomolecular Chemistry, 2005, vol. 3, pp. 2848-2858.
Pandit, U. K. et al., "Synthetic entry into yohimbinoid alkaloids and novel synthesis of (±)-17-methoxy-hexadehydroyohimbane", Tetrahedron, 1987, vol. 43, Issue 18, pp. 4235-4239.
Weise, K. et al., "Aufbau eines Yohimban-ähnlichen Heterocyclus" Tetrahedron Letters, 1971, vol. 12, Issue 17, pp. 1231-1232.
Clark, R. D. et al., "Stereospecific Synthesis of the (3aα, 11α, 12aα)-Decahydrobenzo[a]pyrrolo[3,2-g]quinolizine Ring System", Journal of Heterocyclic Chemistry, 1993, vol. 30, Issue 3, pp. 829-831.
Morrison, G. C. et al., "1,4,4a,5,6,8,9,14,14a,14b-Decahydrobenz[a]indolo[2,3-g]quinolizinones. A System Isomeric with Yohimbane", Journal of Heterocyclic Chemistry, 1971, vol. 8, Issue 6, pp. 1025-1026.
Jeganathan, S. et al., "Studies on Heterocyclic Compounds; I. Synthesis of Thiophene Derivatives of Protoberberine Alkaloids", Synthesis, 1979, pp. 195-196.
Lenz, G. R., "The Synthesis of 8-Oxoberbines Containing a Heterocyclic D-Ring by Enamide Photocyclizations", Journal of Heterocyclic Chemistry, 1979, vol. 16, Issue 3, pp. 433-437.
Boekelheide, B. et al., "The Synthesis of 1,2-Benzo-7,8-(2',3'-indolo)-tetrahydroquinolizine", Journal of the American Chemical Society, 1952, vol. 74, Issue 19, pp. 4920-4923.
Ito, C. et al., "Chemopreventive activity of isoquinoline alkaloids from Corydalis plants", Planta Med, 2001, vol. 67, Issue 5, pp. 473-475.
Wu, Y. R. et al., "Two new quaternary alkaloids and anti-hepatitis B virus active constituents from Corydalis saxicola", Planta Med, 2007, vol. 73, Issue 8, pp. 787-791.
Nogradi, T., "Untersuchungen über Rauwolfia-Alkaloid-Modelle II* 2-Substituierte Indole, Tetrahydrocarbolin- und Hexadehydroyohimban-Derivate", Monatshefte für Chemie und verwandte Teile anderer Wissenschaften, 1957, vol. 88, Issue 6, pp. 1087-1094.
Schaper, K. J., "Free-Wilson-Type Analysis of Non-Additive Substituent Effects on THPB Dopamine Receptor Affinity Using Artificial Neural Networks", Quantitative Structure-Activity Relationships, vol. 18, Issue 4, pp. 354-360. Abstract.
Jeganathan, S. et al., "Studies on Heterocyclic Compounds VI: Synthesis of Thiophene Isosters of Protoberberine Alkaloids1", Phosphorus and Sulfur and the Related Elements, 1981, vol. 11, Issue 2, pp. 125-137.

* cited by examiner

DIARYL[A, G]QUINOLIZIDINE COMPOUND, PREPARATION METHOD THEREFOR, PHARMACEUTICAL COMPOSITION, AND USES THEREOF

FIELD OF THE INVENTION

The present invention relates to the field of pharmaceutical chemistry and chemotherapy. Specifically, the present invention relates to a class of diarylo[a,g]quinolizines of formula (I) and derivatives thereof with a novel structure, a process for preparing the same, a pharmaceutical composition thereof; and a use thereof in preparing a medicament for treating a neurological disease, especially, Parkinson's disease, schizophrenia, mania, depression, drug addiction, migraine and the like, which involves in a dopamine receptor and a 5-HT receptor.

BACKGROUND

Neurological disease has been one of the prevalent diseases in contemporary society. However, many types of neurological disease have not yet been effectively addressed in clinical practice. Especially, the treatments for neurological diseases such as schizophrenia, Parkinson's disease and the like are still far from achieving a satisfactory result.

Schizophrenia is one of the most serious mental disorders, and has an incidence of up to 1% in a general population. Its clinical manifestation may be classified into positive symptoms represented by hallucination, delusion, exhilaration, bizarre behavior, etc., and negative symptoms represented by quiet, poverty of thought, abepithymia, abulia, degeneration of sociability etc. According to incomplete statistics, China has no less than 10 million of patients with schizophrenia. As the pace of life is quickened and the pressure of work is increased, schizophrenia tends to have an increasing incidence, and will cause heavy economic burden and social burden.

The recognition of the mechanism of schizophrenia was firstly originated from the use of chlorpromazine about half a century ago. In the practice of treating schizophrenia, blocking dopamine (DA) D2 receptor in brain is deemed as the main direction of drug research against schizophrenia. Based on such recognition, the pathological DA theory of schizophrenia was established. The first-generation drugs against schizophrenia, as DA antagonists, have relatively serious side effect to extrapyramidal system and hyperprolactinemia due to its lacking of selectivity to DA receptor. With progression in cognition about the pathology of schizophrenia and research on cloning of the subtypes of DA receptor and difference in their pharmacologic characteristics, the second-generation antipsychotic drugs, which are also referred as nonclassical antipsychotic drugs, were developed. The representative examples of these drugs include Clozapine, Risperidone and so on, which share the similar characteristics of having an increased selectivity to D2 acceptor antagonistic action and a weaker side effect than the first-generation antipsychotic drugs. These drugs can effectively improve the patients' positive symptoms including delusion, hallucination and so on, but still have weak activity on treating the negative symptoms of schizophrenia. Thus, there is a urgent need to design and develop new antipsychotic drugs.

The normal function of brain depends on appropriate amount of DA and its normal activity. It has been known that overactivity, especially the hyperfunction, of DA receptor, is related to the positive symptoms of schizophrenia, such as delusion, hallucination and the like, and abnormal activity of nigrostriatal DA is related to extrapyramidal symptoms. The occurrence of the negative symptoms of schizophrenia and damage to cognitive function are related to DA activity, especially impairment of D1/NMDA receptors, in prefrontal cortex (mPFC), wherein hypofrontality of D1 in mPFC may be the key point. Due to hypofrontality of DA in this area, the inhibitory effect to nucleus accumbens (NAc) and ventral tegmental area (VTA) is reduced, and thus hyperfunction of DA in subcortex region is incurred, resulting in the positive symptoms of schizophrenia. Meanwhile, impairment to D1/NMDA receptors, including 5-HT receptor, in mPFC is closely related to negative symptoms and cognitive function. It has been proved that there is an interadjusting between D1 and NMDA receptor. Thus, disorder and imbalance of DA functional activities in certain encephalic region, i.e., hypofrontality of D1/NMDA in mPFC area, and hyperfunction of D2 in subcortical structures are considered as the current pathomechanism of schizophrenia. Therefore, rebuilding and recovering the balance of DA activity in brain naturally becomes a new therapeutic strategy of schizophrenia. Accordingly, it is an ideal orientation for the study on antischizophrenic drugs to research and develop drugs capable of recovering and stabilizing the normal activity of DA. Meanwhile, by caning out working memory experiments for animals and patients, short-term experiments reflecting the function of medical prefrontal cortex, as well as clinical trials, it has been demonstrated that the inactivation of D1 receptor is related to negative symptoms of schizophrenia, and high activity of D2 receptor generates the positive symptoms. Based on such hypothesis, if a drug can effectively activate the activity of D1 receptor and antagonize the activity of D2 receptor at the same time, such a drug will have a good prospect for the treatment of schizophrenia. However, the currently known antipsychotic drugs are mainly based on antagonism against D2 receptor, and thus have poor therapeutic effect on negative symptoms. In particular, such drugs cannot function to stabilize and recover normal DA activity in brain. Therefore, it is of great significance to develop new antipsychotic drugs having a dual function of D1 agonistic and D2 antagonistic activity and further balancing DA activities, Parkinson's disease is a chronic progressive degenerative disorder, which is mainly characterized by the dopaminergic neuron loss in the substantia nigra. For a long time, L-Dopamine is a "gold standard" for the treatment of Parkinson's disease. However, long-term administration of L-Dopamine is often accompanied by high incidence of treatment-related complication, such as dyskinesias, efficacy loss and "on-off" phenomenon and the like, which are named as "L-Dopamine long-term syndrom", and the disease progression can not be delayed.

DA receptor agonist is one of various substitutive therapies for Parkinson's disease and mainly used with L-Dopamine in Parkinson's having dyskinesia. DA receptor agonist is superior to L-Dopamine for the following mechanism. In the later stage of Parkinson's disease, since dopamine decarboxylase activity of the nigrostriatal dopaminerigic system is depleted, exogenous L-Dopamine can not be transformed into DA through decarboxylation, and at this time, even a large dose of L-Dopamine preparation is ineffective. However, the function of DA receptor agonist is irrelevant to DA synthesis and does not depend on the activity of dopadecarboxylase. It has a molecular conformation similar to that of DA, and directly acts on the striatal synaptic DA receptor, primarily D1 receptor, and partially functions through D2 receptor. Therefore, the combination of DA receptor agonist can further improve the motor symptoms of Parkinson's disease. Based on such theory, if a D1 receptor agonist with selectivity is developed, it will be possible to provide a class of drugs with good effect for the treatment of Parkinson's disease. So far, many D1 receptor agonists with selectivity have been developed in various large companies, and many of them are in clinical trails. However, many drug candidates have low selectivity and obvious side effects. Therefore, it will undoubtedly have huge advantages and provide wide space for the treatment of Parkinson's disease to develop a D1 receptor selective agonist with high selectivity and little side effect.

Diarylo[a,g]quinolizines have a common chemical core structure, and various biological activities, including anti-inflammatory effect, antibacterial effect, anti-leukemia effect, anti-cancer effect and so on. Jin Guozhang, an academician of Chinese Academy of Sciences, together with others systematically studied the pharmacological activities of 6H-dibenzo[a,g]quinolizines and confirmed that levorotatory tetrahydropalmatine has good analgesic effect with sedation, tranquilizing and hypnotic effects, while dextrorotatory tetrahydropalmatine has no significant analgesic effect. It is also confirmed that levorotatory tetrahydropalmatine and other 6H-dibenzo[a,g]quinolizine alkaloids target the dopamine receptor. Jin Guozhang also first reported that 1-Stepholidine (1-SPD), one of 6H-dibenzo[a,g]quinolizines (THPBs), is the first leading compound having the dual function of D1 agonistic and D2 antagonistic activity (Jin G. Z. *TIPS*, 2002, 23-24). Clinical trial demonstrated that 1-SPD had good therapeutic effects on both the positive and negative symptoms with non-classical stabilizer features, and thus could be likely developed into a new class of antipsychotic drugs. Shen Jingshan, Yang Yushe et al. disclosed levorotatory Chloroscoulerine and 1-SPD derivatives with antipsychotic effect, and preparation methods and uses thereof, and especially levorotatory Scoulerine methanesulfonate with good water solubility and stability (WO2008/014661, CN03151464, and CN1900076). However, these compounds have a structure which has little room to be modified, and most of them have weak activity on D2 receptor, and many of them have no 5-HT activity with poor solubility and low bioavailability. Meanwhile, these compounds showed a certain degree of selectivity in D1 receptor vs D2 receptor. Therefore, it is of significance to continually modify diarylo[a,g]quinolizines, especially to develop a compound with better D2 activity or a D1 receptor agonist with better selectivity, thereby providing beneficial help for the treatment of Parkinson's disease.

The present invention provides a class of diarylo[a,g] quinolines with novel structures, and the synthesis and use thereof. Some of the compounds with such structure show good selectivity for D1 vs D2, and many of the compounds also have 5-HT activity. In addition, some of the compounds have dual pharmacological activities of good D1 agonist and D2 antagonist with good solubility, and can be used in the preparation of a medicament for treating neurological disease, especially those associated with dopamine receptors and serotonin receptor.

SUMMARY OF THE INVENTION

One object of the invention is to provide a class of diarylo[a,g]quinolizidines of formula (I), enantiomers, diastereoisomers, racemates and mixtures thereof, as well as pharmaceutically acceptable salts, and solvates thereof.

Another object of the invention is to provide a process for preparing the diarylo[a,g]quinolizidines of formula (I).

Still another object of the invention is to provide a pharmaceutical composition comprising one or more selected from the group consisting of the diarylo[a,g]quinolizines of formula (I), enantiomers, diastereoisomers, racemates and mixtures thereof, as well as pharmaceutically acceptable salts, and solvates thereof.

Still another object of the invention is to provide a use of the above-said compound of formula (I) in preparing a medicament for treating or preventing a disease related to dopamine receptors and 5-HT receptors, specially, a medicament for treating or preventing a disease such as schizophrenia, Parkinson's disease, mania, depression, drug addiction, migraine and the like.

Based on the above object, the present invention relates to a diarylo[a,g]quinolizidine compound of formula (I), an enantiomer, diastereoisomer, and racemate thereof, a mixture thereof, a pharmaceutically acceptable salt, or a solvate thereof.

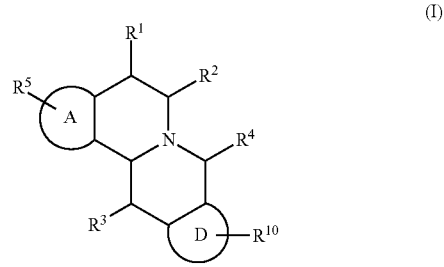

(I)

wherein, rings A and D are each independently a benzene ring or a 5-12 membered aromatic heterocycle containing 1 to 4 heteroatoms selected from the group consisting of O, S and N, and the rings A and D are not simultaneously a benzene ring; preferably, ring A is one selected from the group consisting of benzene ring, pyrrole ring, furan ring, thiophene ring, pyrazole ring, oxazole ring, isoxazole ring, thiazole ring, imidazole ring, benzofuran ring, benzopyrazole ring, benzoxazole ring, benzisoxazole ring, pyridine ring, pyrimidine ring, quinoline ring, isoquinoline ring, purine ring and indole ring; ring D is one selected from the group consisting of benzene ring, pyrrole ring, furan ring, thiophene ring, pyrazole ring, oxazole ring, isoxazole ring, thiazole ring, imidazole ring, benzofuran ring, benzopyrazole ring, benzoxazole ring, benzisoxazole ring, pyridine ring, pyrimidine ring, quinoline ring, isoquinoline ring and purine ring; and the rings A and D are not simultaneously a benzene ring; and more preferably, ring A is one selected from the group consisting of benzene ring, pyrrole ring, furan ring, thiophene ring, pyridine ring, benzoxazole ring, benzofuran ring and indole ring; ring D is one selected from the group consisting of benzene ring, pyrrole ring, furan ring, thiophene ring, pyridine ring, benzoxazole ring and benzofuran ring; and the rings A and D are not simultaneously a benzene ring;

$R^5$ and $R^{10}$ each independently represent 1 to 4 substituents selected from the group consisting of a hydrogen isotope, halogen, C1-C12 straight or branched alkyl unsubstituted or substituted with 1-3 halogens, C2-C12 straight or branched alkenyl or alkynyl unsubstituted or substituted with 1-3 halogens, C3-C6 cycloalkyl unsubstituted or substituted with 1-3 halogens, C1-C6 straight or branched alkyl substituted with C1-C6 alkoxy, C1-C6 straight or branched alkyl substituted with C3-C6 cycloalkyl, C1-C12 straight or branched alkyl substituted with 1-3 hydroxys, cyano, nitro, —OR⁶, —NR⁶R⁷, —SR⁶, —COOR⁶, —OR⁹OR⁶, —OR⁹COOR⁶, —OR⁹NR⁶R⁷, —R⁹COOR⁶, —R⁹CONR⁶R⁷, —R⁹OR⁶, —R⁹NR⁶R⁷, —N(R⁶)SO₂R⁷, —R⁸, —R⁹R⁸, —OR⁹R⁸, —NHR⁹R⁸ and —SO₂NR⁶R⁷; and preferably, from the group consisting of a hydrogen isotope, halogen, C1-C6 straight or branched alkyl unsubstituted or substituted with 1-3 halogens, C2-C6 straight or branched alkenyl or alkynyl unsubstituted or substituted with 1-3 halogens, C3-C6 cycloalkyl unsubstituted or substituted with 1-3 halogens, C1-C6 straight or branched alkyl substituted with C1-C6 alkoxy, C1-C6 straight or branched alkyl substituted with C3-C6 cycloalkyl, C1-C6 straight or branched alkyl substituted with 1-3 hydroxys, —OR⁶, —NR⁶R⁷, —OR⁹OR⁶, —OR⁹COOR⁶, —OR⁹NR⁶R⁷, —R⁹COOR⁶, —R⁹CONR⁶R⁷, —R⁹OR⁶, —R⁹NR⁶R⁷, —N(R⁶)SO₂R⁷, —R⁸, —R⁹R⁸, —OR⁹R⁸ and —NHR⁹R⁸; and more preferably, from the group consisting of hydrogen isotope, halogen, C1-C6 straight or branched alkyl unsubstituted or substituted with 1-3 halogens, C3-C6 cycloalkyl unsubstituted or substituted with 1-3 halogens, C1-C6 straight or branched alkyl substituted with a C1-C6 alkoxy, C1-C6 straight or branched alkyl substituted with a C3-C6 cycloalkyl, C1-C6 straight or branched alkyl substituted with 1-3 hydroxys, —OR⁶, —NR⁶R⁷, —OR⁹OR⁶, —OR⁹NR⁶R⁷, —R⁹COOR⁶, —R⁹CONR⁶R⁷, —R⁹OR⁶, —R⁹NR⁶R⁷, —N(R⁶)SO₂R⁷, —R⁹R⁸ and —OR⁹R⁸;

alternatively, any two adjacent R⁵s or adjacent R¹⁰s, together with the carbon atom or the heteroatom to which they are adjacent, may form a 5-7 membered heterocycle containing 1 to 3 heteroatoms selected from the group consisting of N, O and S, which may be optionally substituted with one or more selected from the group consisting of hydrogen, a hydrogen isotope, halogen, C1-C6 straight or branched alkyl unsubstituted or substituted with 1-3 halogens, C1-C6 straight or branched alkoxy unsubstituted or substituted with 1-3 halogens, hydroxy, oxo (═O), and amino group; preferably, any two adjacent R⁵s or adjacent R¹⁰s, together with the carbon atom or the heteroatom to which they are adjacent, form a 5-7 membered heterocycle containing 1 to 3 heteroatoms selected from the group consisting of N, O and S, which may be optionally substituted with one or more selected from the group consisting of hydrogen, a hydrogen isotope, halogen, C1-C6 straight or branched alkyl, hydroxy, oxo (═O), and amino;

R¹, R², R³ and R⁴ are each independently hydrogen, a hydrogen isotope, halogen, amino, hydroxy, oxo (═O), C1-C6 straight or branched alkyl unsubstituted or substituted with 1-3 halogens, C1-C6 straight or branched alkoxy unsubstituted or substituted with 1-3 halogens, C3-C6 cycloalkyl unsubstituted or substituted with 1-3 halogens, or C1-C6 straight or branched alkylcarbonyl unsubstituted or substituted with 1-3 halogens; and preferably, R¹, R², R³ and R⁴ are each independently hydrogen, halogen, amino, hydroxy, oxo (═O), or C1-C3 straight or branched alkyl unsubstituted or substituted with 1-3 halogens;

R⁸ is a 5-7 membered heterocyclyl containing 1-2 heteroatoms selected from the group consisting of N and O, which may be optionally substituted with one or more selected from the group consisting of hydrogen, a hydrogen isotope, halogen, —R⁹H, —R⁹OR⁶, and —R⁹NR⁶R⁷;

R⁶ and R⁷ are each independently hydrogen, a hydrogen isotope, halogen, C1-C6 straight or branched alkyl unsubstituted or substituted with 1-3 halogens or hydroxys, C3-C6 cycloalkyl unsubstituted or substituted with 1-3 halogens, C1-C6 acyl, C5-C12 aryl, unsubstituted or substituted 5- to 7-membered heterocyclyl containing 1 to 4 heteroatoms selected from the group consisting of O, S and N, or benzyl; the substituent in the substituted 5- to 7-membered heterocyclyl is one or more selected from the group consisting of halogen, C1-C6 straight or branched alkyl, C1-C6 straight or branched alkoxy, C3-C6 cycloalkyl, saturated or unsaturated C3-C7 heterocyclyl, cyano, nitro, amino, hydroxy, hydroxymethyl, methyl substituted with 1-3 fluorine atoms, methoxy substituted with 1-3 fluorine atoms, carboxyl, mercapto, and —R⁹OH; alternatively, R⁶ and R⁷ together with the nitrogen atom to which they attached to may form a ring;

R⁹ is C1-C6 straight or branched alkylene;

the halogen is F, Cl, Br or I, and preferably, F, Cl or Br; and the chiral carbon atom in the compound of formula (I) may be in R- or S-configuration.

More preferably, the diarylo[a,g]quinolizine compound according to the present invention is selected from the group consisting of

| No. | Name | Structure |
| --- | --- | --- |
| AS001 | (S)-8-methoxy-9-hydroxy-4,7,12,12a-tetrahydro-5H-benzo[g]thieno[3,2-a]quinolizine | 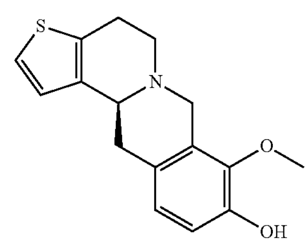 [SMILES: COc1c(O)ccc2c1CN1CCc3sccc3[C@@H]1C2] |
| AS002 | (R)-8-methoxy-9-hydroxy-4,7,12,12a-tetrahydro-5H-benzo[g]thieno[3,2-a]quinolizine | 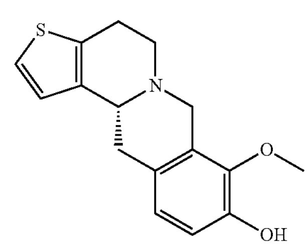 [SMILES: COc1c(O)ccc2c1CN1CCc3sccc3[C@H]1C2] |

| No. | Name | Structure |
|---|---|---|
| AS003 | (S)-2-methyl-8-methoxy-9-hydroxy-4,7,12,12a-tetrahydro-5H-benzo[g]thieno[3,2-a]quinolizine | 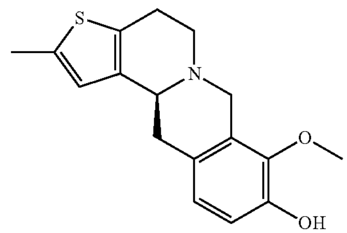 |
| AS004 | (R)-2-methyl-8-methoxy-9-hydroxy-4,7,12,12a-tetrahydro-5H-benzo[g]thieno[3,2-a]quinolizine | 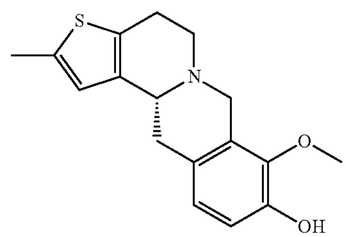 |
| AS005 | (S)-2-ethyl-8-methoxy-9-hydroxy-4,7,12,12a-tetrahydro-5H-benzo[g]thieno[3,2-a]quinolizine | 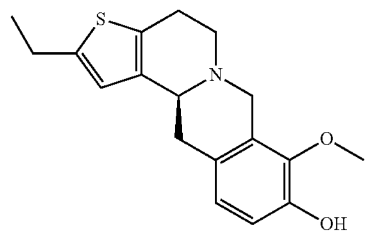 [SMILES: CCc1cc2c(s1)CCN1Cc3c(ccc(O)c3OC)C[C@@H]21] |
| AS006 | (S)-2-n-propyl-8-methoxy-9-hydroxy-4,7,12,12a-tetrahydro-5H-benzo[g]thieno[3,2-a]quinolizine | 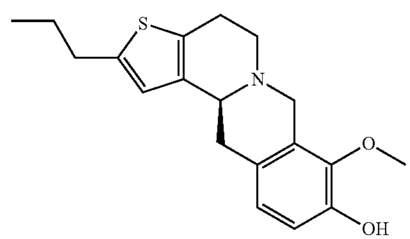 [SMILES: CCCc1cc2c(s1)CCN1Cc3c(ccc(O)c3OC)C[C@@H]21] |
| AS007 | (S)-2-n-butyl-8-methoxy-9-hydroxy-4,7,12,12a-tetrahydro-5H-benzo[g]thieno[3,2-a]quinolizine | 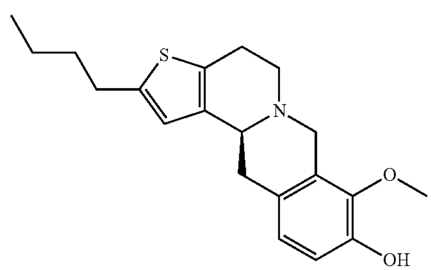 [SMILES: CCCCc1cc2c(s1)CCN1Cc3c(ccc(O)c3OC)C[C@@H]21] |
| AS008 | (S)-2-n-pentyl-8-methoxy-9-hydroxy-4,7,12,12a-tetrahydro-5H-benzo[g]thieno[3,2-a]quinolizine | 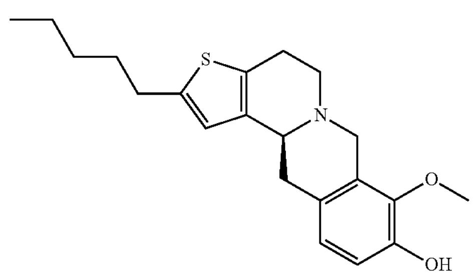 [SMILES: CCCCCc1cc2c(s1)CCN1Cc3c(ccc(O)c3OC)C[C@@H]21] |

-continued

| No. | Name | Structure |
|---|---|---|
| AS009 | (S)-2-(2-methylpropyl)-8-methoxy-9-hydroxy-4,7,12,12a-tetrahydro-5H-benzo[g]thieno[3,2-a]quinolizine | 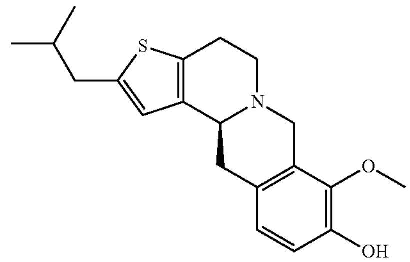 |
| AS010 | (S)-2-(3-methylbutyl)-8-methoxy-9-hydroxy-4,7,12,12a-tetrahydro-5H-benzo[g]thieno[3,2-a]quinolizine | 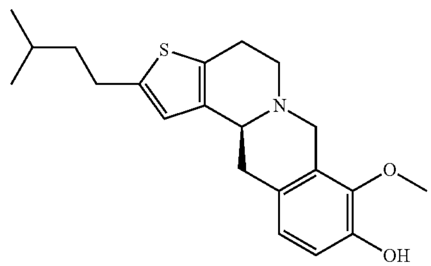 [SMILES: COc1c(O)ccc2c1CN1CCc3sc(CCC(C)C)cc3[C@@H]1C2] |
| AS011 | (S)-2-cyclopropylmethyl-8-methoxy-9-hydroxy-4,7,12,12a-tetrahydro-5H-benzo[g]thieno[3,2-a]quinolizine | 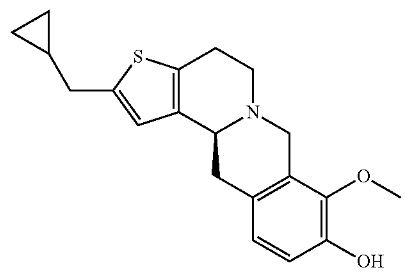 |
| AS012 | (S)-2-cyclobutylmethyl-8-methoxy-9-hydroxy-4,7,12,12a-tetrahydro-5H-benzo[g]thieno[3,2-a]quinolizine | 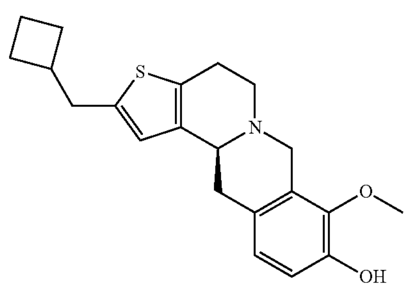 [SMILES: COc1c(O)ccc2c1CN1CCc3sc(CC4CCC4)cc3[C@@H]1C2] |
| AS013 | (S)-2-(2,2-dimethylpropyl)-8-methoxy-9-hydroxy-4,7,12,12a-tetrahydro-5H-benzo[g]thieno[3,2-a]quinolizine | 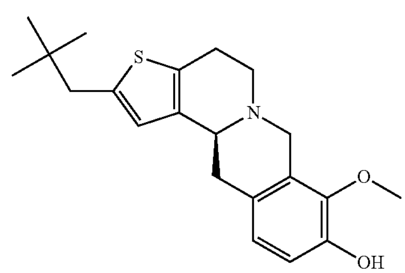 [SMILES: COc1c(O)ccc2c1CN1CCc3sc(CC(C)(C)C)cc3[C@@H]1C2] |

-continued

| No. | Name | Structure |
|---|---|---|
| AS014 | (S)-2-(3,3-dimethylbutyl)-8-methoxy-9-hydroxy-4,7,12,12a-tetrahydro-5H-benzo[g]thieno[3,2-a]quinolizine | 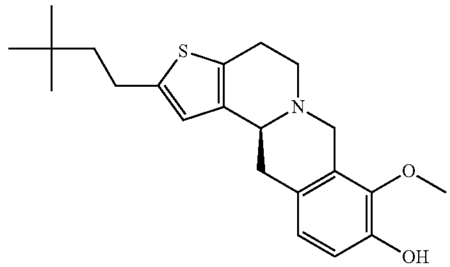 [SMILES: COc1c(O)ccc2c1CN1CCc3sc(CCC(C)(C)C)cc3[C@@H]1C2] |
| AS015 | (S)-2-(2-methylbutyl)-8-methoxy-9-hydroxy-4,7,12,12a-tetrahydro-5H-benzo[g]thieno[3,2-a]quinolizine | 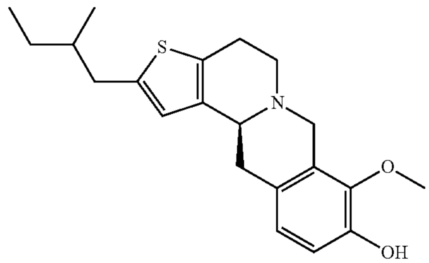 [SMILES: CCC(C)Cc1cc2c(s1)CCN1Cc3c(ccc(O)c3OC)C[C@@H]21] |
| AS016 | (S)-2-(2-chlorethyl)-8-methoxy-9-hydroxy-4,7,12,12a-tetrahydro-5H-benzo[g]thieno[3,2-a]quinolizine | 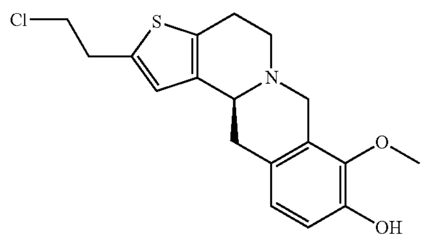 [SMILES: COc1c(O)ccc2c1CN1CCc3sc(CCCl)cc3[C@@H]1C2] |
| AS017 | (S)-2-(3-chloropropyl)-8-methoxy-9-hydroxy-4,7,12,12a-tetrahydro-5H-benzo[g]thieno[3,2-a]quinolizine | 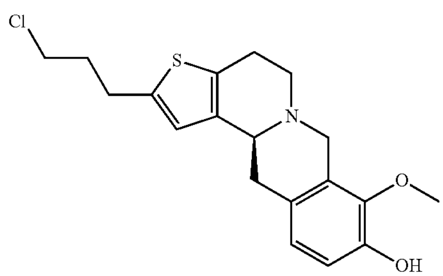 [SMILES: COc1c(O)ccc2c1CN1CCc3sc(CCCCl)cc3[C@@H]1C2] |
| AS018 | (S)-2-(2-chloropropyl)-8-methoxy-9-hydroxy-4,7,12,12a-tetrahydro-5H-benzo[g]thieno[3,2-a]quinolizine | 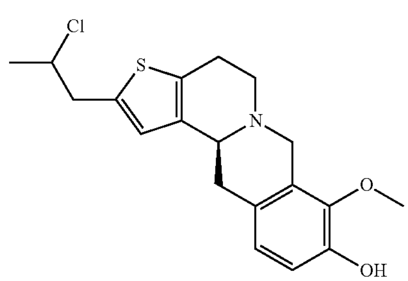 [SMILES: COc1c(O)ccc2c1CN1CCc3sc(CC(C)Cl)cc3[C@@H]1C2] |
| AS019 | (S)-2-(4-chlorobutyl)-8-methoxy-9-hydroxy-4,7,12,12a-tetrahydro-5H-benzo[g]thieno[3,2-a]quinolizine | 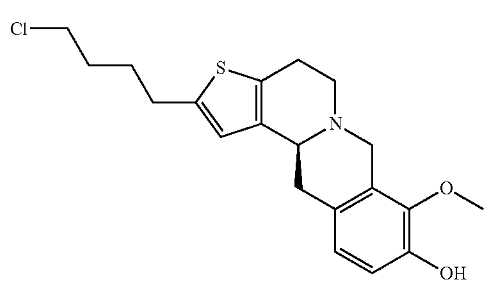 [SMILES: COc1c(O)ccc2c1CN1CCc3sc(CCCCCl)cc3[C@@H]1C2] |

-continued

| No. | Name | Structure |
|---|---|---|
| AS020 | (S)-2-(3-bromopropyl)-8-methoxy-9-hydroxy-4,7,12,12a-tetrahydro-5H-benzo[g]thieno[3,2-a]quinolizine | 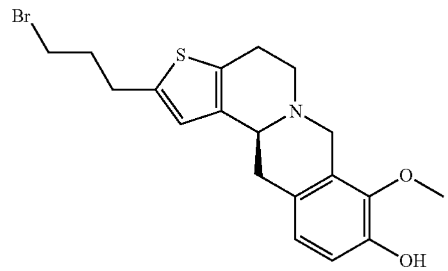 |
| AS021 | (S)-2-(2,2,2-trifluoroethyl)-8-methoxy-9-hydroxy-4,7,12,12a-tetrahydro-5H-benzo[g]thieno[3,2-a]quinolizine | 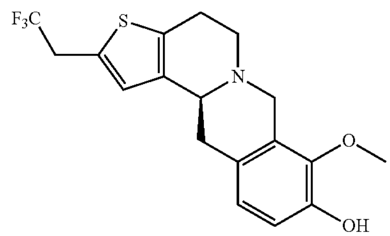 [SMILES: COc1c(O)ccc2c1CN1CCc3sc(CC(F)(F)F)cc3[C@@H]1C2] |
| AS022 | (S)-8,9-dimethoxy-4,7,12,12a-tetrahydro-5H-benzo[g]thieno[3,2-a]quinolizine | 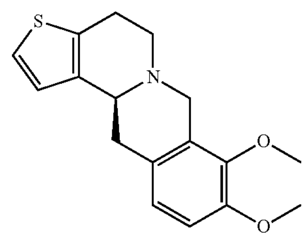 [SMILES: COc1ccc2c(c1OC)CN1CCc3sccc3[C@@H]1C2] |
| AS023 | (S)-2-methyl-8,9-dimethoxy-4,7,12,12a-tetrahydro-5H-benzo[g]thieno[3,2-a]quinolizine | 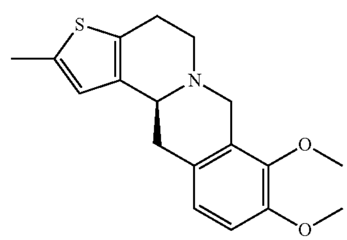 |
| AS024 | (S)-2-ethyl-8,9-dimethoxy-4,7,12,12a-tetrahydro-5H-benzo[g]thieno[3,2-a]quinolizine | 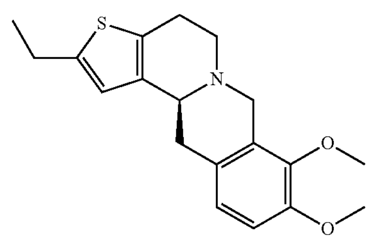 [SMILES: CCc1cc2c(s1)CCN1Cc3c(ccc(OC)c3OC)C[C@@H]21] |
| AS025 | (S)-2-n-propyl-8,9-dimethoxy-4,7,12,12a-tetrahydro-5H-benzo[g]thieno[3,2-a]quinolizine | 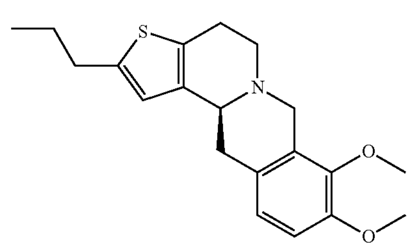 [SMILES: CCCc1cc2c(s1)CCN1Cc3c(ccc(OC)c3OC)C[C@@H]21] |

-continued

| No. | Name | Structure |
|---|---|---|
| AS026 | (S)-2-(2-methylpropyl)-8,9-dimethoxy-4,7,12,12a-tetrahydro-5H-benzo[g]thieno[3,2-a]quinolizine | 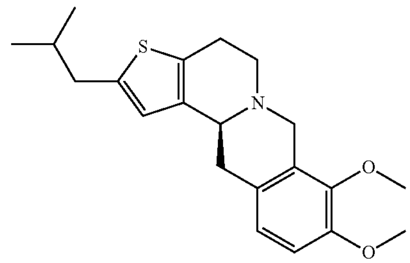 [SMILES: COc1ccc2c(c1OC)CN1CCc3sc(CC(C)C)cc3[C@@H]1C2] |
| AS027 | (S)-2-cyclopropylmethyl-8,9-dimethoxy-4,7,12,12a-tetrahydro-5H-benzo[g]thieno[3,2-a]quinolizine | 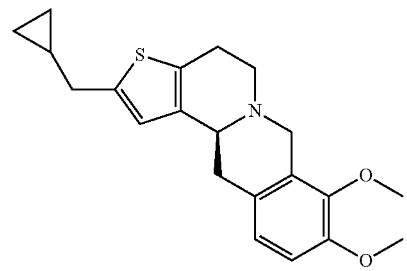 [SMILES: COc1ccc2c(c1OC)CN1CCc3sc(CC4CC4)cc3[C@@H]1C2] |
| AS028 | (S)-2-(2,2-dimethylpropyl)-8,9-dimethoxy-4,7,12,12a-tetrahydro-5H-benzo[g]thieno[3,2-a]quinolizine | 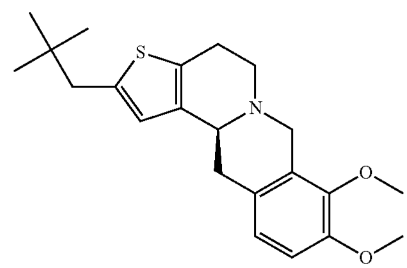 [SMILES: COc1ccc2c(c1OC)CN1CCc3sc(CC(C)(C)C)cc3[C@@H]1C2] |
| AS029 | (S)-2-(2-chloroethyl)-8,9-dimethoxy-4,7,12,12a-tetrahydro-5H-benzo[g]thieno[3,2-a]quinolizine | 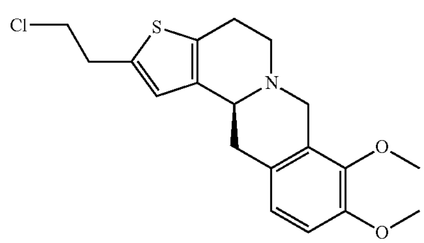 [SMILES: COc1ccc2c(c1OC)CN1CCc3sc(CCCl)cc3[C@@H]1C2] |
| AS030 | (S)-2-(2,2,2-trifluoroethyl)-8,9-dimethoxy-4,7,12,12a-tetrahydro-5H-benzo[g]thieno[3,2-a]quinolizine | 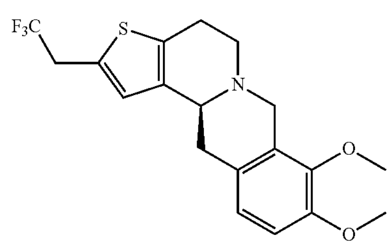 [SMILES: COc1ccc2c(c1OC)CN1CCc3sc(CC(F)(F)F)cc3[C@@H]1C2] |
| AS031 | (S)-8,11-dimethoxy-4,7,12,12a-tetrahydro-5H-benzo[g]thieno[3,2-a]quinolizine | 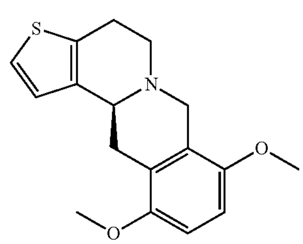 [SMILES: COc1ccc(OC)c2c1C[C@H]1c3ccsc3CCN1C2] |

-continued

| No. | Name | Structure |
|---|---|---|
| AS032 | (S)-2-methyl-8,11-dimethoxy-4,7,12,12a-tetrahydro-5H-benzo[g]thieno[3,2-a]quinolizine | 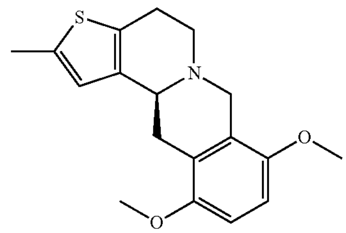 |
| AS034 | (S)-2-ethyl-8,11-dimethoxy-4,7,12,12a-tetrahydro-5H-benzo[g]thieno[3,2-a]quinolizine | |
| AS034 | (S)-2-(2-methylpropyl)-8,11-dimethoxy-4,7,12,12a-tetrahydro-5H-benzo[g]thieno[3,2-a]quinolizine | |
| AS035 | (S)-2-cyclopropylmethyl-8,11-dimethoxy-4,7,12,12a-tetrahydro-5H-benzo[g]thieno[3,2-a]quinolizine | 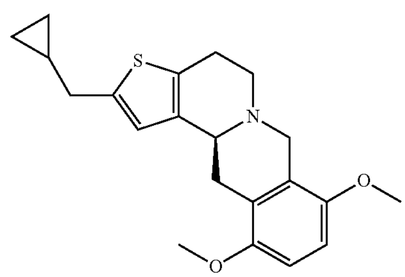 [SMILES: COc1ccc(OC)c2c1C[C@H]1c3cc(CC4CC4)sc3CCN1C2] |
| AS036 | (S)-2-(2-chloroethyl)-8,11-dimethoxy-4,7,12,12a-tetrahydro-5H-benzo[g]thieno[3,2-a]quinolizine | 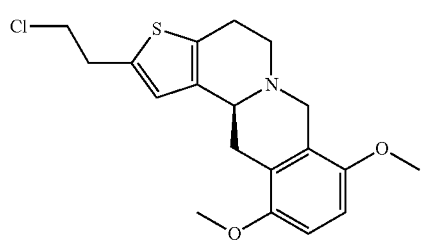 [SMILES: COc1ccc(OC)c2c1C[C@H]1c3cc(CCCl)sc3CCN1C2] |
| AS037 | (S)-2-(2,2,2-trifluoroethyl)-8,11-dimethoxy-4,7,12,12a-tetrahydro-5H-benzo[g]thieno[3,2-a]quinolizine | 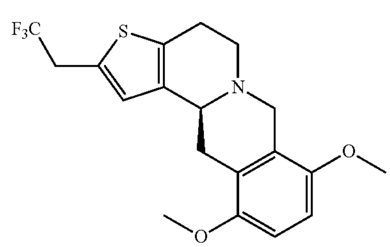 [SMILES: COc1ccc(OC)c2c1C[C@H]1c3cc(CC(F)(F)F)sc3CCN1C2] |

-continued

| No. | Name | Structure |
|---|---|---|
| AS038 | (S)-2,4-dimethyl-8-methoxy-9-hydroxy-4,7,12,12a-tetrahydro-5H-benzo[g]thieno[3,2-a]quinolizine | 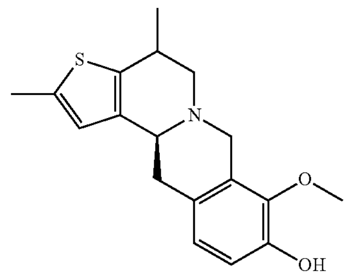 |
| AS039 | (S)-2,5-dimethyl-8-methoxy-9-hydroxy-4,7,12,12a-tetrahydro-5H-benzo[g]thieno[3,2-a]quinolizine | 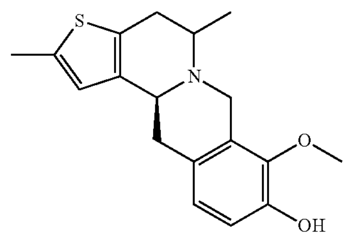 |
| AS040 | (S)-2,7-dimethyl-8-methoxy-9-hydroxy-4,7,12,12a-tetrahydro-5H-benzo[g]thieno[3,2-a]quinolizine | 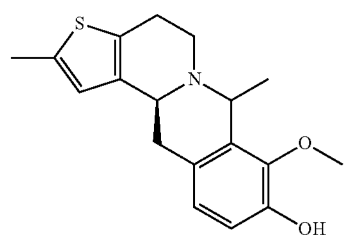 |
| AS041 | (S)-2-methyl-8-methoxy-9-hydroxy-4,7,12,12a-tetrahydro-5H-benzo[g]thieno[3,2-a]quinolizin-7(5H)-one | 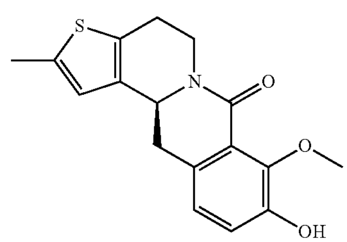 |
| AS042 | (S)-1,2-dimethyl-8-methoxy-9-hydroxy-4,7,12,12a-tetrahydro-5H-benzo[g]thieno[3,2-a]quinolizine | 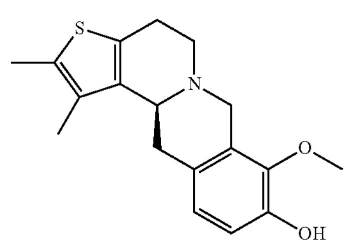 |
| AS043 | (S)-2,8-dimethoxy-9-hydroxy-4,7,12,12a-tetrahydro-5H-benzo[g]thieno[3,2-a]quinolizine | 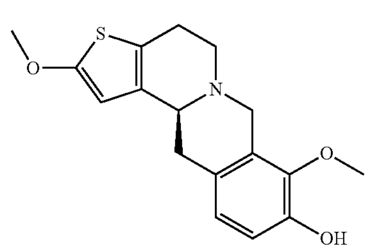 |

-continued

| No. | Name | Structure |
|---|---|---|
| AS044 | (S)-2-fluoro-8-methoxy-9-hydroxy-4,7,12,12a-tetrahydro-5H-benzo[g]thieno[3,2-a]quinolizine | 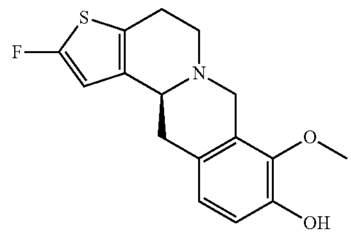 [SMILES: COc1c(O)ccc2c1CN1CCc3sc(F)cc3[C@@H]1C2] |
| AS045 | (S)-2-methyl-8-methoxy-9-hydroxy-4,7,12,12a-tetrahydro-5H-benzo[g]thieno[2,3-a]quinolizine | 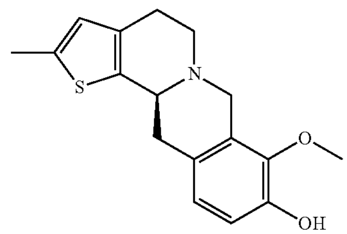 |
| AS046 | (S)-2,8-dimethoxy-9-hydroxy-4,7,12,12a-tetrahydro-5H-benzo[g]thieno[2,3-a]quinolizine | 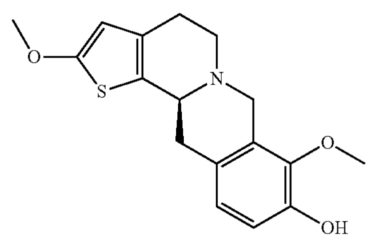 |
| AS047 | (S)-8-methoxy-9-acetoxy-4,7,12,12a-tetrahydro-5H-benzo[g]thieno[3,2-a]quinolizine | 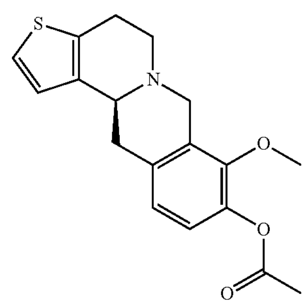 [SMILES: COc1c(OC(C)=O)ccc2c1CN1CCc3sccc3[C@@H]1C2] |
| AS048 | (S)-8-methoxy-9-(2'-hydroxyethoxy)-4,7,12,12a-tetrahydro-5H-benzo[g]thieno[3,2-a]quinolizine | 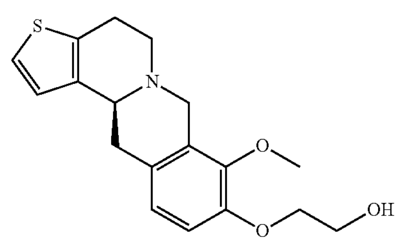 [SMILES: COc1c(OCCO)ccc2c1CN1CCc3sccc3[C@@H]1C2] |
| AS049 | (S)-8-methoxy-9-(2'-dimethylaminoethoxy)-4,7,12,12a-tetrahydro-5H-benzo[g]thieno[3,2-a]quinolizine | 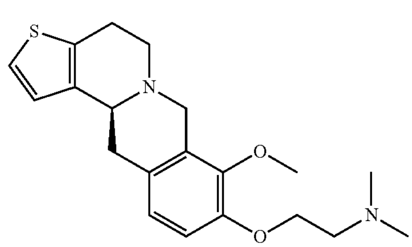 [SMILES: COc1c(OCCN(C)C)ccc2c1CN1CCc3sccc3[C@@H]1C2] |

| No. | Name | Structure |
|---|---|---|
| AS050 | (S)-8-methoxy-9-amino-4,7,12,12a-tetrahydro-5H-benzo[g]thieno[3,2-a]quinolizine | 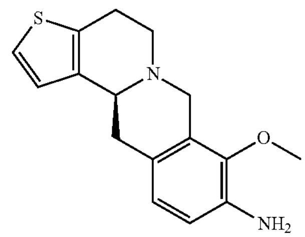 [SMILES: COc1c(N)ccc2c1CN1CCc3sccc3[C@@H]1C2] |
| AS051 | (S)-8-methoxy-9-acetylamino-4,7,12,12a-tetrahydro-5H-benzo[g]thieno[3,2-a]quinolizine | 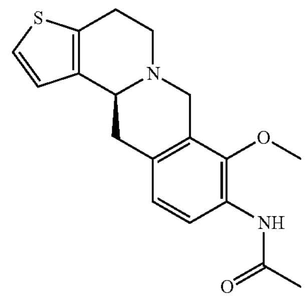 [SMILES: COc1c(NC(C)=O)ccc2c1CN1CCc3sccc3[C@@H]1C2] |
| AS052 | (S)-8-methoxy-9-methylsulfonylamino-4,7,12,12a-tetrahydro-5H-benzo[g]thieno[3,2-a]quinolizine | 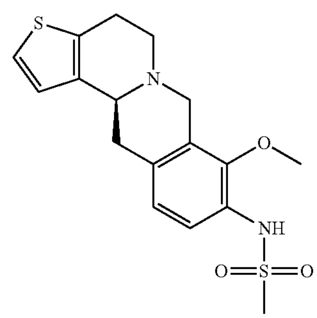 [SMILES: COc1c(NS(C)(=O)=O)ccc2c1CN1CCc3sccc3[C@@H]1C2] |
| AS053 | (S)-2-methyl-8-methoxy-9-((2-morpholino)ethoxy)-4,7,12,12a-tetrahydro-5H-benzo[g]thieno[3,2-a]quinolizine | 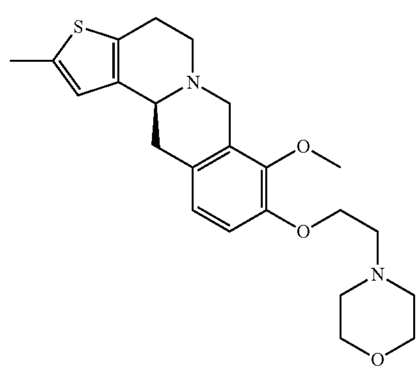 [SMILES: COc1c(OCCN2CCOCC2)ccc2c1CN1CCc3sc(C)cc3[C@@H]1C2] |
| AF001 | (S)-8-methoxy-9-hydroxy-4,7,12,12a-tetrahydro-5H-benzo[g]furo[3,2-a]quinolizine | 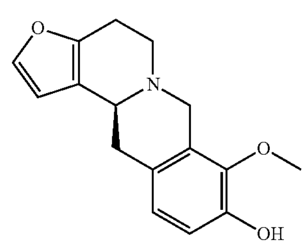 [SMILES: COc1c(O)ccc2c1CN1CCc3occc3[C@@H]1C2] |

-continued

| No. | Name | Structure |
|-----|------|-----------|
| AF002 | (S)-2-methyl-8-methoxy-9-hydroxy-4,7,12,12a-tetrahydro-5H-benzo[g]furo[3,2-a]quinolizine | 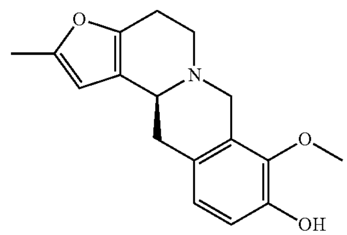 |
| AF003 | (S)-2-ethyl-8-methoxy-9-hydroxy-4,7,12,12a-tetrahydro-5H-benzo[g]furo[3,2-a]quinolizine | 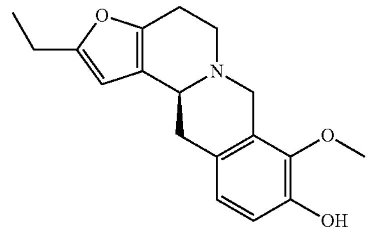 |
| AF004 | (S)-2-(2-methylpropyl)-8-methoxy-9-hydroxy-4,7,12,12a-tetrahydro-5H-benzo[g]furo[3,2-a]quinolizine | 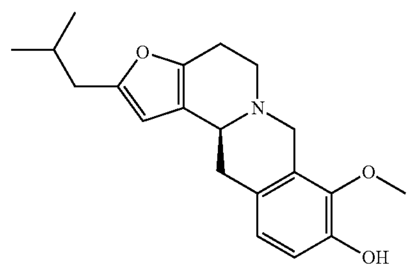 |
| AF005 | (S)-2-cyclopropylmethyl-8-methoxy-9-hydroxy-4,7,12,12a-tetrahydro-5H-benzo[g]furo[3,2-a]quinolizine | 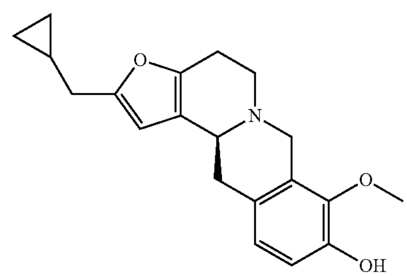 [SMILES: COc1c(O)ccc2c1CN1CCc3oc(CC4CC4)cc3[C@@H]1C2] |
| AF006 | (S)-2-(2-chloroethyl)-8-methoxy-9-hydroxy-4,7,12,12a-tetrahydro-5H-benzo[g]furo[3,2-a]quinolizine | 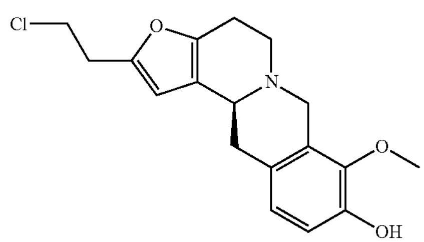 [SMILES: COc1c(O)ccc2c1CN1CCc3oc(CCCl)cc3[C@@H]1C2] |
| AF007 | (S)-2-methyl-8-methoxy-9-hydroxy-4,7,12,12a-tetrahydro-5H-benzo[g]furo[2,3-a]quinolizine | 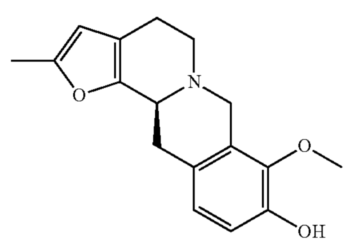 |

-continued

| No. | Name | Structure |
|---|---|---|
| AF008 | (S)-2-ethyl-8-methoxy-9-hydroxy-4,7,12,12a-tetrahydro-5H-benzo[g]furo[2,3-a]quinolizine | 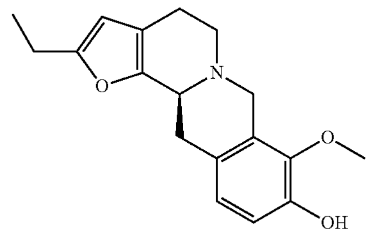 |
| AF009 | (S)-2-(2-chloroethyl)-8-methoxy-9-hydroxy-4,7,12,12a-tetrahydro-5H-benzo[g]furo[2,3-a]quinolizine | 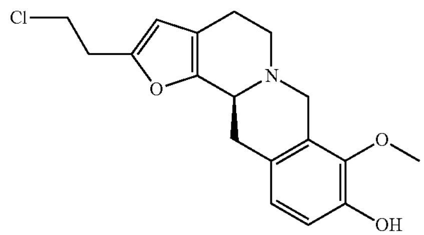 [SMILES: COc1c(O)ccc2c1CN1CCc3cc(CCCl)oc3[C@@H]1C2] |
| AI001 | (S)-2,3-dimethoxy-5,7,8,13,13b,14-hexahydroindolo[2',3':3,4]pyrido[1,2-b]isoquinoline | 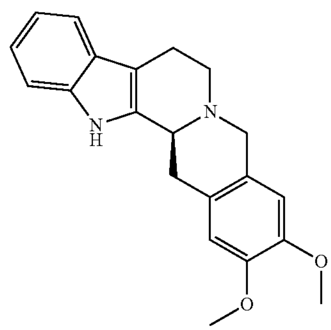 [SMILES: COc1cc2c(cc1OC)CN1CCc3c([nH]c4ccccc34)[C@@H]1C2] |
| AI002 | (S)-3-hydroxy-4-methoxy-5,7,8,13,13b,14-hexahydroindolo[2',3':3,4]pyrido[1,2-b]isoquinoline | 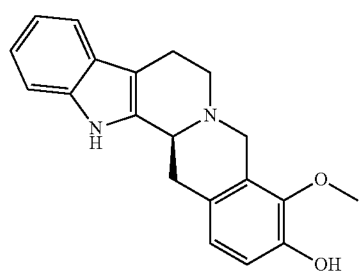 [SMILES: COc1c(O)ccc2c1CN1CCc3c([nH]c4ccccc34)[C@@H]1C2] |
| AI003 | (S)-3-hydroxy-4,10-dimethoxy-5,7,8,13,13b,14-hexahydroindolo[2',3':3,4]pyrido[1,2-b]isoquinoline | 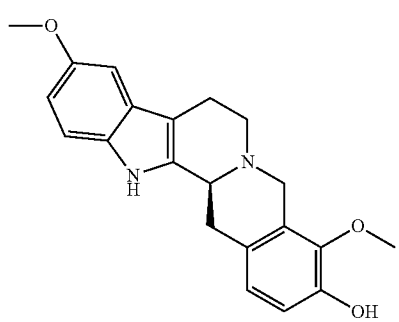 |

-continued

| No. | Name | Structure |
|---|---|---|
| AI004 | (S)-3-hydroxy-4-methoxy-10-methyl-5,7,8,13,13b,14-hexahydroindolo[2',3':3,4]pyrido[1,2-b]isoquinoline | 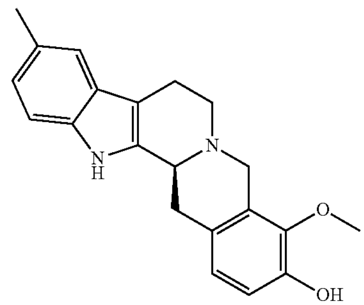 [SMILES: COc1c(O)ccc2c1CN1CCc3c([nH]c4ccc(C)cc34)[C@@H]1C2] |
| AI005 | (S)-3-hydroxy-4-methoxy-10-fluoro-5,7,8,13,13b,14-hexahydroindolo[2',3':3,4]pyrido[1,2-b]isoquinoline | 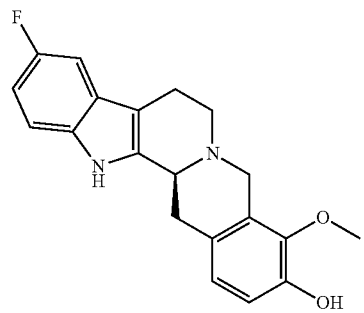 [SMILES: COc1c(O)ccc2c1CN1CCc3c([nH]c4ccc(F)cc34)[C@@H]1C2] |
| AI006 | (S)-3-hydroxy-4-methoxy-11-methyl-5,7,8,13,13b,14-hexahydroindolo[2',3':3,4]pyrido[1,2-b]isoquinoline | 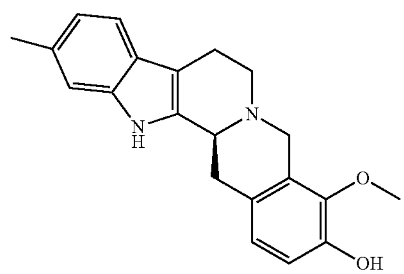 |
| AI007 | (S)-3-hydroxy-4,11-dimethoxy-5,7,8,13,13b,14-hexahydroindolo[2',3':3,4]pyrido[1,2-b]isoquinoline | 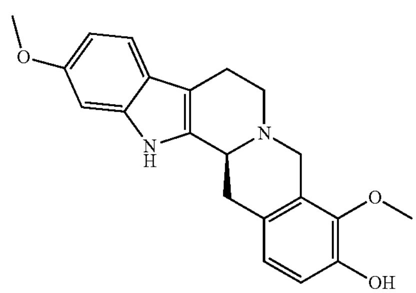 |
| AI008 | (S)-5,6,8,14,14a,15-hexahydro-[1,3]dioxolo[4,5-g]indolo[2',3':3,4]pyrido[1,2-b]isoquinoline | 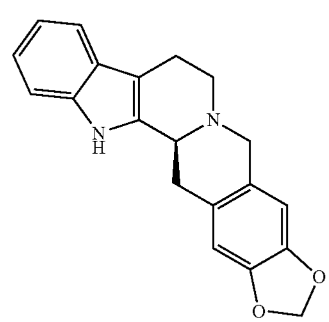 [SMILES: c1ccc2c3c([nH]c2c1)[C@@H]1Cc2cc4c(cc2CN1CC3)OCO4] |

-continued

| No. | Name | Structure |
|---|---|---|
| AI009 | (S)-3-hydroxy-2-methoxy-5,7,8,13,13b,14-hexahydroindolo[2',3':3,4]pyrido[1,2-b]isoquinoline | 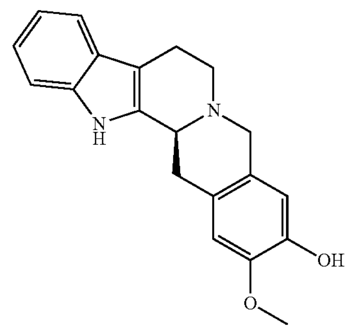 [SMILES: COc1cc2c(cc1O)CN1CCc3c([nH]c4ccccc34)[C@@H]1C2] |
| AI010 | (S)-2-hydroxy-3-methoxy-5,7,8,13,13b,14-hexahydroindolo[2',3':3,4]pyrido[1,2-b]isoquinoline | 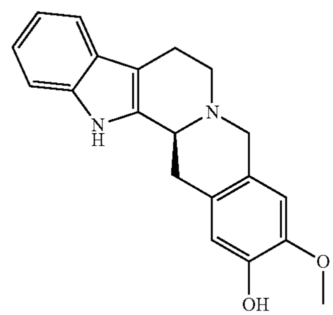 [SMILES: COc1cc2c(cc1O)C[C@H]1c3[nH]c4ccccc4c3CCN1C2] |
| AP001 | (S)-2,8-dimethoxy-9-hydroxy-4,7,12,12a-tetrahydro-5H-benzo[g]pyrrolo[2,3-a]quinolizine | 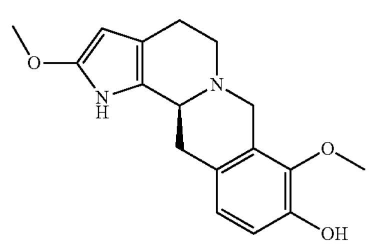 |
| AP002 | (S)-3,9-dimethoxy-10-hydroxy-5,8,13,13a-tetrahydro-6H-benzo[g]pyrido[2,3-a]quinolizine | 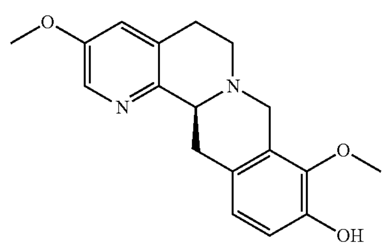 |
| AP003 | (S)-2,10-dihydroxy-3,9-dimethoxy-5,8,13,13a-tetrahydro-6H-benzo[g]pyrido[2,3-a]quinolizine | 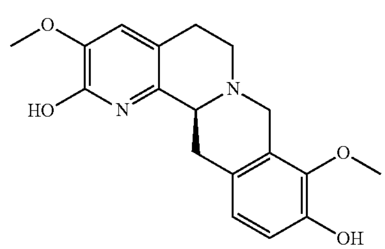 |

-continued

| No. | Name | Structure |
|---|---|---|
| AP004 | (S)-2,8-dimethoxy-9-hydroxy-4,7,12,12a-tetrahydro-5H-benzo[g]pyrrolo[3,2-a]quinolizine | 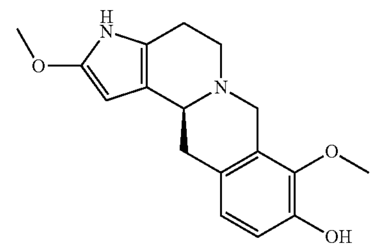 |
| AP005 | (S)-3,9-dimethoxy-6,8,13,13a-tetrahydro-5H-isoquinolino[3,2-f][1,6]naphthyridin-10-ol | 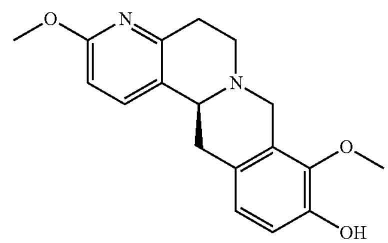 |
| AP006 | (S)-3,9-dimethoxy-6,8,13,13a-tetrahydro-5H-isoquinolino[3,2-f][1,6]naphthyridine-2,10-diol | 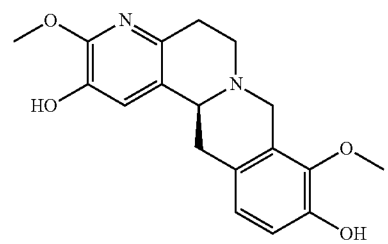 |
| DS001 | (S)-2-hydroxy-3-methoxy-5,8,12,12a-tetrahydro-6H-benzo[a]thieno[3,2-g]quinolizine | 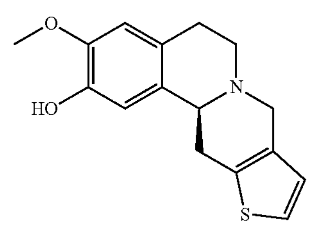 [SMILES: COc1cc2c(cc1O)[C@@H]1Cc3sccc3CN1CC2] |
| DS002 | (R)-2-hydroxy-3-methoxy-5,8,12,12a-tetrahydro-6H-benzo[a]thieno[3,2-g]quinolizine | 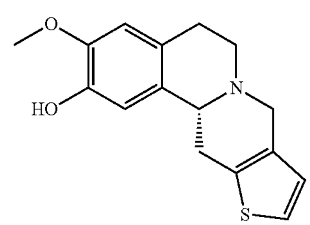 [SMILES: COc1cc2c(cc1O)[C@H]1Cc3sccc3CN1CC2] |
| DS003 | (S)-2-hydroxy-3-methoxy-10-ethyl-5,8,12,12a-tetrahydro-6H-benzo[a]thieno[3,2-g]quinolizine | 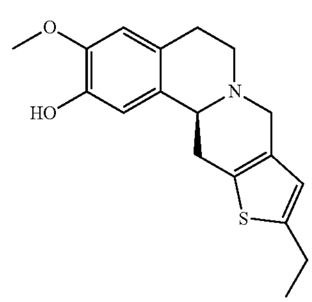 [SMILES: CCc1cc2c(s1)C[C@H]1c3cc(O)c(OC)cc3CCN1C2] |

-continued

| No. | Name | Structure |
|---|---|---|
| DS004 | (R)-2-hydroxy-3-methoxy-10-ethyl-5,8,12,12a-tetrahydro-6H-benzo[a]thieno[3,2-g]quinolizine | 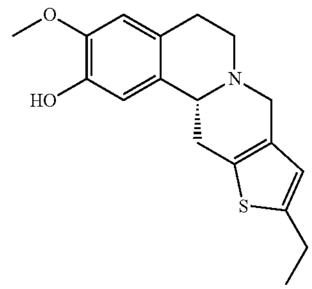 [SMILES: CCc1cc2c(s1)C[C@@H]1c3cc(O)c(OC)cc3CCN1C2] |
| DS005 | (S)-2-hydroxy-3-methoxy-10-n-propyl-5,8,12,12a-tetrahydro-6H-benzo[a]thieno[3,2-g]quinolizine | 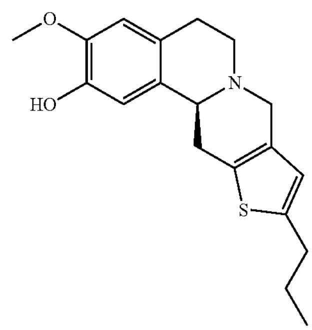 [SMILES: CCCc1cc2c(s1)C[C@H]1c3cc(O)c(OC)cc3CCN1C2] |
| DS006 | (S)-2-hydroxy-3-methoxy-10-(2-methylpropyl)-5,8,12,12a-tetrahydro-6H-benzo[a]thieno[3,2-g]quinolizine | 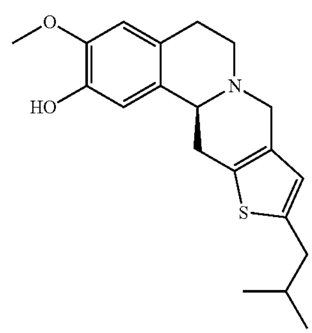 [SMILES: COc1cc2c(cc1O)[C@@H]1Cc3sc(CC(C)C)cc3CN1CC2] |
| DS007 | (S)-2-hydroxy-3-methoxy-10-n-butyl-5,8,12,12a-tetrahydro-6H-benzo[a]thieno[3,2-g]quinolizine | 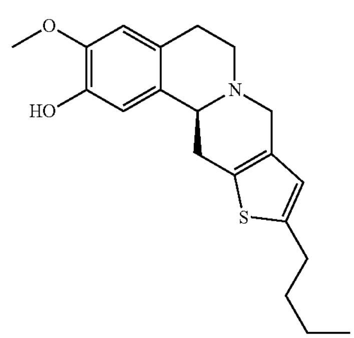 [SMILES: CCCCc1cc2c(s1)C[C@H]1c3cc(O)c(OC)cc3CCN1C2] |

-continued

| No. | Name | Structure |
|---|---|---|
| DS008 | (S)-2-hydroxy-3-methoxy-10-(3-methylbutyl)-5,8,12,12a-tetrahydro-6H-benzo[a]thieno[3,2-g]quinolizine | 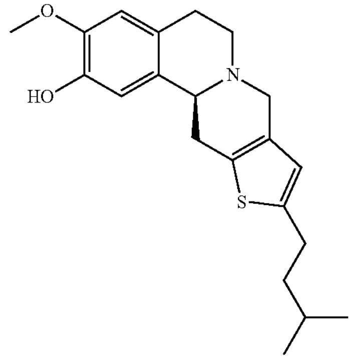 [SMILES: COc1cc2c(cc1O)[C@@H]1Cc3sc(CCC(C)C)cc3CN1CC2] |
| DS009 | (S)-2-hydroxy-3-methoxy-10-n-pentyl-5,8,12,12a-tetrahydro-6H-benzo[a]thieno[3,2-g]# quinolizine | 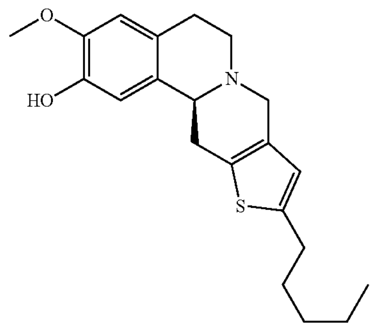 [SMILES: CCCCCc1cc2c(s1)C[C@H]1c3cc(O)c(OC)cc3CCN1C2] |
| DS010 | (S)-2-hydroxy-3-methoxy-10-(4-methylpentyl)-5,8,12,12a-tetrahydro-6H-benzo[a]thieno[3,2-g]quinolizine | 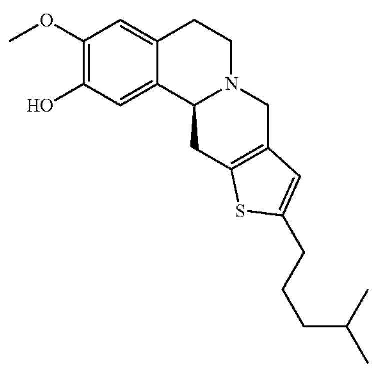 [SMILES: COc1cc2c(cc1O)[C@@H]1Cc3sc(CCCC(C)C)cc3CN1CC2] |
| DS011 | (S)-2-hydroxy-3-methoxy-10-cyclopropylmethyl-5,8,12,12a-tetrahydro-6H-benzo[a]thieno[3,2-g]quinolizine | 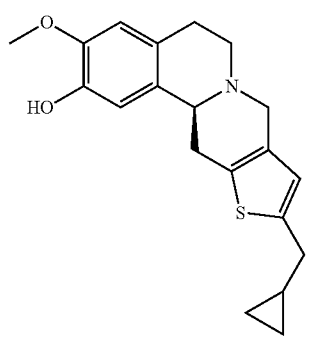 [SMILES: COc1cc2c(cc1O)[C@@H]1Cc3sc(CC4CC4)cc3CN1CC2] |

-continued

| No. | Name | Structure |
|---|---|---|
| DS012 | (S)-2-hydroxy-3-methoxy-10-cyclobutylmethyl-5,8,12,12a-tetrahydro-6H-benzo[a]thieno[3,2-g]quinolizine | 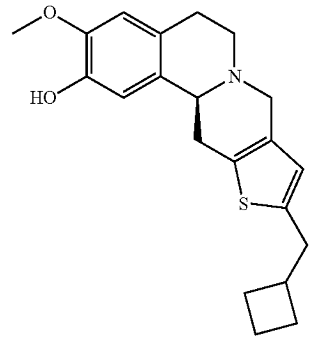 [SMILES: COc1cc2c(cc1O)[C@@H]1Cc3sc(CC4CCC4)cc3CN1CC2] |
| DS013 | (S)-2-hydroxy-3-methoxy-10-(2-chloroethyl)-5,8,12,12a-tetrahydro-6H-benzo[a]thieno[3,2-g]quinolizine | 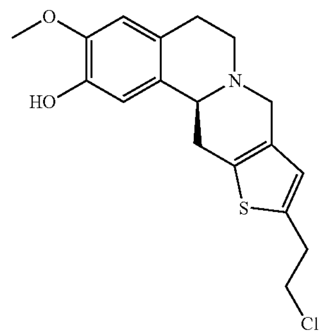 [SMILES: COc1cc2c(cc1O)[C@@H]1Cc3sc(CCCl)cc3CN1CC2] |
| DS014 | (12aS)-2-hydroxy-3-methoxy-10-(2-chloropropyl)-5,8,12,12a-tetrahydro-6H-benzo[a]thieno[3,2-g]quinolizine | 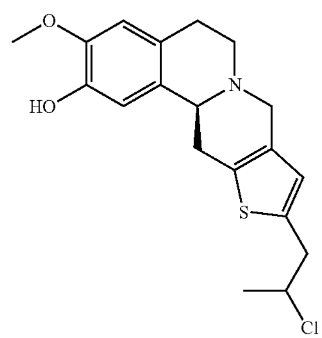 [SMILES: COc1cc2c(cc1O)[C@@H]1Cc3sc(CC(C)Cl)cc3CN1CC2] |
| DS015 | (S)-2-hydroxy-3-methoxy-10-(3-chloropropyl)-5,8,12,12a-tetrahydro-6H-benzo[a]thieno[3,2-g]quinolizine | 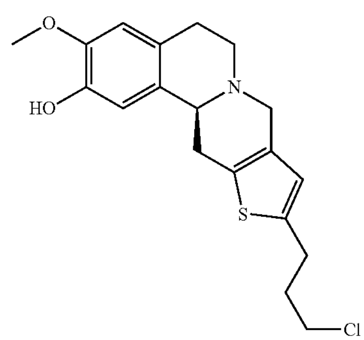 [SMILES: COc1cc2c(cc1O)[C@@H]1Cc3sc(CCCCl)cc3CN1CC2] |

-continued

| No. | Name | Structure |
|---|---|---|
| DS016 | (S)-2-hydroxy-3-methoxy-10-(4-chlorobutyl)-5,8,12,12a-tetrahydro-6H-benzo[a]thieno[3,2-g]quinolizine | 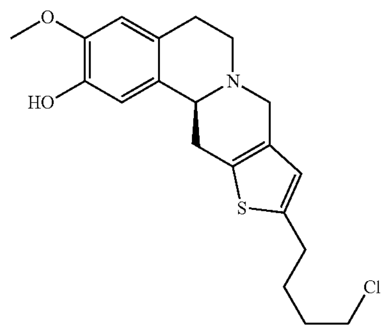 [SMILES: COc1cc2c(cc1O)[C@@H]1Cc3sc(CCCCCl)cc3CN1CC2] |
| DS017 | (S)-2-hydroxy-3-methoxy-10-(2,2,2-trifluoroethyl)-5,8,12,12a-tetrahydro-6H-benzo[a]thieno[3,2-g]quinolizine | 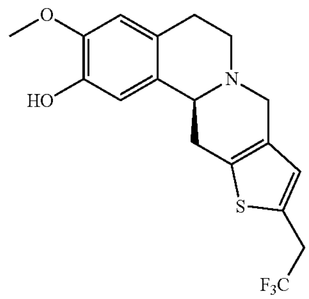 [SMILES: COc1cc2c(cc1O)[C@@H]1Cc3sc(CC(F)(F)F)cc3CN1CC2] |
| DS018 | (S)-2-hydroxy-3-methoxy-10-(3,3,3-trifluoropropyl)-5,8,12,12a-tetrahydro-6H-benzo[a]thieno[3,2-g]quinolizine | 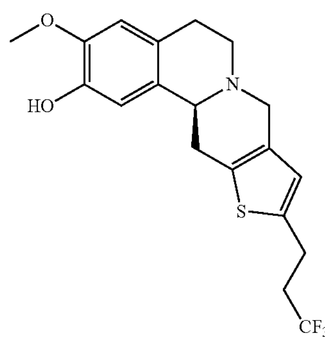 |
| DS019 | (S)-2-hydroxy-3-methoxy-10-(3,3-difluoropropyl)-5,8,12,12a-tetrahydro-6H-benzo[a]thieno[3,2-g]quinolizine | 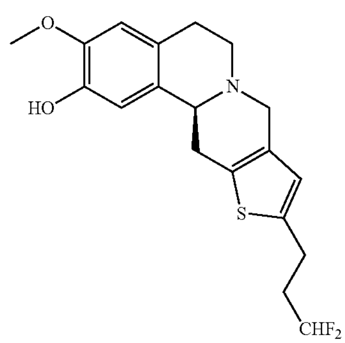 [SMILES: COc1cc2c(cc1O)[C@@H]1Cc3sc(CCC(F)F)cc3CN1CC2] |
| DS020 | (S)-2,3-dimethoxy-5,8,12,12a-tetrahydro-6H-benzo[a]thieno[3,2-g]quinolizine | 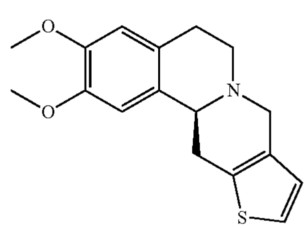 [SMILES: COc1cc2c(cc1OC)[C@@H]1Cc3sccc3CN1CC2] |

-continued

| No. | Name | Structure |
|---|---|---|
| DS021 | (S)-2,3-dimethoxy-10-ethyl-5,8,12,12a-tetrahydro-6H-benzo[a]thieno[3,2-g]quinolizine | 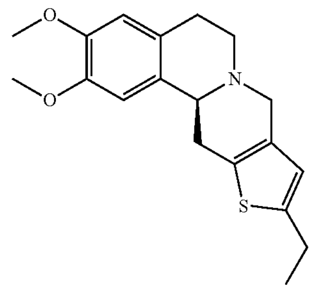 [SMILES: CCc1cc2c(s1)C[C@H]1c3cc(OC)c(OC)cc3CCN1C2] |
| DS022 | (S)-2,3-dimethoxy-10-(2-methylpropyl)-5,8,12,12a-tetrahydro-6H-benzo[a]thieno[3,2-g]quinolizine | 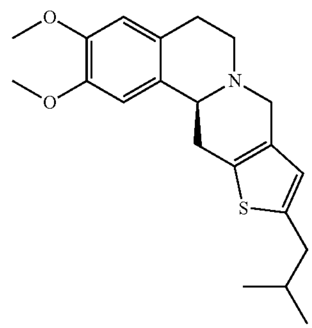 [SMILES: COc1cc2c(cc1OC)[C@@H]1Cc3sc(CC(C)C)cc3CN1CC2] |
| DS023 | (S)-2,3-dimethoxy-10-(2-chloroethyl)-5,8,12,12a-tetrahydro-6H-benzo[a]thieno[3,2-g]quinolizine | 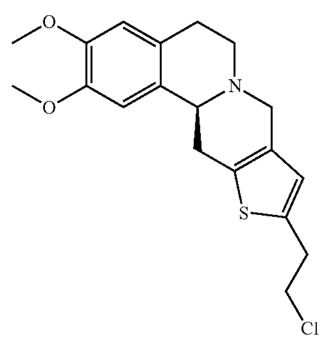 [SMILES: COc1cc2c(cc1OC)[C@@H]1Cc3sc(CCCl)cc3CN1CC2] |
| DS024 | (S)-2,3-methylenedioxo-5,8,12,12a-tetrahydro-6H-benzo[a]thieno[3,2-g]quinolizine | 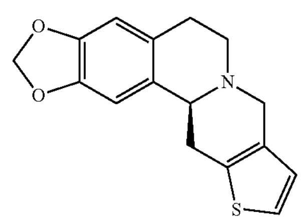 [SMILES: c1cc2c(s1)C[C@H]1c3cc4c(cc3CCN1C2)OCO4] |
| DS025 | (S)-2,3-methylenedioxo-10-ethyl-5,8,12,12a-tetrahydro-6H-benzo[a]thieno[3,2-g]quinolizine | 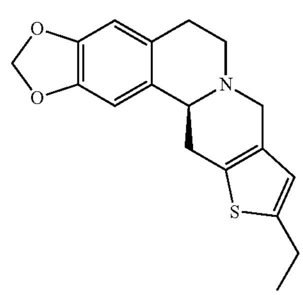 [SMILES: CCc1cc2c(s1)C[C@H]1c3cc4c(cc3CCN1C2)OCO4] |

| No. | Name | Structure |
|---|---|---|
| DS026 | (S)-2,3-methylenedioxo-10-(2-methylpropyl)-5,8,12,12a-tetrahydro-6H-benzo[a]thieno[3,2-g]quinolizine | 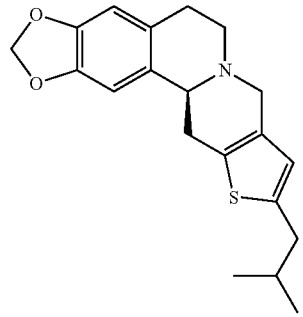 [SMILES: CC(C)Cc1cc2c(s1)C[C@H]1c3cc4c(cc3CCN1C2)OCO4] |
| DS027 | (S)-2,3-methylenedioxo-10-(2-chloroethyl)-5,8,12,12a-tetrahydro-6H-benzo[a]thieno[3,2-g]quinolizine | 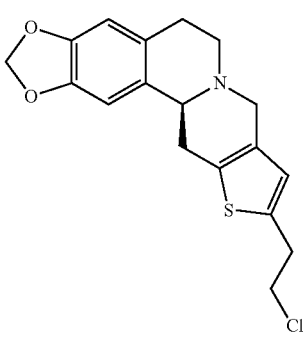 [SMILES: ClCCc1cc2c(s1)C[C@H]1c3cc4c(cc3CCN1C2)OCO4] |
| DS028 | (S)-2-hydroxy-3-methoxy-10-methyl-5,8,12,12a-tetrahydro-6H-benzo[a]thieno[3,2-g]quinolizine | 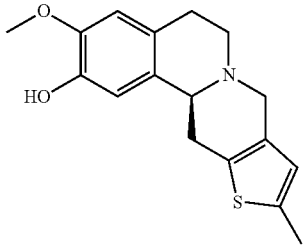 |
| DS029 | (S)-2-hydroxy-3-methoxy-10-(2-chloromethyl)-5,8,12,12a-tetrahydro-6H-benzo[a]thieno[3,2-g]quinolizine | 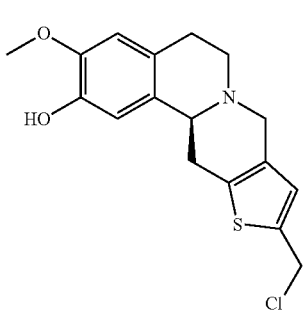 [SMILES: COc1cc2c(cc1O)[C@@H]1Cc3sc(CCl)cc3CN1CC2] |
| DS030 | (S)-2-hydroxy-3-methoxy-10-(2-fluoromethyl)-5,8,12,12a-tetrahydro-6H-benzo[a]thieno[3,2-g]quinolizine | 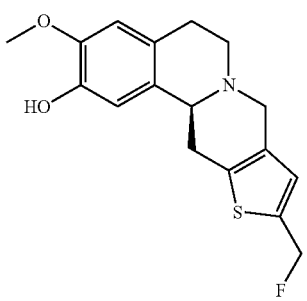 [SMILES: COc1cc2c(cc1O)[C@@H]1Cc3sc(CF)cc3CN1CC2] |

-continued

| No. | Name | Structure |
|---|---|---|
| DS031 | (S)-2-hydroxy-3-methoxy-10-hydroxymethyl-5,8,12,12a-tetrahydro-6H-benzo[a]thieno[3,2-g]quinolizine | 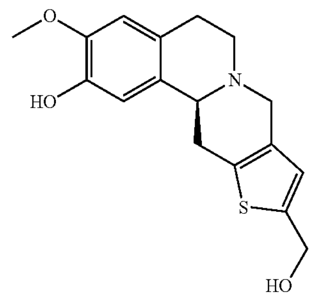 [SMILES: COc1cc2c(cc1O)[C@@H]1Cc3sc(CO)cc3CN1CC2] |
| DS032 | (S)-2-hydroxy-3-methoxy-10-methoxymethyl-5,8,12,12a-tetrahydro-6H-benzo[a]thieno[3,2-g]quinolizine | 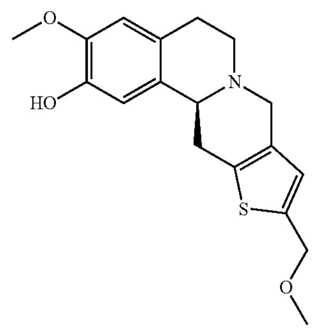 |
| DS033 | (S)-2-hydroxy-3,10-dimethoxy-5,8,12,12a-tetrahydro-6H-benzo[a]thieno[3,2-g]quinolizine | 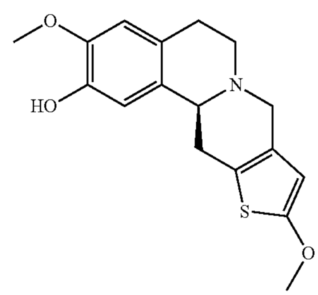 [SMILES: COc1cc2c(s1)C[C@H]1c3cc(O)c(OC)cc3CCN1C2] |
| DS034 | (S)-2-hydroxy-3-methoxy-9,10-dimethyl-5,8,12,12a-tetrahydro-6H-benzo[a]thieno[3,2-g]quinolizine | 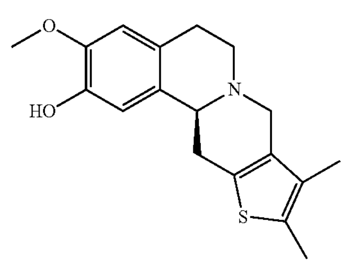 |
| DS035 | (S)-2-hydroxy-3-methoxy-9-methyl-5,8,12,12a-tetrahydro-6H-benzo[a]thieno[3,2-g]quinolizine | 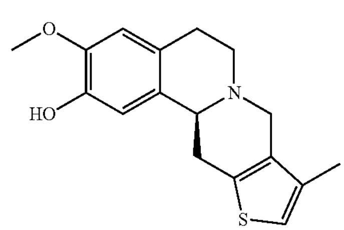 |

-continued

| No. | Name | Structure |
|---|---|---|
| DS036 | (S)-2-hydroxy-3-methoxy-9-ethyl-5,8,12,12a-tetrahydro-6H-benzo[a]thieno[3,2-g]quinolizine | 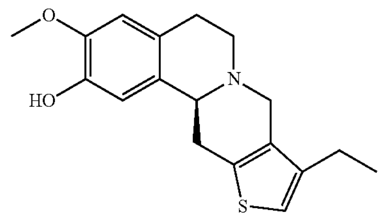 [SMILES: CCc1csc2c1CN1CCc3cc(OC)c(O)cc3[C@@H]1C2] |
| DS037 | (12aS)-2-hydroxy-3-methoxy-8-methyl-10-(2-methyl propyl)-5,8,12,12a-tetrahydro-6H-benzo[a]thieno[3,2-g]quinolizine | 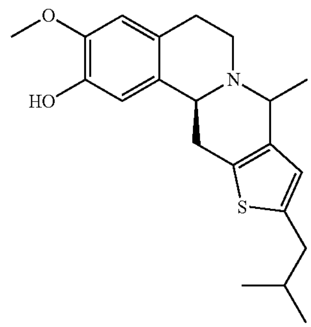 |
| DS038 | (12aS)-2-hydroxy-3-methoxy-5-methyl-10-(2-methyl propyl)-5,8,12,12a-tetrahydro-6H-benzo[a]thieno[3,2-g]quinolizine | 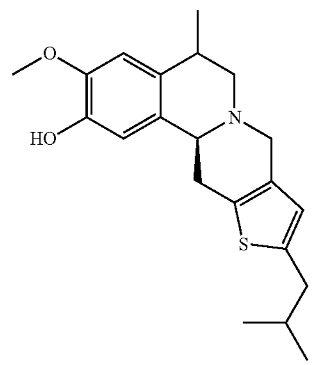 [SMILES: COc1cc2c(cc1O)[C@@H]1Cc3sc(CC(C)C)cc3CN1CC2C] |
| DS039 | (12aS)-2-hydroxy-3-methoxy-6-methyl-10-(2-methyl propyl)-5,8,12,12a-tetrahydro-6H-benzo[a]thieno[3,2--g]quinolizine | 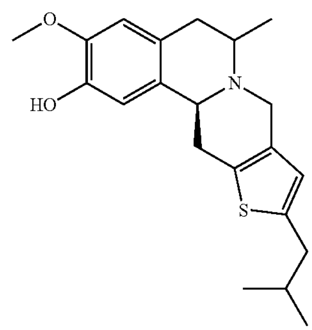 [SMILES: COc1cc2c(cc1O)[C@@H]1Cc3sc(CC(C)C)cc3CN1C(C)C2] |
| DS040 | (12aS)-2-hydroxy-3-methoxy-5-fluoro-10-(2-methylpropyl)-5,8,12,12a-tetrahydro-6H-benzo[a]thieno[3,2-g]quinolizine | 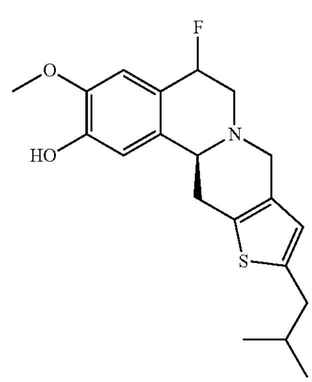 [SMILES: COc1cc2c(cc1O)[C@@H]1Cc3sc(CC(C)C)cc3CN1CC2F] |

| No. | Name | Structure |
| --- | --- | --- |
| DS041 | (S)-2-hydroxy-3-methoxy-10-ethyl-5,8,12,12a-tetrahydro-6H-benzo[a]thieno[2,3-g]quinolizine | 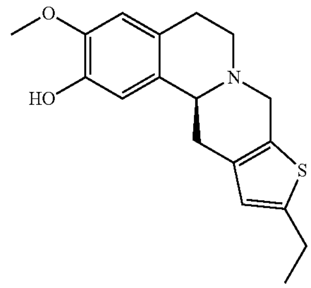 [SMILES: CCc1cc2c(s1)CN1CCc3cc(OC)c(O)cc3[C@@H]1C2] |
| DS042 | (S)-2-hydroxy-3-methoxy-10-(2-chloroethyl)-5,8,12,12a-tetrahydro-6H-benzo[a]thieno[2,3-g]quinolizine | 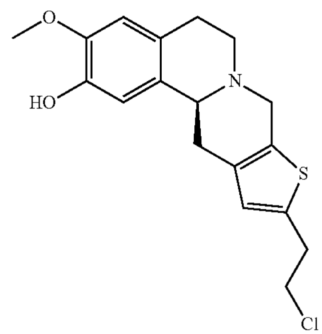 [SMILES: COc1cc2c(cc1O)[C@@H]1Cc3cc(CCCl)sc3CN1CC2] |
| DS043 | (S)-2-hydroxy-3-methoxy-10-(2-methylpropyl)-5,8,12,12a-tetrahydro-6H-benzo[a]thieno[2,3-g]quinolizine | 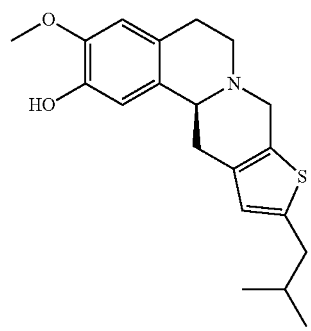 |
| DS044 | (S)-2-hydroxy-3,10-dimethoxy-5,8,12,12a-tetrahydro-6H-benzo[a]thieno[2,3-g]quinolizine | 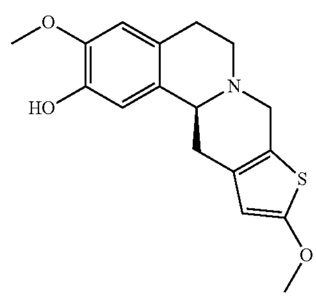 [SMILES: COc1cc2c(s1)CN1CCc3cc(OC)c(O)cc3[C@@H]1C2] |
| DF001 | (S)-2-hydroxy-3-methoxy-5,8,12,12a-tetrahydro-6H-benzo[a]furo[3,2-g]quinolizine | 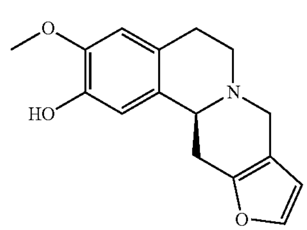 [SMILES: COc1cc2c(cc1O)[C@@H]1Cc3occc3CN1CC2] |

-continued

| No. | Name | Structure |
|---|---|---|
| DF002 | (S)-2-hydroxy-3-methoxy-10-ethyl-5,8,12,12a-tetrahydro-6H-benzo[a]furo[3,2-g]quinolizine | 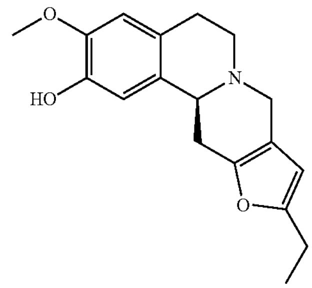 [SMILES: CCc1cc2c(o1)C[C@H]1c3cc(O)c(OC)cc3CCN1C2] |
| DF003 | (S)-2-hydroxy-3-methoxy-10-(2-methylpropyl)-5,8,12,12a-tetrahydro-6H-benzo[a]furo[3,2-g]quinolizine | 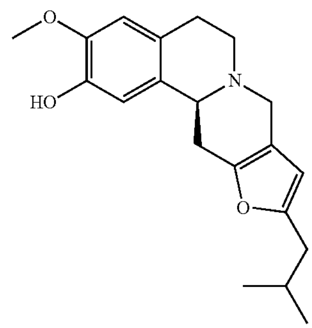 [SMILES: COc1cc2c(cc1O)[C@@H]1Cc3oc(CC(C)C)cc3CN1CC2] |
| DF004 | (S)-2-hydroxy-3-methoxy-10-chloropropylmethyl-5,8,12,12a-tetrahydro-6H-benzo[a]furo[3,2-g]quinolizine | 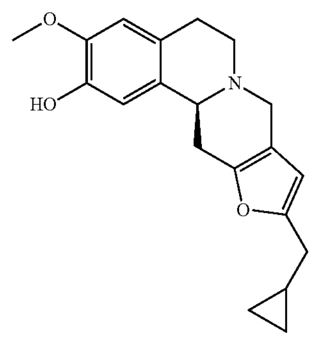 [SMILES: COc1cc2c(cc1O)[C@@H]1Cc3oc(CC4CC4)cc3CN1CC2] |
| DF005 | (S)-2-hydroxy-3-methoxy-10-(2-chloroethyl)-5,8,12,12a-tetrahydro-6H-benzo[a]furo[3,2-g]quinolizine | 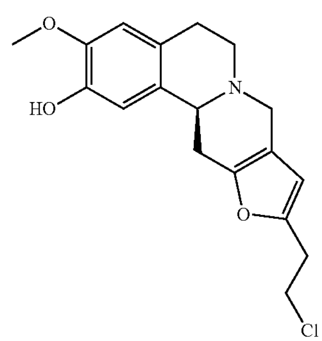 |
| DF006 | (S)-2-hydroxy-3,10-dimethoxy-5,8,12,12a-tetrahydro-6H-benzo[a]furo[3,2-g]quinolizine | 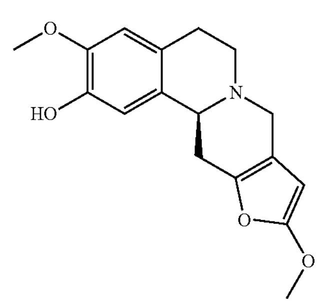 |

-continued

| No. | Name | Structure |
|---|---|---|
| DF007 | (S)-2-hydroxy-3-methoxy-10-ethyl-5,8,12,12a-tetrahydro-6H-benzo[a]furo[2,3-g]quinolizine | 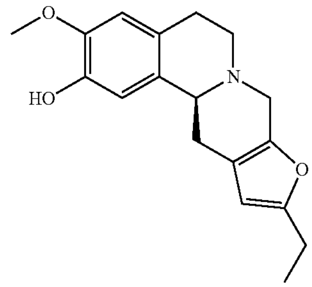 |
| DF008 | (S)-2-hydroxy-3-methoxy-10-(2-methylpropyl)-5,8,12,12a-tetrahydro-6H-benzo[a]furo[2,3-g]quinolizine | 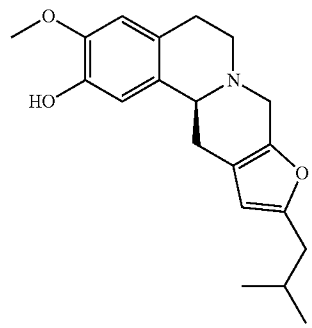 [SMILES: COc1cc2c(cc1O)[C@@H]1Cc3cc(CC(C)C)oc3CN1CC2] |
| DF009 | (S)-2-hydroxy-3-methoxy-10-(2-chloroethyl)-5,8,12,12a-tetrahydro-6H-benzo[a]furo[2,3-g]quinolizine | 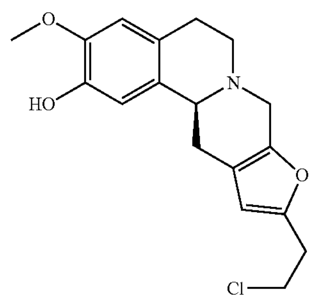 [SMILES: COc1cc2c(cc1O)[C@@H]1Cc3cc(CCCl)oc3CN1CC2] |
| DP001 | (S)-2-hydroxy-3-methoxy-5,8,12,12a-tetrahydro-6H-benzo[a]pyrrolo[3,2-g]quinolizine | 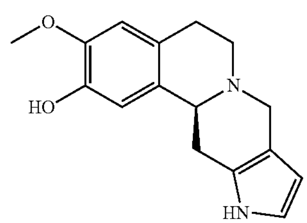 [SMILES: COc1cc2c(cc1O)[C@@H]1Cc3[nH]ccc3CN1CC2] |
| DP002 | (S)-2-hydroxy-3,10-dimethoxy-5,8,12,12a-tetrahydro-6H-benzo[a]pyrrolo[3,2-g]quinolizine | 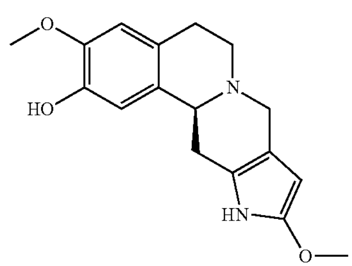 |

| No. | Name | Structure |
|---|---|---|
| DP003 | (S)-2-hydroxy-3,10-dimethoxy-5,8,12,12a-tetrahydro-6H-benzo[a]pyrrolo[2,3-g]quinolizine | 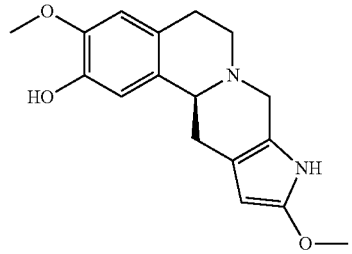 |
| DP004 | (S)-2-hydroxy-3-methoxy-5,8,13,13a-tetrahydro-6H-benzo[a]pyrido[3,2-g]quinolizine | 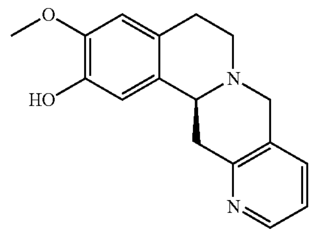 [SMILES: COc1cc2c(cc1O)[C@@H]1Cc3ncccc3CN1CC2] |
| DP005 | (S)-2,10-dihydroxy-3,9-dimethoxy-5,8,13,13a-tetrahydro-6H-benzo[a]pyrido[3,2-g]quinolizine | 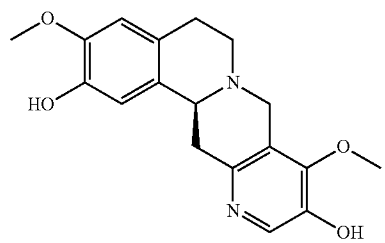 |
| DP006 | (S)-2-hydroxy-3,10-dimethoxy-5,8,13,13a-tetrahydro-6H-benzo[a]pyrido[2,3-g]quinolizine | 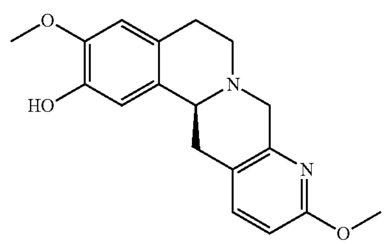 |
| SS001 | (S)-2-methyl-9-(2-methylpropyl)-4,7,11,11a-tetrahydro-5H-thieno[3,2-a]thieno[3,2-g]quinolizine | 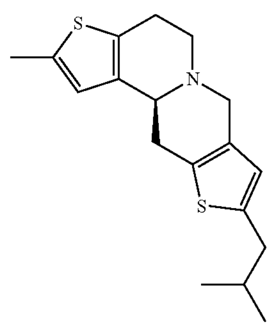 [SMILES: Cc1cc2c(s1)CCN1Cc3cc(CC(C)C)sc3C[C@@H]21] |
| SS002 | (S)-2-methyl-9-(2-chloroethyl)-4,7,11,11a-tetrahydro-5H-thieno[3,2-a]thieno[3,2-g]quinolizine | 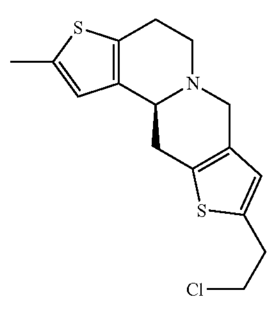 [SMILES: Cc1cc2c(s1)CCN1Cc3cc(CCCl)oc3C[C@@H]21] |

-continued
| No. | Name | Structure |
|---|---|---|
| SF001 | (S)-2-methyl-9-(2-chloroethyl)-4,7,11,11a-tetrahydro-5H-thieno[3,2-a]furo[3,2-g]quinolizine | 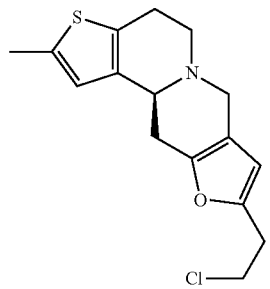 |
| FS001 | (S)-2-methyl-9-(2-chloroethyl)-4,7,11,11a-tetrahydro-5H-furo[3,2-a]thieno[3,2-g]quinolizine | 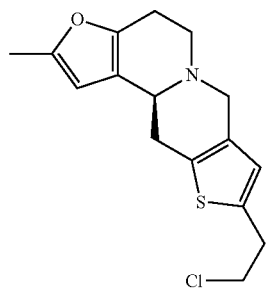 [SMILES: Cc1cc2c(o1)CCN1Cc3cc(CCCl)sc3C[C@@H]21] |
| IS001 | (S)-11-(2-methylpropyl)-6,9,13,13a-tetrahydro-7H-indolo[2,3-a]thieno[3,2-g]quinolizine | 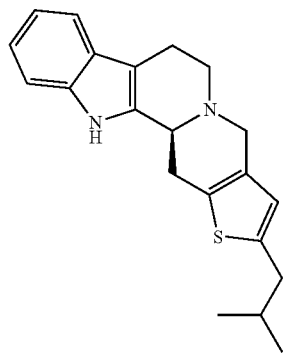 [SMILES: CC(C)Cc1cc2c(s1)C[C@H]1c3[nH]c4ccccc4c3CCN1C2] |
| IS002 | (S)-11-(2-chloroethyl)-6,9,13,13a-tetrahydro-7H-indolo[2,3-a]thieno[3,2-g]quinolizine | 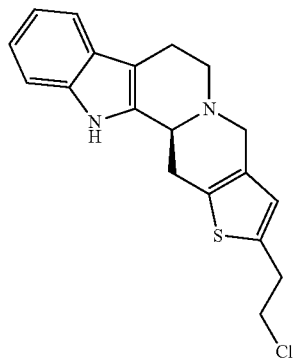 [SMILES: ClCCc1cc2c(s1)C[C@H]1c3[nH]c4ccccc4c3CCN1C2] |

-continued

| No. | Name | Structure |
|---|---|---|
| IS003 | (S)-3-methoxy-11-(2-methylpropyl)-6,9,13,13a-tetrahydro-7H-indolo[2,3-a]thieno[3,2-g]quinolizine | 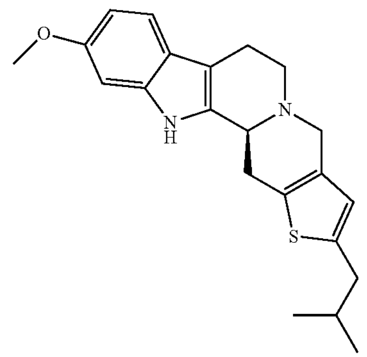 [SMILES: COc1ccc2c3c([nH]c2c1)[C@@H]1Cc2sc(CC(C)C)cc2CN1CC3] |
| IS004 | (S)-3-methoxy-11-(2-chloroethyl)-6,9,13,13a-tetrahydro-7H-indolo[2,3-a]thieno[3,2-g]quinolizine | 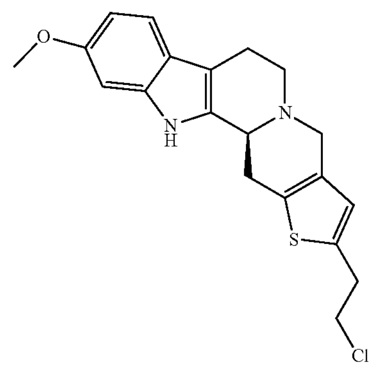 [SMILES: COc1ccc2c3c([nH]c2c1)[C@@H]1Cc2sc(CCCl)cc2CN1CC3] |
| DS045 | (S)-2-hydroxy-3-methoxy-10-(2'-hydroxyethoxymethyl)-5,8,12,12a-tetrahydro-6H-benzo[a]thieno[3,2-g]quinolizine | 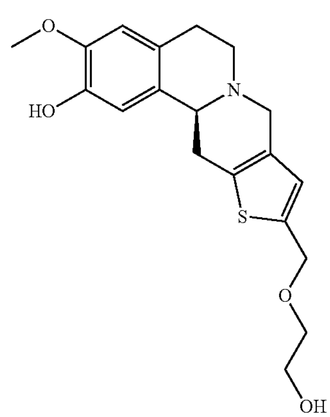 [SMILES: COc1cc2c(cc1O)[C@@H]1Cc3sc(COCCO)cc3CN1CC2] |
| DS046 | (S)-2-hydroxy-3-methoxy-10-(dimethylaminomethyl)-5,8,12,12a-tetrahydro-6H-benzo[a]thieno[3,2-g]quinolizine | 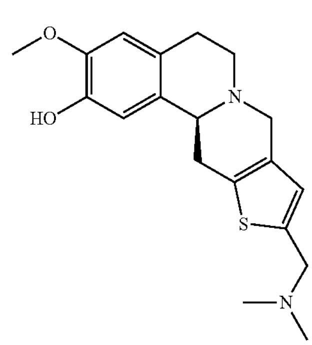 |

-continued

| No. | Name | Structure |
|---|---|---|
| DS047 | (S)-2-hydroxy-3-methoxy-10-(morpholine-N-methyl)-5,8,12,12a-tetrahydro-6H-benzo[a]thieno[3,2-g]quinolizine | 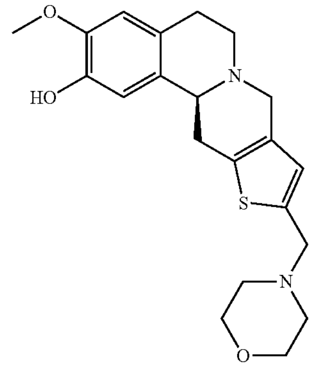 [SMILES: COc1cc2c(cc1O)[C@@H]1Cc3sc(CN4CCOCC4)cc3CN1CC2] |
| DS048 | (S)-2-hydroxy-3-methoxy-10-((N-methyl)-piperazine-N-methyl)-5,8,12,12a-tetrahydro-6H-benzo[a]thieno[3,2-g]quinolizine | 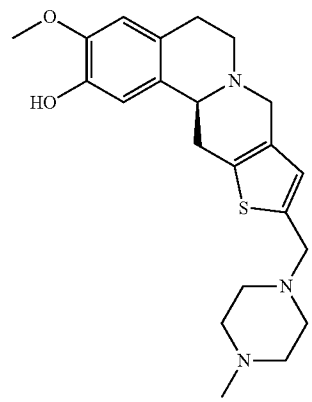 [SMILES: COc1cc2c(cc1O)[C@@H]1Cc3sc(CN4CCN(C)CC4)cc3CN1CC2] |
| DS049 | (S)-2-hydroxy-3-methoxy-5,8,12,12a-tetrahydro-6H-benzo[a]thieno[3,2-g]quinolizine-10-(N,N-dimethyl)acetamide | 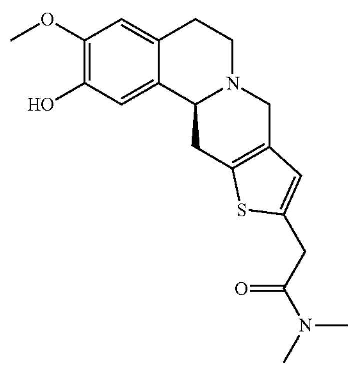 |
| DS050 | (S)-2-hydroxy-3-methoxy-5,8,12,12a-tetrahydro-6H-benzo[a]thieno[3,2-g]quinolizine-10-acetic acid | 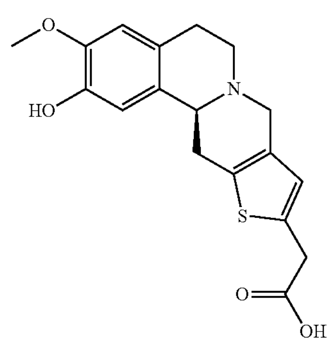 [SMILES: COc1cc2c(cc1O)[C@@H]1Cc3sc(CC(=O)O)cc3CN1CC2] |

| No. | Name | Structure |
|---|---|---|
| DS051 | (S)-2-hydroxy-3-methoxy-10-(hydroxyethyl)-5,8,12,12a-tetrahydro-6H-benzo[a]thieno[3,2-g]quinolizine | 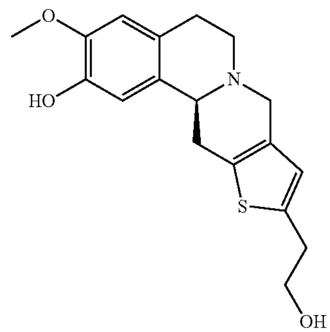 [SMILES: COc1cc2c(cc1O)[C@@H]1Cc3sc(CCO)cc3CN1CC2] |
| DS052 | methyl(S)-2-hydroxy-3-methoxy-5,8,12,12a-tetrahydro-6H-benzo[a]thieno[3,2-g]quinolizine-10-acetate | 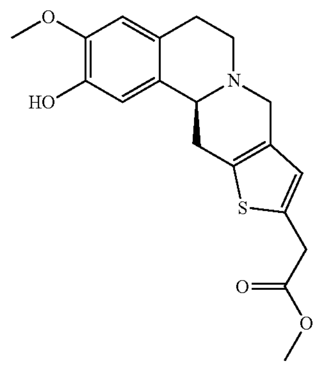 [SMILES: COC(=O)Cc1cc2c(s1)C[C@H]1c3cc(O)c(OC)cc3CCN1C2] |
| SBE01 | (S)-4,7,12,12a-tetrahydro-5H-thieno[3,2-a]benzooxazolo[6,5-g]quinolizine | 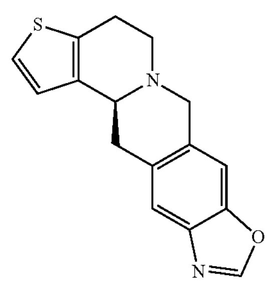 [SMILES: c1nc2cc3c(cc2o1)CN1CCc2sccc2[C@@H]1C3] |
| FBS01 | (S)-11-(2-methylpropyl)-6,9,13,13a-tetrahydro-7H-benzofuro[6,5-a]thieno[3,2-g]quinolizine | 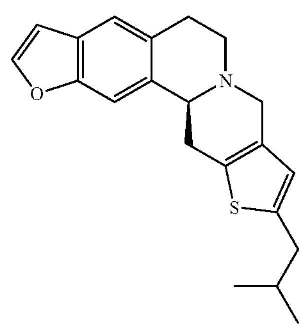 [SMILES: CC(C)Cc1cc2c(s1)C[C@H]1c3cc4occc4cc3CCN1C2] |

The "pharmaceutically acceptable salt" is a conventional non-toxic salt formed by reacting the compound of formula (I) with an inorganic or organic acid. For example, a conventional non-toxic salt may be a salt prepared by reacting the compound of formula (I) with an inorganic acid including HCl, hydrobromic acid, sulfuric acid, nitric acid, aminosulfonic acid, phosphoric acid, and the like, or an organic acid including citric acid, tartaric acid, lactic acid, pyruvic acid, acetic acid, benzenesulfonic acid, p-toluenesulfonic acid, methanesulfonic acid, naphthalene sulfonic acid, ethanesulfonic acid, naphthalenedisulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, sulfanilic acid, 2-acetoxybenzoic acid, isethionic acid and the like; or, a sodium salt, potassium salt, calcium salt, aluminum salt or ammonium salt form with an inorganic base after reacting the compound of formula (I) with propionic acid, oxalic acid, malonic acid, succinic acid, maleic acid, lactic acid, malic acid, tartaric acid, citric acid, aspartic acid or glutamic acid to form an ester; or, a methylamine salt, ethylamine salt or ethanolamine salt formed by the compound of formula (I) with an organic base; or, an inorganic acid salt formed with HCl, hydrobromic acid, hydrofluoric acid, sulfuric acid, nitric acid, or phosphoric acid, or an organic acid salt formed with formic acid, acetic acid, picric acid, methanesulfonic acid or ethanesulfonic acid, after reacting the compound of formula (I) with lysine, arginine, ornithine to form an ester.

The present invention also provides a process for preparing the compound of formula (I). Unless otherwise stated, the raw materials and reagents used in the present invention are commercially available.

Another object of the present invention is to provide a process for preparing the diarylo[a,g]quinolizine compound of formula (I), enantiomer, diastereoisomer, racemate and mixture thereof, pharmaceutically acceptable salt thereof, crystalline hydrate or solvate thereof, which is carried out as one of the following methods:

Method A:

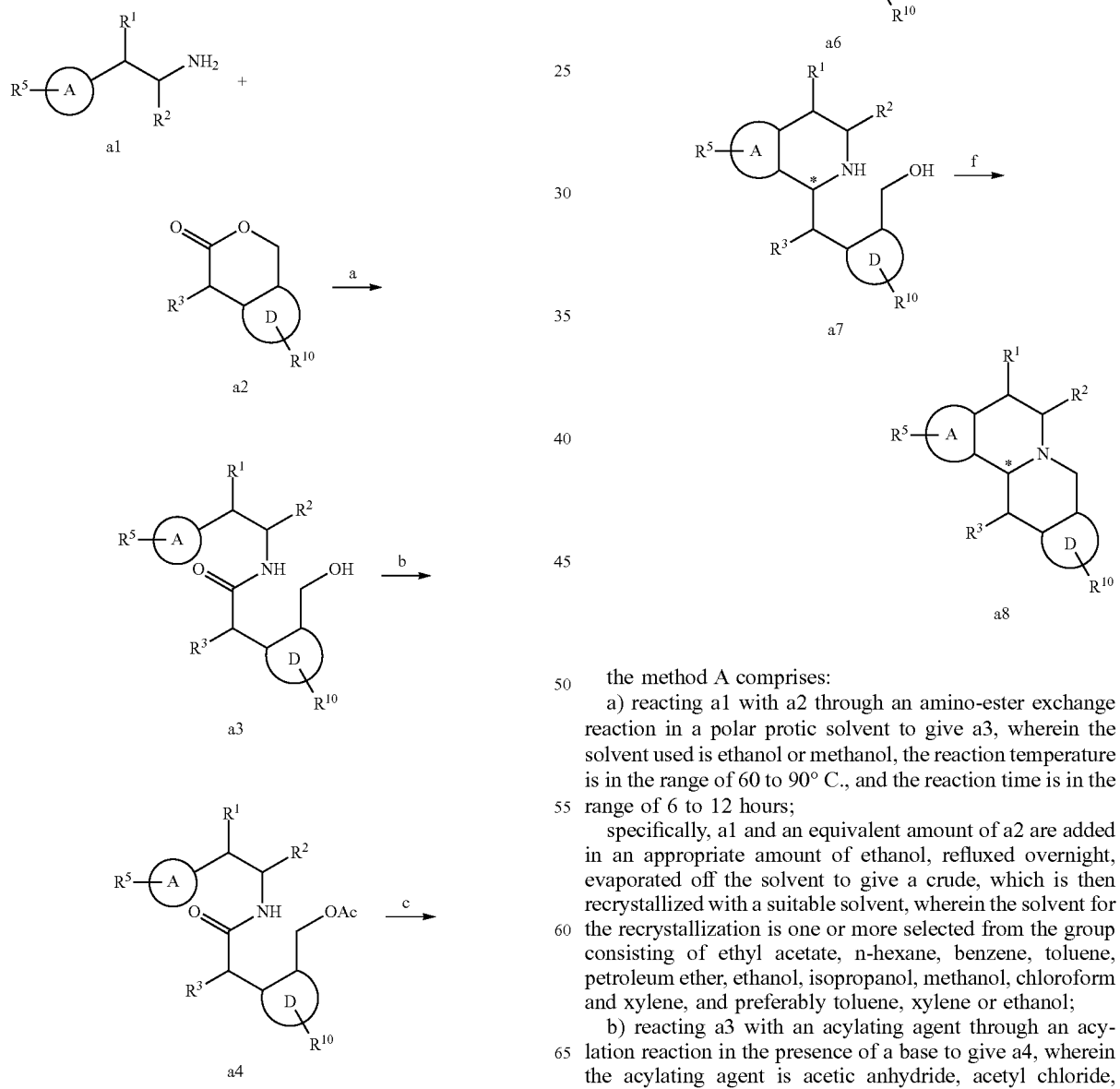

the method A comprises:

a) reacting a1 with a2 through an amino-ester exchange reaction in a polar protic solvent to give a3, wherein the solvent used is ethanol or methanol, the reaction temperature is in the range of 60 to 90° C., and the reaction time is in the range of 6 to 12 hours;

specifically, a1 and an equivalent amount of a2 are added in an appropriate amount of ethanol, refluxed overnight, evaporated off the solvent to give a crude, which is then recrystallized with a suitable solvent, wherein the solvent for the recrystallization is one or more selected from the group consisting of ethyl acetate, n-hexane, benzene, toluene, petroleum ether, ethanol, isopropanol, methanol, chloroform and xylene, and preferably toluene, xylene or ethanol;

b) reacting a3 with an acylating agent through an acylation reaction in the presence of a base to give a4, wherein the acylating agent is acetic anhydride, acetyl chloride, trifluoroacetic anhydride, trichloroacetic anhydride, methyl chloroformate, ethyl chlorformate, or the like, preferably acetic anhydride or acetyl chloride; the base may be an inorganic or organic base, wherein the organic base may be, for example, triethylamine, diisopropylethylamine, pyridine, N,N-dimethylaniline, N,N-dimethylpyridine, or the like, preferably triethylamine, pyridine or diisopropylethylamine, and the inorganic base may be, for example, $K_2CO_3$, $Na_2CO_3$, $NaHCO_3$, $KHCO_3$, NaOH, KOH or the like; and the reaction solvent used is dichloromethane, tetrahydrofuran, ethyl ether, toluene or the like;

specifically, a3 is dissolved in a suitable solvent and an organic or inorganic base is added therein, and an acylating agent is added slowly at 0° C., the reaction continues for one hour at room temperature, an appropriate amount of water is added, and the reaction mixture is extracted with dichloromethane three times. The dichloromethane layer was washed with water, dried over sodium sulfate, evaporated to dryness. The obtained product is directly used in the next reaction step without purification;

c) dehydrating and cyclizing a4 in the presence of a condensing agent to give a5, wherein the reaction solvent used is anhydrous acetonitrile, anhydrous toluene or benzene, or the like, preferably anhydrous acetonitrile; The condensing agent used for the reaction is phosphorus oxychloride, phosphorus oxytribromide, phosphorus pentoxide or the like, preferably phosphorus oxytrichloride;

specifically, a4 is dissolved in an appropriate amount of a suitable solvent and heated to reflux, 2-3 equivalents of a condensing agent was added into the reaction mixture, and the completion of the reaction was monitored with TLC. Most of the solvent was distilled off, and the reaction mixture was neutralized with $NaHCO_3$ solution, extracted three times with dichloromethane, dried over sodium sulfate, and evaporated to dryness. The obtained product was directly used in the next reaction without purification;

d) asymmetrically reducing a5 in the presence of a hydrogenation reagent and a chiral catalyst to give a6, wherein the chiral catalyst may be Noyori catalyst, and the hydrogenation agent may be formic acid/triethylamine;

specifically, the imine a5 obtained as above is asymmetrically reduced in anhydrous N,N-dimethylformamide as the solvent in the presence of Noyori catalyst, triethylamine and formic acid to give a chiral amine a6, the reaction is carried out at room temperature for 7 hours to 12 hours; and after the completion of the reaction, the reaction mixture is neutralized with an aqueous saturated $NaHCO_3$ solution, extracted with ethyl acetate, and dried over sodium sulfate. In addition, non-chiral reduction may also be carried out by using sodium borohydride, sodium cyanoborohydride, sodium acetoxyborohydride;

e) hydrolyzing a6 in the presence of a base to give a7, wherein the base may be an inorganic base, which may be NaOH, KOH, CeOH, or $K_2CO_3$, preferably NaOH; the reaction solvent used may be a mixture of ethanol, methanol or N,N-dimethylformamide with water, preferably a mixture of ethanol or methanol with water;

specifically, a6 is dissolved in a suitable solvent, added with an appropriate amount of an inorganic base, and reacted for 3 hours at room temperature, and then an appropriate amount of water is slowly added to precipitate a solid, which is filtered off and dried to give a7;

f) halogenating a7 with a halogenating reagent and then directly cyclizing it in the presence of a base to give a8, wherein the halogenating agent is chlorosulfoxide, bromosulfoxide, phosphorus trichloride, phosphorus tribromide, phosphorus pentachloride, phosphorus pentabromide, or the like, the reaction solvent used is dichloromethane, tetrahydrofuran, ethylether, chloroform or the like, and the base is an organic or inorganic base, wherein the organic base is triethylamine, pyridine or diisopropylethylamine, the inorganic base is $K_2CO_3$, $Na_2CO_3$, $NaHCO_3$, $KHCO_3$, NaOH, KOH, $CaCO_3$ or ammonia, or the like;

specifically, a7 is dissolved in a suitable solvent with stirring at room temperature, a halogenating reagent is slowly added dropwise under an ice-bath, and after the addition is completed, the reaction is carried out for 2 hours at room temperature. An alkaline solution is slowly added to the reaction mixture so as to adjust pH to be alkali. The reaction is then stirred for 2 hours at room temperature. After the reaction is completed, the obtained product is extracted, washed and dried, and purified by passing through a silica column to give a8.

g) optionally, when a8 has a protective group to be removed, a8 is deprotected to remove the protective group;

Specifically, a8 is dissolved in ethanol and refluxed after the addition of a concentrated HCl, or refluxed at a low temperature with $BCL_3$ and dichloromethane, so as to be deprotected to give the desired compound.

Method B:

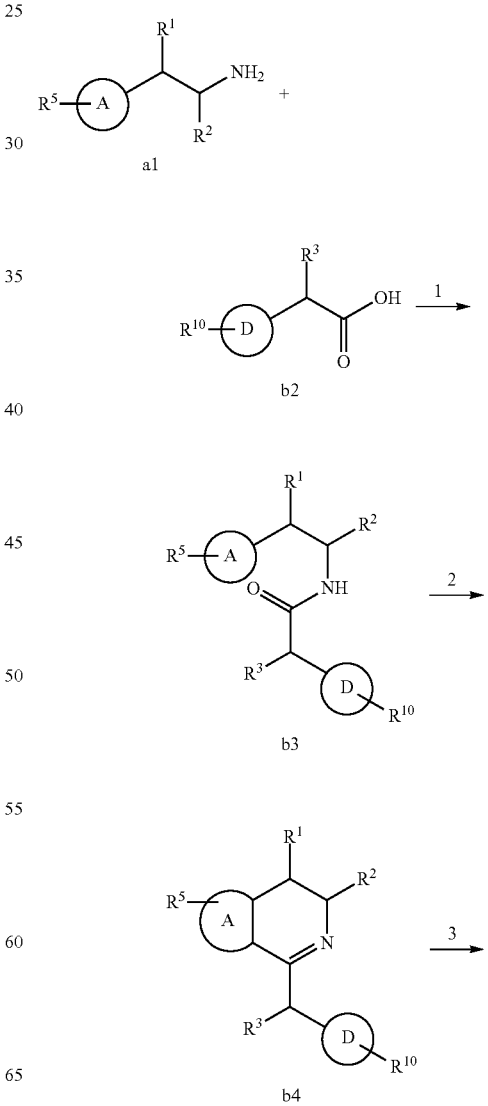

-continued

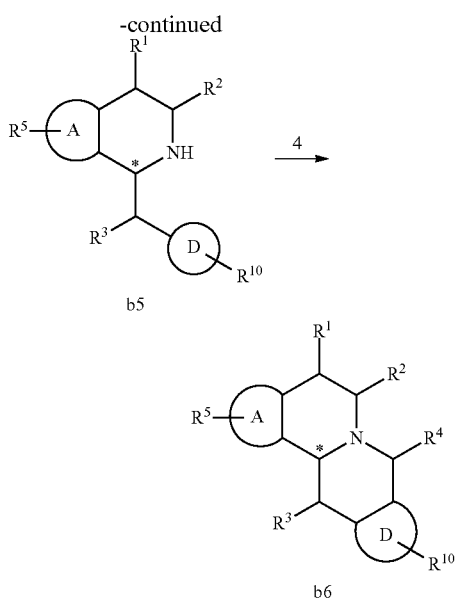

the method B comprises:

1) reacting a1 with b2 by a condensation reaction in the presence of a condensing agent to give b3;

specifically, b3 is prepared by condensing a1 (which is from Route A-1 or A-2, or purchased commercially) with an equivalent amount of b2 (which is from Route B-1 or B-2 or purchased commercially) in the presence of 1-ethyl-3(3-dimethylpropylamine)carbodiimide, triethylamine and anhydrous dichloromethane at room temperature and purifying the resultant product through column chromatography or recrystallization with ethanol;

2) dehydrating and cyclizing b3 in the presence of a condensing agent to give b4, which is similar to step c) of the method A;

3) asymmetrically reducing b4 in the presence of a chiral catalyst and a hydrogenation reagent to give b5, which is similar to step d) of the method A; and 4) reacting b5 with a substituted aldehyde $R^4$CHO through a Pictet-Spengler reaction under an acidic condition to give b6;

specifically, b5 is reacted with a substituted aldehyde $R^4$CHO under an acidic condition, wherein in the case that the used acid is HCl, the reaction is carried out under a pH of 2-3 for 2-3 days, and in the case that the used acid is formic acid, the reaction system is heated to 80-90° C. and kept for 2 hours. Then the reaction mixture is adjusted to be basic, and extracted with an organic solvent to obtain the desired compound;

wherein, in step 1), the solvent used is dichloromethane, tetrahydrofuran, ethyl ether, chloroform, or the like, the reaction temperature is room temperature, the reaction time is in the range of 2-10 hours, and the condensing agent for the reaction is 1-ethyl-3-(3-dimethylaminopropyl)carbodiimide;

in step 2), the solvent used is anhydrous acetonitrile, anhydrous toluene, benzene, or the like, preferably anhydrous acetonitrile; the condensing agent for the reaction is phosphorus oxychloride, phosphorus oxytribromide, phosphorus pentoxide, or the like, preferably phosphorus oxytrichloride, the reaction is performed under refluxing, and the reaction time is in a range of 20 minutes to 1 hour;

in step 3), the asymmetric reduction is carried out in the presence of anhydrous N,N-dimethylformamide as the solvent, Noyori catalyst, triethylamine and formic acid; and the reaction is carried out at room temperature for 7-12 hours, in the above methods A and B, rings A and D as well as the substituents are defined the same as those in formula (I).

In the above methods A and B, a1, a2 and b2 as starting materials are commercially available or may be prepared by conventional reactions.

Synthetic routes of the specific compounds and the reaction conditions are as follows.

AS001-A5030, AS038-AS053, AF001-AF019, AI002-A1007 and AP001-AP006 may be prepared according to the method A, wherein, in the method A for AS001-AS030, AS038-AS044, AS047-AS053, AF001-AF006, A1002-A1007 and AP004-AP006, a1 and a2 as starting materials may be purchased commercially or prepared according to the conventional methods in the art, for example, the following Route A-1.

Further, in the method A for AS045-AS046, AF007-AF009 and AP001-AP003, a1 as a starting material may be commercially available or prepared according to conventional methods in the art, for example, the following Route A-2; and in the method A, a2 as a starting material may be prepared according to the same route as Route A-1.

Route A-1:

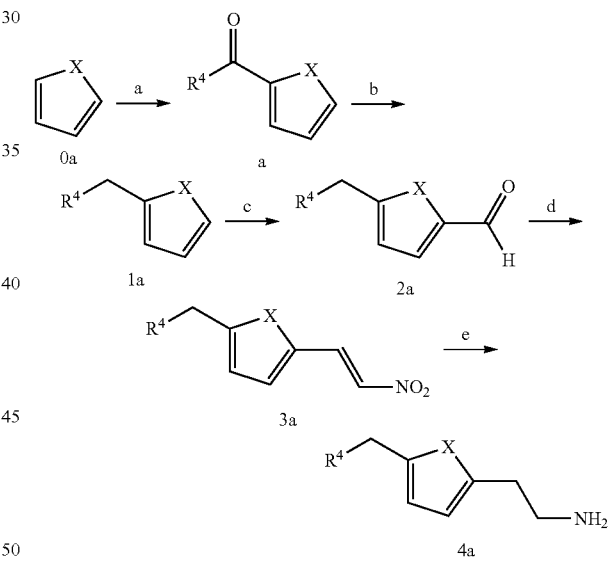

Step a:

a is prepared through a F—C acylation reaction of a heterocyclic compound 0a with $R_4$COCl under a Lewis acid;

specifically, the heterocyclic compound (commercially available) and $R_4$COCl are dissolved in anhydrous dichloromethane under an ice bath, and anhydrous $AlCl_3$ is slowly added thereto. The reaction mixture is kept at 0° C. to room temperature for 1-2 hours, treated with 1N HCl under stirring, and extracted with dichloromethane to give a;

Step b: the compound 1a is prepared by reducing a in the presence of a reductant and an acidic solvent;

specifically, the compound a is dissolved in trifluoroacetic acid at 0° C., added with an excess of triethyl silane, and stirred overnight at room temperature. The obtained product is purified by column chromatography to give 1a;

Step c: 2a is prepared by a substitution reaction of 1a in the presence of a Lewis acid and dichloromethyl ether;

specifically, 1a is dissolved in dry dichloromethane at 0° C., added slowly with titanium tetrachloride and dichloromethyl ether respectively, kept at 0° C. to room temperature for 1-2 hours, added with with ice water under stirring, and extracted with dichloromethane to give 2a;

Step d: 3a is prepared through a condensation reaction of 2a with nitromethane, and may be directly used for the next step without purification;

specifically, 2a is dissolved in an appropriate amount of glacial acetic acid, and added with 1.2 to 2.0 equivalents of ammonium acetate, followed by addition of 5-10 equivalents of nitromethane at room temperature. The reaction mixture is moved in an oil bath and kept at 80° C. for 10 hours, and then cooled at room temperature to precipitate a large amount of solid, which is filtered off to give 3a;

Step e: 4a is prepared by reducing 3a in the presence of a reductant and a polar solvent;

specifically, lithium aluminum hydride is suspended in an appropriate amount of anhydrous tetrahydrofuran and placed in an ice water bath, and a solution of a unsaturated nitro compound in anhydrous tetrahydrofuran was slowly added dropwise thereinto. After the addition is completed, the reaction mixture is refluxed for 3 hours under an oil bath, cooled to room temperature, and then added slowly with a quantitative water and filtered to give a clear solution, which is dried over anhydrous sodium sulfate, and evaporated to dryness to give an oil 4a;

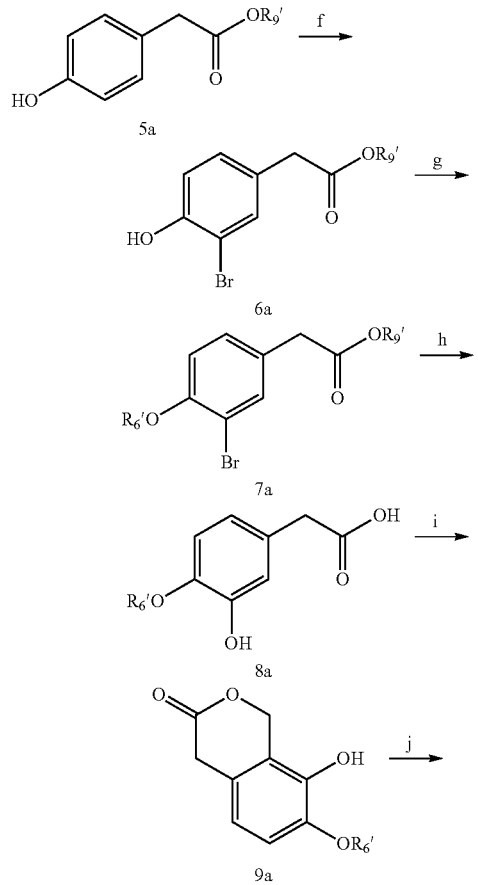

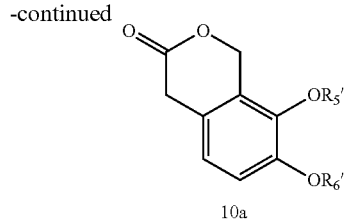

Step f: 6a is prepared through a substitution reaction of 5a with liquid bromine;

specifically, 5a (commercially available) is dissolved in acetic acid, and added slowly and dropwise with liquid bromine. The reaction is completed in 1-2 hours. The product has a poor solubility in acetic acid, and thus the post-treatment is simple, and it is relatively easy to obtain a relatively pure 6a;

Step g: 7a is prepared by a substitution reaction of the compound 6a in the presence of an alkylating agent or a benzylating agent;

specifically, 6a is reacted with an alkylating agent (e.g., dimethyl sulfate, methyl iodide, diazomethane, methyl trifluoromethylsulfonate, or other alkylating agents) or a benzylating reagent (e.g., substituted benzyl chloride, benzyl bromide and other benzylating reagents), preferably benzyl chloride, benzyl bromide, methyl iodide, dimethyl sulfate, acetyl chloride, acetic anhydride, in the presence of an organic or inorganic base to give 7a, wherein the solvent used may be one or more selected from the group consisting of methanol, ethanol, acetone, N,N-dimethylformamide, dimethylsulfoxide, tetrahydrofuran, dichloromethane, chloroform and dioxane, preferably acetone, tetrahydrofuran or N,N-dimethylformamide. The inorganic base may be one or more selected from the group consisting of NaOH, KOH, CeOH, Ba(OH)$_2$, KH, NaH, sodium tert-butoxide, potassium tert-butoxide, K$_2$CO$_3$, Na$_2$CO$_3$ and CaCO$_3$, and the organic base may be one or more selected from the group consisting of triethylamine, diisopropylethylamine, pyridine, N,N-dimethylaniline and N,N-dimethylpyridine, and preferably, K$_2$CO$_3$ is used.

Step h: 8a is prepared through a substitution reaction of 7a in the presence of a copper catalyst under an alkaline condition, optionally under microwave;

specifically, the copper catalyst may be one or two selected from the group consisting of copper sulphate, copper oxide, copper powder, copper chloride, copper bromide, copper iodide, copper carbonate, copper nitrate, copper hydroxide and the like, preferably one or two selected from the group consisting of copper sulfate, copper oxide, and copper powder; the reaction is carried out under an alkaline condition in the presence of a base such as NaOH, KOH, CeOH, Ca(OH)$_2$, Ba(OH)$_2$ or a quaternary ammonium base, preferably NaOH, KOH or CeOH; the reaction is optionally carried out under the assistance of microwave, the reaction temperature is in a range of 90° C.-150° C. The method is a very effective method for producing a phenolic hydroxy group. 8a having a relative high purity may be obtained by adjusting the pH value of the reaction mixture to 1-3 after the reaction. If further purification is necessary, one or two solvents selected from the group consisting of ethyl acetate, n-hexane, benzene, toluene, petroleum ether, ethanol, isopropanol, methanol, chloroform and xylene, preferably, toluene, xylene, and benzene may be used to perform a recrystallization.

Step i: 9a is prepared through a cyclization of 8a in the presence of formaldehyde, which may be performed by referring to Richard J. Spangler, Brian G. Beckmann, Jong Ho Kim, *J. Org Chem,* 1977, 42, 2989-2996, And Mark Cushman, Frederick W. Dekow, *J. Org Chem,* 1979, 44, 407-409;

specifically, 8a is refluxed in toluene with 2.0 to 3.0 equivalents of phenylboronic acid for 1 hour, added with paraformaldehyde and toluene, and kept at 100° C. for 46 hours. The reaction mixture is evaporated to dryness, reacted in water solution for 2 hours, and extracted with dichloromethane. The organic phase is dried over sodium sulfate, evaporated to dryness, stirred for three hours in diethyl ether and filtered to give 9a.

Step j: 10a is prepared by a substitution of 9a with an alkylating agent or a benzylating reagent;

specifically, 9a is reacted with an alkylating agent (e.g., dimethyl sulfate, methyl iodide, diazomethane, methyl trifluoromethylsulfonate, or other alkylating agents), an acylating agent (e.g., acetyl chloride, acetic anhydride, benzoyl chloride, trifluoroacetic anhydride, etc.), or a benzylating reagent (e.g., substituted benzyl chloride, benzyl bromide and other benzylating reagents), preferably benzyl chloride, benzyl bromide, methyl iodide, dimethyl sulfate, acetyl chloride, or acetic anhydride, in the presence of an organic or inorganic base to give 10a. The solvent used is one or more selected from the group consisting of methanol, ethanol, acetone, N,N-dimethylformamide, dimethylsulfoxide, tetrahydrofuran, dichloromethane, chloroform and dioxane, preferably acetone, tetrahydrofuran or N,N-dimethylformamide. The inorganic base is one or more selected from the group consisting of NaOH, KOH, CeOH, Ba(OH)$_2$, KH, NaH, sodium tert-butoxide, potassium tert-butoxide, K$_2$CO$_3$, Na$_2$CO$_3$ and CaCO$_3$, and the organic base is one or more selected from the group consisting of triethylamine, diisopropylethylamine, pyridine, N,N-dimethylaniline and N,N-dimethylpyridine, and preferably K$_2$CO$_3$ is used.

Route A-2:

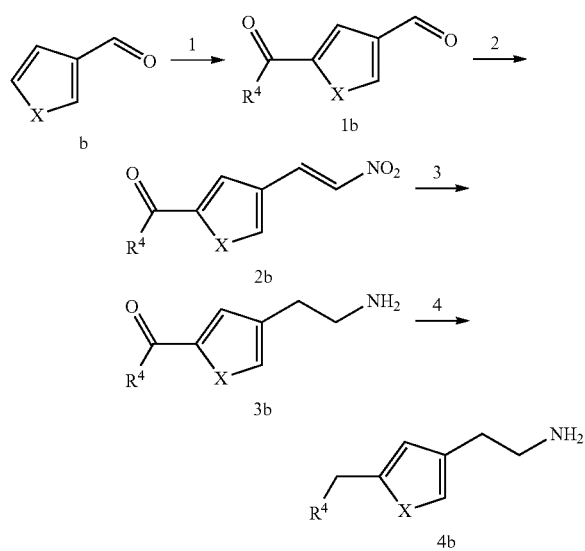

Step 1: 1b is prepared by a F—C acylation reaction of b with R$_4$COCl in the presence of a Lewis acid;

specifically, the heterocyclic compound b (commercially available) and R$_4$COCl are dissolved in anhydrous dichloromethane under an ice bath, added slowly with anhydrous AlCl$_3$, kept at 0° C. to room temperature for 1-2 hours, and then treated by 1N HCl with stirring, and extracted with dichloromethane to give 1b;

Step 2: 2b is prepared by condensing b with nitromethane.

specifically, 1b is dissolved in an appropriate amount of glacial acetic acid, and added with 1.2 to 2.0 equivalents of ammonium acetate, and then with 5-10 equivalents of nitromethane at room temperature. The reaction mixture is moved in an oil bath at 80° C. for 10 hours, cooled at room temperature to precipitate a large amount of solid, which is filtered to give 2b;

Step 3: 3b is prepared by reducing 2b in the presence of a reductant and a polar solvent;

specifically, lithium aluminum hydride is suspended in an appropriate amount of anhydrous tetrahydrofuran, placed in an ice water bath, and slowly and dropwisely added with a solution of the unsaturated nitro compound in anhydrous tetrahydrofuran. After the dropwise addition is completed, the reaction mixture is transferred in an oil bath and refluxed for 3 hours, cooled to room temperature, slowly added with a quantitative water, and filtered to give a clear solution, which is dried over anhydrous sodium sulfate and evaporated to dryness to give an oil 3b;

Step 4: the compound 4b is prepared by reducing the compound 3b under a reductant and an acidic solvent;

specifically, 3b is dissolved in trifluoroacetic acid at 0° C., added with an excess amount of triethylsilane and stirred at room temperature overnight. The obtained product is purified by column chromatography to give 4b.

In the above Routes A-1 and A-2, X is O, S or N; R4 is hydrogen, unsubstituted or halogen-substituted C1-C5 straight or branched alkyl, or unsubstituted or substituted benzyl. R9' is hydrogen, C1-C6 straight or branched alkyl, R5' is unsubstituted or halogen-substituted C1-C6 straight or branched alkyl, unsubstituted or substituted benzyl, R6' is unsubstituted or halogen-substituted C1-C6 straight or branched alkyl, unsubstituted or substituted benzyl, wherein the substituent for the substitution is C1-C6 straight or branched alkyl, halogen or C1-C6 straight or branched alkyloxy;

The aromatic ring suitable for the routes A-1 and A-2 may preferably be a benzene ring, thiophene, furan, indole, pyrrole, pyridine, or the like. In the reaction schemes, a 5-membered heterocycle is exemplified.

AS031-AS037, AI001, AI008-AI010, SBE01 and FBS01 may be prepared according to the method B.

DS001-DS052, DF001-DF009, DP001-DP006, SS001-SS002, SF001, FS001 and IS001-IS004 may be prepared according to Method B.

The starting material b2 for DS001-DS040, DS045-DS052, DF001-DF006, DP001-DP002, DP004-DP005, SS001-SS002, SF001, FS001, PP001-PP004 and IS001-IS004 can be purchased commercially or prepared by a conventional method, such as the following Route B-1.

Route B-1:

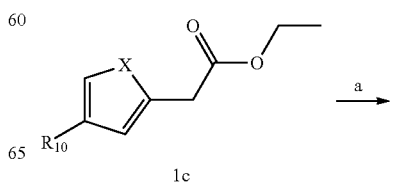

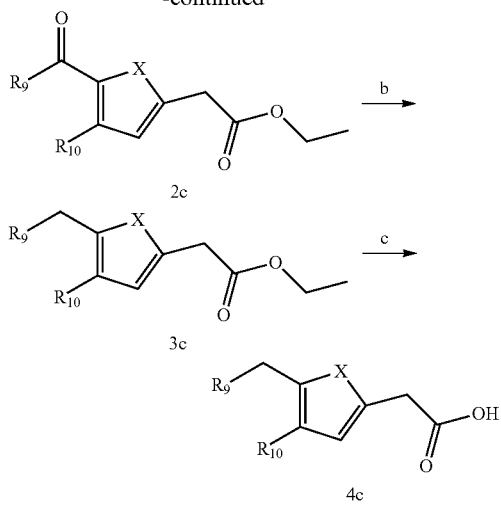

Step a: the step is the same as step a in Route A-1;

Step b: the step is the same as step b in Route A-1;

Step c: 4c is prepared by hydrolyzing 3c under a basic condition, wherein the base used is an inorganic base, which is one or more selected from the group consisting of NaOH, KOH, CeOH, Ba(OH)$_2$, KH, NaH, sodium t-butoxide, potassium t-butanol, K$_2$CO$_3$, Na$_2$CO$_3$ and CaCO$_3$ and the like;

Specifically, 3c is dissolved in an appropriate amount of ethanol, added with an appropriate amount of water and an inorganic base, stirred at room temperature for about 1 hour, adjusted pH with HCl, and extracted with dichloromethane to give a hydrolyzed product 4c.

Further, the starting material b2 for DS041-DS044, DF007-DF009, DP003, DP006, DI001-DI006, and SI001-SI004 may be commercially purchased or prepared by a conventional method, such as the following Route B-2.

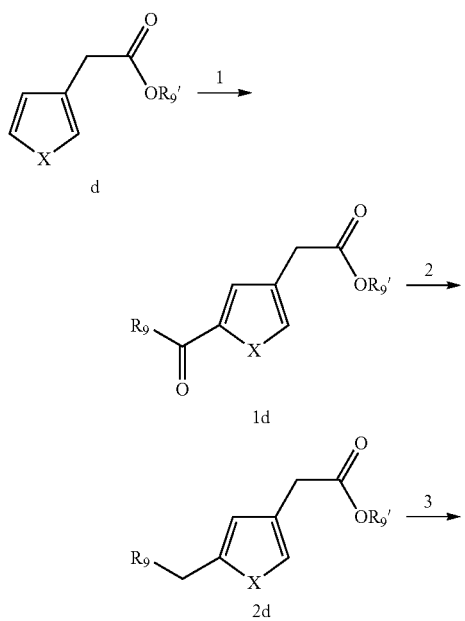

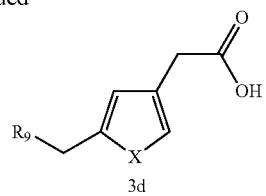

Step 1: the step is the same as step a in Route A-1;
Step 2: the step is the same as step b in Route A-1;
Step 3: the step is the same as step c in Route B-1;

wherein, X is O, S or N; R9 and R10 are each independently hydrogen, hydroxy, hydroxyl-substituted C1-C6 straight or branched alkyl, unsubstituted or halogen-substituted C1-C6 straight or branched alkyl, a unsubstituted or halogen-substituted C1-C6 straight or branched alkoxy, halogen, C3-C6 cycloalkyl, unsubstituted or halogen-substituted C2-C6 alkenyloxy, unsubstituted or halogen-substituted C3-C6 alkynyloxy, substituted or unsubstituted benzyl, substituted or unsubstituted C6-C20 aryl;

The aromatic ring suitable for the above Routes may preferably be benzene, thiophene, furan, pyrrole, pyridine and the like. In the reaction scheme, a 5-membered heterocycle is exemplified.

Furthermore, the present inventor found through experiments that the compound of formula (I) has excellent selectivity for D1 receptor and 5-HT receptor activity. The compound according to the present invention can be used in preparing an experimental model drug related to dopamine receptors and 5-HT receptors or in preparing a medicament for treating or preventing a disease related to dopamine receptors and 5-HT receptors. The disease related to dopamine receptors and 5-HT receptors may be a neurological disease such as schizophrenia, Parkinson's disease, mania, depression, drug addiction, migraine or the like.

The present invention also provides a pharmaceutical composition comprising a therapeutically effective amount of one or more selected from the group consisting of the compound of formula (I), enantiomers, diastereoisomers, racemates and mixtures thereof, and pharmaceutically acceptable salts, crystalline hydrates and solvates thereof, and one or more pharmaceutically acceptable carriers. The pharmaceutical composition may further contain one or more conventional additives such as an odor agent, a flavoring agent and the like.

The pharmaceutical composition of the present invention preferably contains 1-99%, more preferably 65%-99% by weight of the compound of formula (I) as an active ingredient, based on the total weight of the pharmaceutical composition, and the remaining amount of the pharmaceutically acceptable carriers and/or conventional additives.

The compound and the pharmaceutical composition of the invention may be provided in various preparations such as tablet, capsule, powder, syrup, solution, suspension, aerosol and the like, and may be present in a suitable solid or liquid carrier or diluent, or a suitable disinfection appliance for injection or infusion.

The pharmaceutical composition of the invention may be prepared in various dosage forms according to conventional preparation methods in the pharmaceutical art. It may contain 0.05-200 mg, preferably, 0.1 mg-100 mg of the compound of formula (I) per unit dosage in the formulation of the preparation.

The compound and pharmaceutical composition of the present invention may be clinically used in mammals, including humans and animals, and can be administered orally, nasally, transdermally, pulmonarily, or gastrointestinally. Oral administration is the most preferred. The most preferred daily dose is 0.01-200 mg/kg body weight and administered once daily, or 0.01-100 mg/kg body weight and administered several times a day. No matter what kind of administrating method is used, the optimal dose regimen for an individual should be based on the specific treatment Protocol. Generally, starting from a small dose, the dose is gradually increased until an optimal dose is achieved.

BEST MODE FOR CARRYING OUT THE INVENTION

The present invention will be further illustrated in the following examples. However, the following examples are merely provided for illustration, and the present invention is not limited to the following examples in any manner. Unless otherwise stated, all of the parameters and other description in the following examples are based on mass.

EXAMPLE 1

(S)-8-methoxy-9-hydroxy-4,7,12,12a-tetrahydro-5H-benzo[g]thieno[3,2-a]quinolizine (AS001)

1.1 Preparation of 2-(2-nitrovinyl)thiophene 1.5 g of 2-thienal was dissolved in 10 mL of glacial acetic acid, added with 2 equivalent of ammonium acetate, and then with 5 equivalent of nitromethane at room temperature. The mixture was placed in an oil bath at 80° C. and kept for 10 hours. TLC monitoring showed that the starting material disappeared. The reaction mixture was cooled to room temperature, distilled off most of the solvent, adjusted with saturated $NaHCO_3$ to be neutral, and extracted triply with dichloromethane. The organic phase was combined and distilled off the organic solvent. 1.89 g of yellow solid product was obtained by column chromatography. Yield, 91%.

$^1$H NMR ($CDCl_3$, 300 MHz): δ 8.15 (d, J=13.2 Hz, 1H), 7.84 (d, J=13.2 Hz, 1H,) 7.65 (d, J=4.2 Hz, 1H), 7.15 (dd, J=4.2 Hz, 3.8 Hz, 1H), 7.01 (d, J=4.2 Hz, J=3.8 Hz, 1H). ESI-MS m/z: 156.0 $[M+H]^+$.

1.2 Preparation of thiophene-2-ethylamine 1.89 g of 2-(2-nitrovinyl)thiophene was dissolved in anhydrous tetrahydrofuran, added with 4 equivalent of Lithium aluminum hydride in four batches under ice bath, and refluxed over night. The solvent was evaporated, and a small amount of water was added to extinct the reaction. The solid was removed by filtration, and washed with dichloromethane. The filtrate was dried over anhydrous sodium sulphate, and the solvent was evaporated to obtain 1.42 g of oily product. Yield, 92%.

$^1$H NMR ($CDCl_3$, 300 MHz): δ 7.24 (dd, 1H, J=5.1 and 1.3 Hz), 6.96 (dd, J=5.1 and 1.3 Hz, 1H), 6.89 (d, 1H, J=3.3 Hz), 3.09-3.23 (m, 4H). ESI-MS m/z: 128.2 $[M+H]^+$.

1.3 Preparation of methyl 3-bromo-4-hydroxyphenylacetate 4.88 g of methyl p-hydroxyphenylacetate was dissolved in acetic acid, and liquid bromine (1.1 eq) in acetic acid was dropwisely added in to the above solution. The reaction was preformed at room temperature and monitored by TLC. After the reaction was completed, saturated aqueous solution of $Na_2S_2O_3$ was added to remove excess $Br_2$, and then part of acetic acid was evaporated, and the solution was extracted several times until there was no product in aqueous phase. The organic phase was washed with saturated brine, dried over anhydrous sodium sulphate, and distilled off the solvent to give 6.3 g of white solid product. Yield, 88%.

$^1$H NMR ($CDCl_3$, 300 MHz): δ 7.39 (d, J=1.5 Hz, 1H), 7.11 (dd, J=8.4 Hz, J=1.5 Hz, 1H), 6.93 (d, J=8.4 Hz, 1H), 3.70 (s, 3H), 3.54 (s, 2H). ESI-MS m/z: 246.0 $[M+H]^+$.

1.4 Preparation of methyl 3-bromo-4-benzyloxyphenylacetate

Methyl 3-bromo-4-hydroxyphenylacetate and $K_2CO_3$ (1.5 eq) were dissolved in acetone, and BnBr (1.05 eq) was added thereto. The reaction was performed under refluxing and monitored by TLC. After the reaction was completed, the solid in the reaction solution was removed by filtration, and the solvent was evaporated off to give methyl 3-bromo-4-benzyloxyphenylacetate without further purification.

$^1$H NMR ($CDCl_3$, 300 MHz): δ 7.51-733 (m, 6H), 7.15 (dd, J=8.4 Hz, 1H), 6.89 (d, J=8.4 Hz, 1H), 5.15 (s, 2H), 3.70 (s, 3H), 3.55 (s, 2H). ESI-MS m/z: 336.1 [M+H]+.

1.5 Preparation of 3-hydroxy-4-benzyloxy phenylacetic acid

Methyl 3-bromo-4-benzyloxyphenylacetate (1.5 g), KOH (1.5 g), copper powder (0.15 g), and CuO powder (0.15 g) were dispersed in 8 mL of water, agitated at room temperature for 10 min, and degassed ultrasonically. The reaction was performed at 140° C. under microwave for 45 min. After the reaction was completed, Cu and CuO were removed by filtration, and pH was adjusted with concentrated HCl to be acidic to precipitate a white solid, which was filtered to give crude 3-hydroxy-4-benzyloxyphenylacetic acid. The solid was dissolved in methanol, added with an appropriate amount of active carbon, refluxed for 30 minutes and decolored. Purification by column chromatography gave a white solid. Yield, 56%.

$^1$H NMR ($CDCl_3$, 300 MHz): δ 7.43-7.38 (m, 5H), 6.90 (s, 11-1), 6.89 (dd, J=8.1 Hz, J=2.1 Hz, 1H), 6.74 (d, J=8.1 Hz, 1H), 5.10 (s, 2H), 3.56 (s, 2H). ESI-MS m/z: 273.2 $[M+H]^+$.

1.6 Preparation of 7-benzyloxy-8-hydroxy-3-isochromanone 3-hydroxy-4-benzyloxyphenylacetic acid (3.0 g) and phenylboronic acid (3.0 g) were dissolved in redistilled toluene (60 mL), and refluxed at 110° C. for 1 hour. The produced water was removed by an oil-water separation device. Paraformaldehyde (3 g) and an appropriate amount of molecular sieve (4 Å) were added into a pressure bottle, and the hot reaction mixture was poured into the pressure bottle. The reaction was performed at 100° C. for 46 hours. After the reaction was completed, the hot reaction mixture was filtered to remove the molecular sieve, and filtrate was evaporated to dryness to obtain a yellowish solid. 75 mL water was added thereto, and the reaction was performed under refluxing at 100° C. for 2 hours. After the reaction was completed, the reaction mixture was cooled to room temperature, and extracted with dichloromethane several times. The combined organic phase was washed with saturated brine, dried over anhydrous sodium sulphate, and distilled off the solvent to give a crude 7-benzyloxy-8-hydroxy-3-isochromanone.

The crude was added with 35 mL of anhydrous ethyl ether, agitated at room temperature for 3 hours and filtered to give the target product as a white solid.

$^1$H NMR (CDCl$_3$, 300 MHz): δ 7.45-7.34 (m, 5H), 6.93 (d, J=8.4 Hz, 1H), 6.86 (d, J=8.4 Hz, 1H), 5.40 (s, 1H), 5.12 (s, 1H), 3.91 (s, 3H), 3.62 (s, 2H). ESI-MS m/z: 271.1 [M−1-1]$^+$.

1.7 Preparation of 7-benzyloxy-8-methoxy-3-isochromanone 7-methoxy-8-hydroxy-3-isochromanone (1.5 g) and K$_2$CO$_3$(3 eq) were dissolved in acetone in a flask, added with CH$_3$I (3 eq), and heated under refluxing for 2 hours. TLC was used to monitor the reaction. After the reaction was completed, the solid in reaction mixture was removed by filtration, the filtrate was evaporated to dryness, and the residue was passed through a silica column to give 7-benzyloxy-8-methoxy-3-isochromanone.

$^1$H NMR (CDCl$_3$, 300 MHz): δ 7.45-7.34 (m, 5H), 6.92 (d, J=8.2 Hz, 1H), 6.85 (d, J=8.2 Hz, 1H), 5.40 (s, 2H), 5.12 (s, 2H), 3.91 (s, 3H), 3.62 (s, 2H). ESI-MS m/z: 285.1 [M+H]$^+$.

1.8 Preparation of N-(thiophene-2-ethyl)-2-hydroxy-3-methoxy-4-benzyloxyphenylace tamide 7-benzyloxy-8-methoxy-3-isochromanone and thiophene-2-ethylamine were dissolved in an appropriate amount of ethanol, and the mixture was agitated under refluxing overnight. The reaction was monitored by TLC. After the reaction was completed, the mixture was cooled, and evaporated to dryness, and the residue was passed through a silica column to give a white solid product. Yield, 84%.

$^1$H NMR (CDCl$_3$, 300 MHz): δ 7.45-7.25 (m, 6H), 6.82-6.85 (m, 2H), 6.75 (d, J=8.4 Hz, 1H), 6.64 (d, J=8.4, 1H), 5.12 (s, 2H), 4.65 (s, 2H), 3.79 (s, 3H), 3.60 (s, 2H), 3.39 (t, J=6.8 Hz, 2H), 2.65 (t, J=6.8 Hz, 2H). ESI-MS m/z: 412.1 [M+H]$^+$.

1.9 Preparation of N-(thiopheneethyl)-2-acetoxy-3-methoxy-4-benzyloxyphenylacetamide N-(thiopheneethyl)-2-hydroxy-3-methoxy-4-benzyloxyphenylacetamide was dissolved in a small amount of anhydrous dichloromethane, added with pyridine (3 eq) and a catalytic amount of DMAP, followed by dropwise addition of acetyl chloride in ice bath. After the addition, the ice bath was removed and the reaction was preformed at room temperature. After the reaction was completed, the reaction mixture was washed with 1 N HCl, and extracted. The organic phase was dried, evaporated to dryness. And the reissue was purified by column chromatography to give a white solid. Yield, 92%.

$^1$H NMR (CDCl$_3$, 300 MHz): δ 7.45-7.25 (m, 6H), 6.82-6.85 (m, 2H), 6.75 (d, J=8.4 Hz, 1H), 6.64 (d, J=8.4, 1H), 5.12 (s, 2H), 5.10 (s, 2H), 3.88 (s, 3H), 3.83 (s, 3H), 3.42 (t, J=7.0 Hz, 2H), 2.65 (t, J=7.0 Hz, 2H), 2.00 (s, 3H). ESI-MS m/z: 454.1 [M+H]$^+$.

1.10 Preparation of 2-methoxy-3-benzyloxy-6-((6,7-dihydro-thieno[3,2-c]pyridin-4-yl)-methyl)-benzyl acetate N-(thiopheneethyl)-2-acetoxy-3-methoxy-4-benzyloxyphenylacetamide (1.19 g) was dissolved in an appropriate amount of anhydrous acetonitrile and refluxed, followed by addition of POCl$_3$ (3 eq). The reaction was preformed under nitrogen for 0.5 hour and monitored by TLC. The reaction mixture was evaporated to dryness, and the residue was dissovled in a small amount of dichloromethane, added with saturated NaHCO$_3$ aqueous solution to be adjusted to be alkaline, and extracted triply with dichloromethane. The organic phase was washed with saturated brine, dried over sodium sulphate, and evaporated to dryness to give yellow oily crude without further purification.

ESI-MS m/z: 436.1 [M+H]$^+$.

1.11 Preparation of (S)-2-methoxy-3-benzyloxy-6-((4,5,6,7-tetrahydro-thieno(3,2-c)pyridin-4-yl)-methyl)-benzyl acetate The product (1.07 g) of last step was dissolved in a small amount of DMF (5 ml), added with a catalyst (R,R)-Noyori (0.02 eq), and then with a mixture of formic acid/triethanolamine (0.5 ml/0.2 ml/1 mmol raw material). The reaction was preformed at room temperature for about 8 hours. After the reaction was completed, the reaction mixture was added with saturated NaHCO$_3$ aqueous solution to be adjusted to be alkaline, added with a large amount of water, and extracted triply with ethyl acetate. The organic phase was washed with saturated brine, dried over anhydrous sodium sulphate and evaporated to dryness to give a dark green solid. In the case that (S,S)-Noyori was used to catalyze the reaction, a product in R-configuration was obtained.

ESI-MS m/z: 438.1 [M+H]$^+$.

1.12 Preparation of (S)-2-methoxy-3-benzyloxy-6-((4,5,6,7-tetrahydro-thieno(3,2-c)pyridin-4-yl)-methyl)-benzyl alcohol The product (1.21 g) of last step was dissolved in a mixture of ethanol (6 mL) and water (2 mL) and stirred at room temperature, followed by addition of NaOH (170 mg, 2 eq). The reaction was preformed for about 2 hours. After that, the reaction mixture was evaporated to remove part of the solvent, and extracted triply with dichloromethane. The organic phase was washed with saturated brine, dried over anhydrous sodium sulphate and evaporated to dryness to give a light green solid.

ESI-MS m/z: 396.1 [M+H]$^+$.

1.13 Preparation of (S)-4-(2-chloromethyl-3-methoxy-4-benzyloxy)-4,5,6,7-tetrahydro-thieno(3,2-c)pyridine The product (1.03 g) of last step was dissolved in redistilled dichloromethane (10 mL) an agitated at room temperature, followed by slow and dropwise addition of thionylchloride (4 eq). After addition, the reaction was preformed for 2 hours at room temperature.

ESI-MS m/z: 324.9 [M+H]$^+$.

1.14 Preparation of (S)-8-methoxy-9-benzyloxy-4,7,12,12a-tetrahydro-5H-benzo[g]thieno[3,2-a]quinolizine The reaction mixture of last step was added with saturated NaHCO$_3$ solution to adjust its pH to be alkaline, and stirred at room temperature for 2 hours. The reaction was monitored by TLC. After the reaction was completed, the reaction mixture was extracted triply with dichloromethane, and the organic phase was washed with saturated brine, dried over anhydrous sodium sulphate and evaporated to dryness. The residue was purified by column chromatography to give the target product.
$^1$H NMR (CDCl$_3$, 400 MHz): δ 7.5-7.28 (m, 5H), 7.21 (d, J=5.4 Hz, 1H), 6.88 (d, J=5.4 Hz, 1H), 6.64 (d, J=8.1, 1H), 6.58 (d, J=8.1, 1H), 5.00 (s, 2H), 4.16 (d, J=14.8 Hz, 1H), 3.83 (s, 3H), 3.56-3.45 (m, 2H), 3.25-3.10 (m, 3H), 2.88-2.80 (m, 1H), 2.69-2.60 (m, 2H). ESI-MS m/z: 378.1 [M+H]$^+$.

1.15 Preparation of (S)-8-methoxy-9-hydroxy-4,7,12,12a-tetrahydro-5H-benzo[g]thieno[3,2-a]quinolizine (AS001)

To (S)-8-methoxy-9-hydroxy-4,7,12,12a-tetrahydro-5H-benzo[g]thieno[3,2-a]quinolizine, were added ethanol (5 mL) and concentrated HCl (10 mL), and the mixture was refluxed at 90° C. for 2 hours. After the reaction was completed, the reaction mixture was evaporated to remove most of the HCl aqueous solution, neutralized with saturated NaHCO$_3$ aqeuous solution to be alkaline, and extracted several times with dichloromethane until there was no product in the aqueous phase. Purification by column chromatography gave the product AS001.
$^1$H NMR (CDCl$_3$, 400 MHz): δ 7.24 (d, J=5.4 Hz, 1H), 6.86 (d, J=5.4 Hz, 1H), 6.62 (d, J=8.1, 1H), 6.54 (d, J=8.1, 1H), 3.91 (d, J=14.8 Hz, 1H), 3.81 (s, 3H), 3.66 (dd, J=10.8 Hz, J=3.9 Hz, 1H), 3.53 (d, J=14.5 Hz, 1H), 3.27-3.21 (m, 1H), 3.14-3.04 (m, 2H), 2.82-2.70 (m, 3H). ESI-MS m/z: 288.0 [M+H]$^+$.

EXAMPLE 2

(R)-8-methoxy-9-hydroxy-4,7,12,12a-tetrahydro-5H-benzo[g]thieno[3,2-a]quinolizine (AS002)

The titled product was prepared by the same procedure as that in example 1, except that (S,S)-Noyori catalyst was used to replace (R,R)-Noyori.
$^1$H NMR (CDCl$_3$, 400 MHz): δ 7.21 (d, J=5.4 Hz, 1H), 6.85 (d, J=5.4 Hz, 1H), 6.62 (d, J=8.1, 1H), 6.55 (d, J=8.1, 1H), 3.92 (d, J=14.8 Hz, 1H), 3.83 (s, 3H), 3.68 (dd, J=10.8 Hz, J=3.8 Hz, 1H), 3.55 (d, J=14.5 Hz, 1H), 3.29-3.24 (m, 1H), 3.16-3.08 (m, 2H), 2.85-2.70 (m, 3H). ESI-MS m/z: 288.0 [M+H]$^+$.

EXAMPLE 3

(S)-2-methyl-8-methoxy-9-hydroxy-4,7,12,12a-tetrahydro-5H-benzo[g]thieno[3,2-a]quinolizine (AS003)

The titled product was prepared by the same procedure as that in example 1, except that 5-methylthiophene-2-aldehyde was used to replace thiophene-2-aldehyde.
$^1$H NMR (CDCl$_3$, 400 MHz): δ 6.65 (d, J=8.1, 1H), 6.54 (d, J=8.1, 1H), 6.14 (s, 1H), 3.95 (d, J=14.8 Hz, 1H), 3.83 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 3H), 2.37 (s, 3H). ESI-MS m/z: 302.0 [M+H]$^+$.

EXAMPLE 4

(R)-2-methyl-8-methoxy-9-hydroxy-4,7,12,12a-tetrahydro-5H-benzo[g]thieno[3,2-a]quinolizine (AS004)

The titled product was prepared by the same procedure as that in example 2, except that 5-methylthiophene-2-aldehyde was used to replace thiophene-2-aldehyde.
$^1$H NMR (CDCl$_3$, 400 MHz): δ 6.62 (d, J=8.0, 1H), 6.55 (d, J=8.0, 1H), 6.14 (s, 1H), 3.92 (d, J=14.8 Hz, 1H), 3.83 (s, 3H), 3.66 (dd, J=10.8 Hz, J=3.9 Hz, 1H), 3.56 (d, J=14.5 Hz, 1H), 3.29-3.24 (m, 1H), 3.23-3.08 (m, 2H), 2.85-2.70 (m, 3H), 2.37 (s, 3H). ESI-MS m/z: 288.0 [M+H]$^+$.

EXAMPLE 5

(S)-2-ethyl-8-methoxy-9-hydroxy-4,7,12,12a-tetrahydro-5H-benzo[g]thieno[3,2-a]quinolizine (AS005)

The titled product was prepared by the same procedure as that in example 1, except that 5-ethylthiophene-2-aldehyde was used to replace thiophene-2-aldehyde.
$^1$H NMR (CDCl$_3$, 400 MHz): δ 6.65 (d, J=8.1, 1H), 6.54 (d, J=8.1, 1H), 6.14 (s, 1H), 3.95 (d, J=14.8 Hz, 1H), 3.83 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 5H), 1.26 (t, J=7.2 Hz, 3H). ESI-MS m/z: 316.0 [M+H]$^+$.

EXAMPLE 6

(S)-2-n-propyl-8-methoxy-9-hydroxy-4,7,12,12a-tetrahydro-5H-benzo[g]thieno[3,2-a]quinolizine (AS006)

6.1 Preparation of 2-propionyl thiophene 1 g of thiophene was dissolved in 10 mL of anhydrous dichloromethane, added with 1.2 eq of propionylchloride at 0° C. under nitrogen, and then with 1.5 eq of anhydrous AlCl$_3$ in batches. The reaction was preformed at 0° C. for 1.5 hours, and monitored by TLC. The reaction mixture was treated with an icy 1N HCl under stirring and extracted with dichloromethane. The organic phase was evaporated to dryness to give oily 2-propionylthiophene (1.65 g). Yield, about 100%.
$^1$H NMR (CDCl$_3$, 400 MHz): δ 7.70 (d, J=4.0 Hz, 1H), 7.64 (d, J=5.0 Hz, 1H), 7.13 (dd, J=4.0, J=5.0 Hz, 1H), 2.94 (q, J=7.2 Hz, 2H), 1.23 (t, J=7.2 Hz, 3H). ESI-MS m/z: 142.2 [M+H]$^+$.

6.2 Preparation of 2-n-propylthiophene 2-propionylthiophene (1.5 g) was dissolved in trifluoroacetic acid (10 mL) at 0° C., added with 4 eq of triethyl silane, and stirred at room temperature overnight. Purification by column chromatography gave 2-n-propylthiophene. Yield, 92%.
$^1$H NMR (CDCl$_3$, 400 MHz): δ 7.10 (d, J=4.0 Hz, 1H), 6.91 (dd, J=4.0, J=5.0 Hz, 1H), 6.78 (d, J=5.0 Hz, 1H), 2.79 (t, J=7.4 Hz, 2H), 1.69 (m, 2H), 0.90 (t, J=7.4 Hz, 3H). ESI-MS m/z: 127.0 [M+H]$^+$.

6.3 Preparation of 5-n-propylthiophene-2-aldehyde 2-n-propylthiophene was dissolved in anhydrous dichloromethane at 0° C., and slowly added with titanium tetrachloride and dichloromethylether. The reaction was preformed at 0° C. to room temperature for about 1 hour. TLC showed that the reaction was completed. The reaction mixture was treated with ice water under agitating, and extracted with dichloromethane. The organic phase was evaporated to dryness to give 5-n-propyl thiophene-2-aldehyde.
$^1$H NMR (CDCl$_3$, 400 MHz): δ 7.70 (d, J=5.0 Hz, 1H), 6.91 (d, J=5.0 Hz, 1H), 2.66 (t, J=7.4 Hz, 2H), 1.60 (m, 2H), 0.91 (t, J=7.4 Hz, 3H). ESI-MS m/z: 155.1 [M+H]$^+$.

The following procedure was conducted the same as that in example 1 to give the title product, except that 5-n-propylthiophene-2-aldehyde was used to replace thiophene-2-aldehyde.

$^1$H NMR (CDCl$_3$, 400 MHz): δ 6.65 (d, J=8.1, 1H), 6.54 (d, J=8.1, 1H), 6.14 (s, 1H), 3.95 (d, J=14.8 Hz, 1H), 3.83 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 5H), 1.60 (m, 2H), 0.91 (t, J=7.2 Hz, 3H). ESI-MS m/z: 330.0 [M+H]$^+$.

EXAMPLE 7

(S)-2-n-butyl-8-methoxy-9-hydroxy-4,7,12,12a-tetrahydro-5H-benzo[g]thieno[3,2-a]quinolizine (AS007)

The titled product was prepared by the same procedure as that in example 6, except that n-butyrylchloride was used to replace propionylchloride.

$^1$H NMR (CDCl$_3$, 400 MHz): δ6.62 (d, J=8.0, 1H), 6.51 (d, J=8.0, 1H), 6.14 (s, 1H), 3.95 (d, J=14.4 Hz, 1H), 3.83 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.70 (m, 5H), 1.58 (m, 2H), 1.33 (m, 2H), 0.86 (t, J=7.2 Hz, 3H). ESI-MS m/z: 344.0 [M+H]$^+$.

EXAMPLE 8

(S)-2-n-amyl-8-methoxy-9-hydroxy-4,7,12,12a-tetrahydro-5H-benzo[g]thieno[3,2-a]quinolizine (AS008)

The titled product was prepared by the same procedure as that in example 6, except that valerylchloride was used to replace propionylchloride.

$^1$H NMR (CDCl$_3$, 400 MHz): δ 6.62 (d, J=8.0, 1H), 6.50 (d, J=8.0, 1H), 6.14 (s, 1H), 3.95 (d, J=14.4 Hz, 1H), 3.83 (s, 3H), 3.71 (dd, J=10.8 Hz, J=3.8 Hz, 1H), 3.55 (d, J=14.4 Hz, 1H), 3.30-3.24 (m, 1H), 3.16-3.08 (m, 2H), 2.85-2.70 (m, 5H), 1.58 (m, 2H), 1.33-1.28 (m, 4H), 0.86 (t, J=7.2 Hz, 3H). ESI-MS m/z: 358.1 [M+H]$^+$.

EXAMPLE 9

(S)-2-(2-methylpropyl)-8-methoxy-9-hydroxy-4,7,12,12a-tetrahydro-5H-benzo[g]thieno[3,2-a]quinolizine (AS009)

The titled product was prepared by the same procedure as that in example 6, except that 2-methylpropionylchloride was used to replace propionylchloride.

$^1$H NMR (CDCl$_3$, 400 MHz): δ 6.62 (d, J=8.0, 1H), 6.51 (d, J=8.0, 1H), 6.14 (s, 1H), 3.95 (d, J=14.4 Hz, 1H), 3.83 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.70 (m, 5H), 1.63 (m, 1H), 0.86 (t, J=7.2 Hz, 6H). ESI-MS m/z: 344.0 [M+H]$^+$.

EXAMPLE 10

(S)-2-(3-methylbutyl)-8-methoxy-9-hydroxy-4,7,12,12a-tetrahydro-5H-benzo[g]thieno[3,2-a]quinolizine (AS010)

The titled product was prepared by the same procedure as that in example 6, except that 3-methylbutyrylchloride was used to replace propionylchloride.

$^1$H NMR (CDCl$_3$, 400 MHz): δ 6.62 (d, J=8.0, 1H), 6.51 (d, J=8.0, 1H), 6.14 (s, 1H), 3.95 (d, J=14.4 Hz, 1H), 3.83 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.70 (m, 5H), 1.65-1.60 (m, 3H), 0.86 (t, J=7.2 Hz, 6H). ESI-MS m/z: 358.1 [M+H]$^+$.

EXAMPLE 11

(S)-2-cyclopropylmethyl-8-methoxy-9-hydroxy-4,7,12,12a-tetrahydro-5H-benzo[g]thieno[3,2-a]quinolizine (AS011)

The titled product was prepared by the same procedure as that in example 6, except that 2-cyclopropylformylchloride was used to replace propionylchloride.

$^1$H NMR (CDCl$_3$, 400 MHz): δ 6.60 (d, J=8.0, 1H), 6.49 (d, J=8.0, 1H), 6.14 (s, 1H), 3.93 (d, J=14.4 Hz, 1H), 3.81 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.75 (m, 3H), 2.55 (m, 2H), 0.94-1.27 (m, 1H), 0.51-0.55 (m, 2H), 0.19-0.47 (m, 2H). ESI-MS m/z: 342.0 [M+H]$^+$.

EXAMPLE 12

(S)-2-cyclobutylmethyl-8-methoxy-9-hydroxy-4,7,12,12a-tetrahydro-5H-benzo[g]thieno[3,2-a]quinolizine (AS012)

The titled product was prepared by the same procedure as that in example 6, except that 2-cyclobutylformylchloride was used to replace propionylchloride.

$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.75 (m, 3H), 2.62 (m, 2H), 2.34 (m, 1H), 2.05-1.78 (m, 6H). ESI-MS m/z: 356.1 [M+H]$^+$.

EXAMPLE 13

(S)-2-(2,2-dimethylpropyl)-8-methoxy-9-hydroxy-4,7,12,12a-tetrahydro-5H-benzo[g]thieno[3,2-a]quinolizine (AS013)

The titled product was prepared by the same procedure as that in example 6, except that 2,2-dimethylpropionylchloride was used to replace propionylchloride.

$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.75 (m, 3H), 2.45 (s, 2H), 0.98 (s, 9H). ESI-MS m/z: 358.1 [M+H]$^+$.

EXAMPLE 14

(S)-2-(2,2-dimethylbutyl)-8-methoxy-9-hydroxy-4,7,12,12a-tetrahydro-5H-benzo[g]thieno[3,2-a]quinolizine (AS014)

The titled product was prepared by the same procedure as that in example 6, except that 2,2-dimethylbutyrylchloride was used to replace propionylchloride.

$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.68 (dd, J=10.8 Hz, J=3.8 Hz, 1H), 3.54 (d, J=14.4

Hz, 1H), 3.29-3.24 (m, 1H), 3.16-3.08 (m, 2H), 2.85-2.75 (m, 5H), 1.55 (d, J=7.0 Hz, 2H), 0.94 (s, 9H). ESI-MS m/z: 358.1 [M+H]+.

EXAMPLE 15

(S)-2-(2-methylbutyl)-8-methoxy-9-hydroxy-4,7,12, 12a-tetrahydro-5H-benzo[g]thieno[3,2-a]quinolizine (AS015)

The titled product was prepared by the same procedure as that in example 6, except that 2-methylbutyrylchloride was used to replace propionylchloride.
$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.75 (m, 5H), 2.60-2.42 (m, 2H), 2.04 (m, 1H), 1.55 (m, 2H), 0.98-0.90 (m, 6H). ESI-MS m/z: 358.1 [M+H]+.

EXAMPLE 16

(S)-2-(2-chloroethyl)-8-methoxy-9-hydroxy-4,7,12, 12a-tetrahydro-5H-benzo[g]thieno[3,2-a]quinolizine (AS016)

The titled product was prepared by the same procedure as that in example 6, except that 2-chloroacetylchloride was used to replace propionylchloride.
$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.70-3.58 (m, 3H), 3.54 (d, J=14.4 Hz, 1H), 3.29-3.24 (m, 1H), 3.16-3.08 (m, 2H), 2.85-2.75 (m, 5H). ESI-MS m/z: 350.0 [M+H]+.

EXAMPLE 17

(S)-2-(3-chloro propyl)-8-methoxy-9-hydroxy-4,7, 12,12a-tetrahydro-5H-benzo[g]thieno[3,2-a]quinolizine (AS017)

The titled product was prepared by the same procedure as that in example 6, except that 3-chloropropionylchloride was used to replace propionylchloride.
$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.70-3.58 (m, 3H), 3.54 (d, J=14.4 Hz, 1H), 3.29-3.24 (m, 1H), 3.16-3.08 (m, 2H), 2.85-2.75 (m, 5H), 1.86 (m, 2H). ESI-MS m/z: 364.0 [M+H]+.

EXAMPLE 18

(S)-2-(2-chloro propyl)-8-methoxy-9-hydroxy-4,7, 12,12a-tetrahydro-5H-benzo[g]thieno[3,2-a]quinolizine (AS018)

The titled product was prepared by the same procedure as that in example 6, except that 2-chloropropionylchloride was used to replace propionylchloride.
$^1$H NMR (CDCl$_3$, 400 MHz): δ 6.60 (d, J=8.0, 1H), 6.49 (d, J=8.0, 1H), 6.12 (s, 1H), 3.99 (d, J=7.2 Hz, 1H), 3.92 (d, J=14.4 Hz, 1H), 3.81 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.75 (m, 5H), 1.60 (d, J=7.2 Hz, 3H). ESI-MS m/z: 364.1 [M+H]+.

EXAMPLE 19

(S)-2-(4-chloro butyl)-8-methoxy-9-hydroxy-4,7,12, 12a-tetrahydro-5H-benzo[g]thieno[3,2-a]quinolizine (AS019)

The titled product was prepared by the same procedure as that in example 6, except that 4-chlorobutyrylchloride was used to replace propionylchloride.
$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.70-3.58 (m, 3H), 3.54 (d, J=14.4 Hz, 1H), 3.29-3.24 (m, 1H), 3.16-3.08 (m, 2H), 2.85-2.75 (m, 5H), 1.77-1.61 (m, 4H). ESI-MS m/z: 378.1 [M+H]+.

EXAMPLE 20

(S)-2-(3-bromo propyl)-8-methoxy-9-hydroxy-4,7, 12,12a-tetrahydro-5H-benzo[g]thieno[3,2-a]quinolizine (AS020)

The titled product was prepared by the same procedure as that in example 6, except that 3-bromopropionylchloride was used to replace propionylchloride.
$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.62-3.50 (m, 3H), 3.54 (d, J=14.4 Hz, 1H), 3.29-3.24 (m, 1H), 3.16-3.08 (m, 2H), 2.85-2.75 (m, 5H), 2.07 (m, 2H). ESI-MS m/z: 408.0 [M+H]+

EXAMPLE 21

(S)-2-(2,2,2-trifluoroethyl)-8-methoxy-9-hydroxy-4, 7,12,12a-tetrahydro-5H-benzo[g]thieno[3,2-a]quinolizine (AS021)

The titled product was prepared by the same procedure as that in example 6, except that 2,2,2-trifluoroacetylchloride was used to replace propionylchloride.
$^1$H NMR (CDCl$_3$, 400 MHz): δ 6.65 (d, J=8.1, 1H), 6.54 (d, J=8.1, 1H), 6.12 (s, 1H), 3.95 (d, J=14.8 Hz, 1H), 3.83 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 3.02 (s, 3H), 2.85-2.70 (m, 3H). ESI-MS m/z: 370.1 [M+H]+.

EXAMPLE 22

(S)-8,9-dimethoxy-4,7,12,12a-tetrahydro-5H-benzo [g]thieno[3,2-a]quinolizine (AS022)

The titled product was prepared by the same procedure as that in example 1, except that 7,8-dimethoxy-3-isochromanone was used to replace thiophene-2-aldehyde.
$^1$H NMR (CDCl$_3$, 400 MHz): δ 6.64 (d, J=8.0, 1H), 6.58 (d, J=8.0, 1H), 6.12 (s, 1H), 3.91 (d, J=14.8 Hz, 1H), 3.81 (s, 6H), 3.66 (dd, J=10.8 Hz, J=3.9 Hz, 1H), 3.53 (d, J=14.5 Hz, 1H), 3.27-3.21 (m, 1H), 3.14-3.04 (m, 2H), 2.82-2.70 (m, 3H). ESI-MS m/z: 302.0 [M+H]+.

EXAMPLE 23

(S)-2-methyl-8,9-dimethoxy-4,7,12,12a-tetrahydro-5H-benzo[g]thieno[3,2-a]quinolizine (AS023)

The titled product was prepared by the same procedure as that in example 22, except that 5-methyl-thiophene-2-aldehyde was used to replace thiophene-2-aldehyde.

¹H NMR (CDCl₃, 400 MHz): δ 6.68 (d, J=8.1, 1H), 6.60 (d, J=8.1, 1H), 6.12 (s, 1H), 3.95 (d, J=14.8 Hz, 1H), 3.83 (s, 6H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 3H), 2.37 (s, 3H). ESI-MS m/z: 316.0 [M+H]⁺.

EXAMPLE 24

(S)-2-ethyl-8,9-dimethoxy-4,7,12,12a-tetrahydro-5H-benzo[g]thieno[3,2-a]quinolizine (AS024)

The titled product was prepared by the same procedure as that in example 22, except that 5-ethyl-2-thienal was used to replace 2-thienal.
¹H NMR (CDCl₃, 400 MHz): δ 6.67 (d, J=8.1, 1H), 6.59 (d, J=8.1, 1H), 6.12 (s, 1H), 3.95 (d, J=14.8 Hz, 1H), 3.83 (s, 6H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 5H), 1.26 (t, J=7.2 Hz, 3H). ESI-MS m/z: 330.0 [M+H]⁺.

EXAMPLE 25

(S)-2-n-propyl-8,9-dimethoxy-4,7,12,12a-tetrahydro-5H-benzo[g]thieno[3,2-a]quinolizine (AS025)

The titled product was prepared by the same procedure as that in example 22, except that 5-n-propyl-2-thienal was used to replace 2-thienal.
¹H NMR (CDCl₃, 400 MHz): δ 6.68 (d, J=8.1, 1H), 6.61 (d, J=8.1, 1H), 6.12 (s, 1H), 3.95 (d, J=14.8 Hz, 1H), 3.83 (s, 6H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 5H), 1.60 (m, 2H), 0.91 (t, J=7.2 Hz, 3H). ESI-MS m/z: 344.0 [M+H]⁺.

EXAMPLE 26

(S)-2-(2-methyl propyl)-8,9-dimethoxy-4,7,12,12a-tetrahydro-5H-benzo[g]thieno[3,2-a]quinolizine (AS026)

The titled product was prepared by the same procedure as that in example 22, except that 2-methylpropionylchloride was used to replace propionylchloride.
¹H NMR (CDCl₃, 400 MHz): δ 6.66 (d, J=8.0, 1H), 6.60 (d, J=8.0, 1H), 6.14 (s, 1H), 3.95 (d, J=14.4 Hz, 1H), 3.83 (s, 6H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.70 (m, 5H), 1.63 (m, 1H), 0.86 (t, J=7.2 Hz, 6H). ESI-MS m/z: 358.1 [M+H]⁺.

EXAMPLE 27

(S)-2-cyclopropylmethyl-8,9-dimethoxy-4,7,12,12a-tetrahydro-5H-benzo[g]thieno[3,2-a]quinolizine (AS027)

The titled product was prepared by the same procedure as that in example 22, except that 2-cyclopropylformylchloride was used to replace propionylchloride.
¹H NMR (CDCl₃, 400 MHz): δ 6.64 (d, J=8.0, 1H), 6.55 (d, J=8.0, 1H), 6.12 (s, 1H), 3.93 (d, J=14.4 Hz, 1H), 3.81 (s, 6H), 3.68 (dd, J=10.8 Hz, J=3.8 Hz, 1H), 3.54 (d, J°=14.4 Hz, 1H), 3.29-3.24 (m, 1H), 3.16-3.08 (m, 2H), 2.85-2.75 (m, 3H), 2.55 (m, 2H), 0.94-1.27 (m, 1H), 0.51-0.55 (m, 2H), 0.19-0.47 (m, 2H). ESI-MS m/z: 356.0 [M+H]⁺.

EXAMPLE 28

(S)-2-(2,2-dimethyl propyl)-8,9-dimethoxy-4,7,12,12a-tetrahydro-5H-benzo[g]thieno[3,2-a]quinolizine (AS028)

The titled product was prepared by the same procedure as that in example 22, except that 2,2-dimethylpropionylchloride was used to replace propionylchloride.
¹H NMR (CDCl₃, 400 MHz): δ 6.66 (d, J=8.0, 1H), 6.58 (d, J=8.0, 1H), 6.12 (s, 1H), 3.93 (d, J=14.4 Hz, 1H), 3.81 (s, 6H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.75 (m, 3H), 2.45 (s, 2H), 0.98 (s, 9H). ESI-MS m/z: 372.1 [M+H]⁺.

EXAMPLE 29

(S)-2-(2-chloroethyl)-8,9-dimethoxy-4,7,12,12a-tetrahydro-5H-benzo[g]thieno[3,2-a]quinolizine (AS029)

The titled product was prepared by the same procedure as that in example 22, except that 2-chloroacetylchloride was used to replace propionylchloride.
¹H NMR (CDCl₃, 400 MHz): δ 6.64 (d, J=8.0, 1H), 6.52 (d, J=8.0, 1H), 6.12 (s, 1H), 3.93 (d, J=14.4 Hz, 1H), 3.81 (s, 6H), 3.70-3.58 (m, 3H), 3.54 (d, J=14.4 Hz, 1H), 3.29-3.24 (m, 1H), 3.16-3.08 (m, 2H), 2.85-2.75 (m, 5H). ESI-MS m/z: 364.1 [M+H]⁺.

EXAMPLE 30

(S)-2-(2,2,2-trifluoroethyl)-8,9-dimethoxy-4,7,12,12a-tetrahydro-5H-benzo[g]thieno[3,2-a]quinolizine (AS030)

The titled product was prepared by the same procedure as that in example 22, except that 2,2,2-trifluoroacetylchloride was used to replace propionylchloride.
¹H NMR (CDCl₃, 400 MHz): δ 6.68 (d, J=8.1, 1H), 6.56 (d, J=8.1, 1H), 6.12 (s, 1H), 3.95 (d, J=14.8 Hz, 1H), 3.83 (s, 6H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 3.02 (s, 3H), 2.85-2.70 (m, 3H). ESI-MS m/z: 384.4 [M+H]⁺.

EXAMPLE 31

(S)-8,11-dimethoxy-4,7,12,12a-tetrahydro-5H-benzo[g]thieno[3,2-a]quinolizine (AS031)

31.1 Preparation of N-(thiophene-2-ethyl)-2,5-dimethoxy-phenylacetamide 1 g of 2,5-dimethoxyphenylacetic acid was dissolved in anhydrous dichloromethane, added with a condensing agent of 1-ethyl-3-(3-dimethylaminopropyl)carbodiimide hydrochloride (EDCI) in batches under agitating, and then with 2 eq of triethylamine, followed by addition of 1 eq of thiophene-2-ethylamine. The reaction was performed at room temperature for 3 hours. After that, the reaction mixture was quenched by water, and extracted with dichloromethane. The organic phase was evaporated to dryness and the residue was purified by column chromatography to give the product. Yield, 72%.
¹H NMR (CDCl₃, 400 MHz): δ 7.40 (d, J=7.8 Hz, 1H), 6.93 (d, J=7.8 Hz, 1H), 6.90 (s, 1H), 6.80 (d, J=7.8 Hz, 1H), 6.80 (d, J=8.0 Hz, 1H), 6.69 (d, J=8.0 Hz, 1H), 3.85 (s, 6H), 3.66 (s, 2H), 3.58 (t, J=12.0 Hz, 2H), 2.78 (t, J=12.0 Hz, 2H). ESI-MS m/z: 306.0 [M+H]$^+$.

31.2, Preparation of (S)-8,11-dimethoxy-4,7,12,12a-tetrahydro-5H-benzo[g]thieno[3,2-a]quinolizine (AS031)

(S)-4-(2,5-dimethoxybenzyl)-4,5,6,7-tetrahydro-thieno(3,2-c)pyridine was mixed with formaldehyde/formic acid (5 mL/7.5 mL/1 mmol substrate), and reacted at 90° C. under nitrogen for 2 hours. The reaction mixture was evaporated to remove most of the solvent, adjusted with saturated NaHCO$_3$ to be alkaline, and extracted triply with dichloromethane. The organic phase was evaporated to dryness, and the residue was purified by column chromatography to give the product.

$^1$H NMR (CDCl$_3$, 400 MHz): δ 6.64 (d, J=8.0 Hz, 1H), 6.58 (d, J=8.0 Hz, 1H), 6.12 (s, 1H), 3.91 (d, J=14.8 Hz, 1H), 3.81 (s, 6H), 3.66 (dd, J=10.8 Hz, J=3.9 Hz, 1H), 3.53 (d, J=14.5 Hz, 1H), 3.27-3.21 (m, 1H), 3.14-3.04 (m, 2H), 2.82-2.70 (m, 3H). ESI-MS m/z: 302.0 [M+H]$^+$.

EXAMPLE 32

(S)-2-methyl-8,11-dimethoxy-4,7,12,12a-tetrahydro-5H-benzo[g]thieno[3,2-a]quinolizine (AS032)

The titled product was prepared by the same procedure as that in example 31, except that 5-methylthiophene-2-ethylamine was used to replace thiophene-2-ethylamine.

$^1$H NMR (CDCl$_3$, 400 MHz): δ 6.64 (d, J=8.0 Hz, 1H), 6.59 (d, J=8.0 Hz, 1H), 6.12 (s, 1H), 3.95 (d, J=14.8 Hz, 1H), 183 (s, 6H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 3H), 2.37 (s, 3H). ESI-MS m/z: 316.0 [M+H]$^+$.

EXAMPLE 33

(S)-2-ethyl-8,11-dimethoxy-4,7,12,12a-tetrahydro-5H-benzo[g]thieno[3,2-a]quinolizine (AS033)

The titled product was prepared by the same procedure as that in example 31, except that 5-ethylthiophene-2-ethylamine was used to replace thiophene-2-ethylamine.

$^1$H NMR (CDCl$_3$, 400 MHz): δ 6.64 (d, J=8.8 Hz, 1H), 6.58 (d, J=8.8 Hz, 1H), 6.12 (s, 1H), 3.95 (d, J=14.8 Hz, 1H), 3.83 (s, 6H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 5H), 1.26 (t, J=7.2 Hz, 3H). ESI-MS m/z: 330.0 [M+H]$^+$.

EXAMPLE 34

(S)-2-(2-methyl propyl)-8,11-dimethoxy-4,7,12,12a-tetrahydro-5H-benzo[g]thieno[3,2-a]quinolizine (AS034)

The titled product was prepared by the same procedure as that in example 31, except that 5-(2-methylpropyl)thiophene-2-ethylamine was used to replace thiophene-2-ethylamine.

$^1$H NMR (CDCl$_3$, 400 MHz): δ 6.64 (d, J=8.0 Hz, 1H), 6.58 (d, J=8.0 Hz, 1H), 6.12 (s, 1H), 3.95 (d, J=14.4 Hz, 1H), 3.83 (s, 6H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.70 (m, 5H), 1.63 (m, 1H), 0.86 (t, J=7.2 Hz, 6H). ESI-MS m/z: 358.1 [M+H]$^+$.

EXAMPLE 35

(S)-2-(cyclopropylmethyl)-8,11-dimethoxy-4,7,12,12a-tetrahydro-5H-benzo[g]thieno[3,2-a]quinolizine (AS035)

The titled product was prepared by the same procedure as that in example 31, except that 5-cyclopropylmethylthiophene-2-ethylamine was used to replace thiophene-2-ethylamine.

$^1$H NMR (CDCl$_3$, 400 MHz): δ 6.64 (d, J=8.0, 1H), 6.59 (d, J=8.0, 1H), 6.12 (s, 1H), 3.93 (d, J=14.4 Hz, 1H), 3.81 (s, 6H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.75 (m, 3H), 2.55 (m, 2H), 0.94-1.27 (m, 1H), 0.51-0.55 (m, 2H), 0.19-0.47 (m, 2H). ESI-MS m/z: 356.0 [M+H]$^+$.

EXAMPLE 36

(S)-2-(2-chloroethyl)-8,11-dimethoxy-4,7,12,12a-tetrahydro-5H-benzo[g]thieno[3,2-a]quinolizine (AS036)

The titled product was prepared by the same procedure as that in example 31, except that 5-(2-chloroethyl)thiophene-2-ethylamine was used to replace thiophene-2-ethylamine.

$^1$H NMR (CDCl$_3$, 400 MHz): δ 6.64 (d, J=8.0, 1H), 6.58 (d, J=8.0, 1H), 6.12 (s, 1H), 3.93 (d, J=14.4 Hz, 1H), 3.81 (s, 6H), 3.70-3.58 (m, 3H), 3.54 (d, J=14.4 Hz, 1H), 3.29-3.24 (m, 1H), 3.16-3.08 (m, 2H), 2.85-2.75 (m, 5H). ESI-MS m/z: 364.1 [M+H]$^+$.

EXAMPLE 37

(S)-2-(2,2,2-trifluoroethyl)-8,11-dimethoxy-4,7,12,12a-tetrahydro-5H-benzo[g]thieno[3,2-a]quinolizine (AS037)

The titled product was prepared by the same procedure as that in example 31, except that 5-(2,2,2-trifluoroethyl)thiophene-2-ethylamine was used to replace thiophene-2-ethylamine.

$^1$H NMR (CDCl$_3$, 400 MHz): δ 6.62 (d, J=8.1, 1H), 6.56 (d, J=8.1, 1H), 6.12 (s, 1H), 3.95 (d, J=14.8 Hz, 1H), 3.81 (s, 6H), 3.68 (dd, J=10.8 Hz, J=3.8 Hz, 1H), 3.54 (d, J=14.5 Hzr 1H), 3.29-3.24 (m, 1H), 3.16-3.08 (m, 2H), 3.02 (s, 3H), 2.85-2.70 (m, 3H). ESI-MS m/z: 384.4 [M+H]$^+$.

EXAMPLE 38 cl (S)-2,4-dimethyl-8-methoxy-9-hydroxy-4,7,12,12a-tetrahydro-5H-benzo[g]thieno[3,2-a]quinolizine (AS038)

The titled product was prepared by the same procedure as that in example 1, except that 5-methylthiophene-2-ethylketone was used to replace 2-thienal.

$^1$H NMR (CDCl$_3$, 400 MHz): δ 6.65 (d, J=8.1, 1H), 6.54 (d, J=8.1, 1H), 6.12 (s, 1H), 3.95 (d, J=14.8 Hz, 1H), 3.83 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 3H), 2.85-2.70 (m, 1H), 2.37 (s, 3H), 1.25 (d, J=7.2 Hz, 3H). ESI-MS m/z: 316.4 [M+H]$^+$.

EXAMPLE 39

(S)-2,5-dimethyl-8-methoxy-9-hydroxy-4,7,12,12a-tetrahydro-5H-benzo[g]thieno[3,2-a]quinolizine (AS039)

The titled product was prepared by the same procedure as that in example 1, except that 5-methyl-2-thienal and nitroethane were used to replace 2-thienal and nitromethane.

¹H NMR (CDCl₃, 400 MHz): δ 6.65 (d, J=8.1, 1H), 6.54 (d, J=8.1, 1H), 6.12 (s, 1H), 3.95 (d, J=14.8 Hz, 1H), 3.83 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 2H), 2.37 (s, 3H), 1.12 (d, J=7.2 Hz, 3H). ESI-MS m/z: 316.4 [M+H]$^+$.

EXAMPLE 40

(S)-2,7-dimethyl-8-methoxy-9-hydroxy-4,7,12,12a-tetrahydro-5H-benzo[g]thieno[3,2-a]quinolizine (AS040)

The titled product was prepared by the same procedure as that in example 1, except that metaldehyde was used to replace paraformaldehyde.

¹H NMR (CDCl₃, 400 MHz): δ 6.65 (d, J=8.1, 1H), 6.54 (d, J=8.1, 1H), 6.12 (s, 1H), 3.99 (d, J=14.8 Hz, 1H), 3.90 (m, 1H), 3.83 (s, 3H), 3.10-3.02 (m, 2H), 2.80-2.65 (m, 4H), 2.37 (s, 3H), 1.28 (d, J=7.2 Hz, 3H). ESI-MS m/z: 316.4 [M+H]$^+$.

EXAMPLE 41

(S)-2-methyl-8-methoxy-9-hydroxy-4,7,12,12a-tetrahydro-5H-benzo[g]thieno[3,2-a]quinolizin-7(5H)-one (AS041)

The titled product was prepared by the same procedure as that in example 1, except that chloroformylchloride was used to replace paraformaldehyde.

¹H NMR (CDCl₃, 400 MHz): δ 6.65 (d, J=8.1, 1H), 6.54 (d, J=8.1, 1H), 6.12 (s, 1H), 5.11 (d, J=14.8 Hz, 1H), 3.83 (s, 3H), 3.58-3.48 (m, 2H), 3.10-3.02 (m, 2H), 2.84-2.80 (m, 2H), 2.37 (s, 3H). ESI-MS m/z: 316.4 [M+H]$^+$.

EXAMPLE 42

(S)-1,2-dimethyl-8-methoxy-9-hydroxy-4,7,12,12a-tetrahydro-5H-benzo[g]thieno[3,2-a]quinolizine (AS042)

The titled product was prepared by the same procedure as that in example 1, except that 4,5-dimethyl-2-thienal was used to replace 2-thienal.

¹H NMR (CDCl₃, 400 MHz): δ 6.65 (d, J=8.1, 1H), 6.54 (d, J=8.1, 1H), 4.11 (d, J=14.8 Hz, 1H), 3.83 (s, 3H), 3.68 (dd, J=10.8 Hz, J=3.8 Hz, 1H), 3.54 (d, J=14.5 Hz, 1H), 3.10-3.02 (m, 2H), 2.74-2.63 (m, 4H), 2.37 (s, 3H), 2.20 (s, 3H). ESI-MS m/z: 316.4 [M+H]$^+$.

EXAMPLE 43

(S)-2,8-dimethoxy-9-hydroxy-4,7,12,12a-tetrahydro-5H-benzo[g]thieno[3,2-a]quinolizine (AS043)

The titled product was prepared by the same procedure as that in example 1, except that 5-methoxy-2-thienal was used to replace 2-thienal.

¹H NMR (CDCl₃, 400 MHz): δ 6.65 (d, J=8.1, 1H), 6.54 (d, J=8.1, 1H), 5.76 (s, 1H), 4.11 (d, J=14.8 Hz, 1H), 3.90 (s, 3H), 3.83 (s, 3H), 3.68 (dd, J=10.8 Hz, J=3.8 Hz, 1H), 3.54 (d, J=14.5 Hz, 1H), 3.10-3.02 (m, 2H), 2.74-2.63 (m, 4H). ESI-MS m/z: 318.4 [M+H]$^+$.

EXAMPLE 44

(S)-2-fluoro-8-methoxy-9-hydroxy-4,7,12,12a-tetrahydro-5H-benzo[g]thieno[3,2-a]quinolizine (AS044)

The titled product was prepared by the same procedure as that in example 1, except that 5-fluoro-2-thienal was used to replace 2-thienal.

¹H NMR (CDCl₃, 400 MHz): δ 6.65 (d, J=8.1, 1H), 6.54 (d, J=8.1, 1H), 6.50 (s, 1H), 4.11 (d, J=14.8 Hz, 1H), 3.88 (s, 3H), 3.68 (dd, J=10.8 Hz, J=3.8 Hz, 1H), 3.54 (d, J=14.5 Hz, 1H), 3.10-3.02 (m, 2H), 2.74-2.63 (m, 4H). ESI-MS m/z: 306.4 [M+H]$^+$.

EXAMPLE 45

(S)-2-methyl-8-methoxy-9-hydroxy-4,7,12,12a-tetrahydro-5H-benzo[g]thieno[2,3-a]quinolizine (AS045)

The titled product was prepared by the same procedure as that in example 1, except that 5-methyl-3-thienal was used to replace 2-thienal.

¹H NMR (CDCl₃, 400 MHz): δ 6.62 (d, J=8.1, 1H), 6.56 (d, J=8.1, 1H), 6.14 (s, 1H), 4.11 (d, J=14.8 Hz, 1H), 3.83 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 3H), 2.36 (s, 3H). ESI-MS m/z: 302.0 [M+H]$^+$.

EXAMPLE 46

(S)-2,8-dimethoxy-9-hydroxy-4,7,12,12a-tetrahydro-5H-benzo[g]thieno[2,3-a]quinolizine (AS046)

The titled product was prepared by the same procedure as that in example 1, except that 5-methoxy-3-thienal was used to replace 2-thienal.

¹H NMR (CDCl₃, 400 MHz): δ 6.65 (d, J=8.1, 1H), 6.54 (d, J=8.1, 1H), 5.76 (s, 1H), 4.11 (d, J=14.8 Hz, 1H), 3.90 (s, 3H), 3.83 (s, 3H), 3.68 (dd, J=10.8 Hz, J=3.8 Hz, 1H), 3.54 (d, J=14.5 Hz, 1H), 3.10-3.02 (m, 2H), 2.74-2.63 (m, 4H). ESI-MS m/z: 318.4 [M+H]$^+$.

EXAMPLE 47

(S)-8-methoxy-9-acetoxy-4,7,12,12a-tetrahydro-5H-benzo[g]thieno[3,2-a]quinolizine (AS047)

The titled product was prepared by the same procedure as that in example 1, except that 7-acetoxy-8-methoxy-3-isochromanone was used to replace 7-benzyloxy-8-methoxy-3-isochromanone.

¹H NMR (CDCl₃, 400 MHz): δ 7.28 (d, J=8.0, 1H), 6.94 (d, J=8.0, 1H), 6.78 (d, J=8.1, 1H), 6.60 (d, J=8.1, 1H), 3.95 (d, J=14.8 Hz, 1H), 3.83 (s, 3H), 3.68-3.54 (m, 2H), 3.29-3.24 (m, 2H), 3.16-3.08 (m, 21-1), 2.85-2.70 (m, 2H), 2.29 (s, 3H). ESI-MS m/z: 329.0 [M+H]$^+$.

EXAMPLE 48

(S)-8-methoxy-9-(2'-hydroxyethoxy)-4,7,12,12a-tetrahydro-5H-benzo[g]thieno[3,2-a]quinolizine (AS048)

The titled product was prepared by the same procedure as that in example 1, except that 7-(2'-hydroxyethoxy)-8- methoxy-3-isochromanone was used to replace 7-benzyloxy-8-methoxy-3-isochromanone.

$^1$H NMR (CDCl$_3$, 400 MHz): δ 7.28 (d, J=8.0, 1H), 6.94 (d, J=8.0, 1H), 6.78 (d, J=8.1, 1H), 6.60 (d, J=8.1, 1H), 4.15-4.10 (m, 2H), 3.95 (d, J=14.8 Hz, 1H), 3.83 (s, 3H), 3.68-3.54 (m, 4H), 3.29-3.24 (m, 2H), 3.16-3.08 (m, 2H), 2.85-2.70 (m, 2H). ESI-MS m/z: 332.0 [M+H]$^+$.

EXAMPLE 49

(S)-8-methoxy-9-(2'-dimethylaminoethoxy)-4,7,12,12a-tetrahydro-5H-benzo[g]thieno[3,2-a]quinolizine (AS049)

The titled product was prepared by the same procedure as that in example 1, except that 7-(T-dimethylaminoethoxy)-8-methoxy-3-isochromanone was used to replace 7-benzyloxy-8-methoxy-3-isochromanone.

$^1$H NMR (CDCl$_3$, 400 MHz): δ 7.28 (d, J=8.0, 1H), 6.94 (d, J=8.0, 1H), 6.78 (d, J=8.1, 1H), 6.60 (d, J=8.1, 1H), 4.15-4.10 (m, 2H), 3.95 (d, J=14.8 Hz, 1H), 3.83 (s, 3H), 3.68-3.54 (m, 4H), 3.29-3.24 (m, 2H), 3.16-3.08 (m, 2H), 2.85 (s, 6H), 2.80-2.70 (m, 2H). ESI-MS m/k: 359.1 [M+H]$^+$.

EXAMPLE 50

(S)-8-methoxy-9-amino-4,7,12,12a-tetrahydro-5H-benzo[g]thieno[3,2-a]quinolizine (AS050)

The titled product was prepared by the same procedure as that in example 1, except that 7-acetamido-8-methoxy-3-isochromanone was used to replace 7-benzyloxy-8-methoxy-3-isochromanone.

$^1$H NMR (CDCl$_3$, 400 MHz): δ 7.18 (d, J=8.1, 1H), 6.70 (d, J=8.1, 1H), 6.48 (d, J=8.0, 1H), 6.31 (d, J=8.0, 1H), 6.22 (s, 2H), 3.95 (d, J=14.8 Hz, 1H), 3.83 (s, 3H), 3.68-3.54 (m, 2H), 3.29-3.24 (m, 2H), 3.16-3.08 (m, 2H), 2.85-2.70 (m, 2H). ESI-MS m/z: 287.0 [M+H]$^+$.

EXAMPLE 51

(S)-8-methoxy-9-acetamido-4,7,12,12a-tetrahydro-5H-benzo[g]thieno[3,2-a]quinolizine (AS051)

The titled product was prepared by the same procedure as that in example 1, except that 7-acetamido-8-methoxy-3-isochromanone was used to replace 7-benzyloxy-8-methoxy-3-isochromanone.

$^1$H NMR (CDCl$_3$, 400 MHz): δ 7.28 (d, J=8.0, 1H), 7.30-7.20 (m, 2H), 6.78 (d, J=8.1, 1H), 6.60 (d, J=8.1, 1H), 3.95 (d, J=14.8 Hz, 1H), 3.83 (s, 311), 3.68-3.54 (m, 2H), 3.29-3.24 (m, 2H), 3.16-3.08 (m, 2H), 2.85-2.70 (m, 2H), 2.17 (s, 3H). ESI-MS m/z: 329.0 [M+H]$^+$.

EXAMPLE 52

(S)-8-methoxy-9-methylsulfonylamido-4,7,12,12a-tetrahydro-5H-benzo[g]thieno[3,2-a]quinolizine (AS052)

The titled product was prepared by the same procedure as that in example 1, except that 7-methylsulfonylamido-8-methoxy-3-isochromanone was used to replace 7-benzyloxy-8-methoxy-3-isochromanone.

$^1$H NMR (CDCl$_3$, 400 MHz): δ 7.28 (d, J=8.0, 1H), 6.78 (d, J=8.1, 1H), 6.70 (d, J=8.1, 1H), 6.60 (d, J=8.1, 1H), 3.95 (d, J=14.8 Hz, 1H), 3.83 (s, 3H), 3.68-3.54 (m, 2H), 3.29-3.24 (m, 2H), 3.16-3.08 (m, 2H), 2.93 (s, 3H), 2.85-2.70 (m, 2H). ESI-MS m/z: 365.0 [M+H]$^+$.

EXAMPLE 53

(S)-8-methoxy-9-hydroxy-4,7,12,12a-tetrahydro-5H-benzo[g]furo[3,2-a]quinolizine (AF001)

The titled product was prepared by the same procedure as that in example 1, except that 2-furfural was used to replace 2-thienal.

$^1$H NMR (CDCl$_3$, 400 MHz): δ 7.24 (d, J=5.4 Hz, 1H), 6.86 (d, J=5.4 Hz, 1H), 6.62 (d, J=8.1, 1H), 6.54 (d, J=8.1, 1H), 3.91 (d, J=14.8 Hz, 1H), 3.81 (s, 3H), 3.66 (dd, J=10.8 Hz, J=3.9 Hz, 1H), 3.53 (d, J=14.5 Hz, 1H), 3.27-3.21 (m, 1H), 3.14-3.04 (m, 2H), 2.82-2.70 (m, 3H). ESI-MS m/z: 272.1 [M+H]$^+$.

EXAMPLE 54

(S)-2-methyl-8-methoxy-9-hydroxy-4,7,12,12a-tetrahydro-5H-benzo[g]furo[3,2-a]quinolizine (AF002)

The titled product was prepared by the same procedure as that in example 1, except that 5-methyl-2-furfural was used to replace 2-thienal.

$^1$H NMR (CDCl$_3$, 400 MHz): δ 6.65 (d, J=8.1, 1H), 6.54 (d, J=8.1, 1H), 6.14 (s, 1H), 3.95 (d, J=14.8 Hz, 1H), 3.83 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 3H), 2.37 (s, 3H). ESI-MS m/z: 286.0 [M+H]$^+$.

EXAMPLE 55

(S)-2-ethyl-8-methoxy-9-hydroxy-4,7,12,12a-tetrahydro-5H-benzo[g]furo[3,2-a]quinolizine (AF003)

The titled product was prepared by the same procedure as that in example 1, except that 5-ethyl-2-furfural was used to replace 2-thienal.

$^1$H NMR (CDCl$_3$, 400 MHz): δ 6.65 (d, J=8.1, 1H), 6.54 (d, J=8.1, 1H), 6.14 (s, 1H), 3.95 (d, J=14.8 Hz, 1H), 3.83 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.70 (m, 5H), 1.26 (t, J=7.2 Hz, 3H). ESI-MS m/z: 300.1 [M+H]$^+$.

EXAMPLE 56

(S)-2-(2-methylpropyl)-8-methoxy-9-hydroxy-4,7,12,12a-tetrahydro-5H-benzo[g]furo[3,2-a]quinolizine (AF004)

The titled product was prepared by the same procedure as that in example 6, except that 5-(2-methylpropyl)-2-furfural was used to replace 2-thienal.

$^1$H NMR (CDCl$_3$, 400 MHz): δ 6.62 (d, J=8.0, 1H), 6.51 (d, J=8.0, 1H), 6.14 (s, 1H), 3.95 (d, J=14.4 Hz, 1H), 3.83 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.70 (m, 5H), 1.63 (m, 1H), 0.86 (t, J=7.2 Hz, 6H). ESI-MS m/z: 328.1 [M+H]$^+$.

EXAMPLE 57

(S)-2-cyclopropylmethyl-8-methoxy-9-hydroxy-4,7,12,12a-tetrahydro-5H-benzo[g]furo[3,2-a]quinolizine (AF005)

The titled product was prepared by the same procedure as that in example 1, except that 5-cyclopropylmethyl-2-furfural was used to replace 2-thienal.

$^1$H NMR (CDCl$_3$, 400 MHz): δ 6.60 (d, J=8.0, 1H), 6.49 (d, J=8.0, 1H), 6.14 (s, 1H), 3.93 (d, J=14.4 Hz, 1H), 3.81 (s, 3H), 3.68 (dd, J=10.8 Hz, J=3.8 Hz, 1H), 3.54 (d, J=14.4 Hz, 1H), 3.29-3.24 (m, 1H), 3.16-3.08 (m, 2H), 2.85-2.75 (m, 3H), 2.55 (m, 2H), 0.94-1.27 (m, 1H), 0.51-0.55 (m, 2H), 0.19-0.47 (m, 2H). ESI-MS m/z: 326.1 [M+H]$^+$.

EXAMPLE 58

(S)-2-(2-chloroethyl)-8-methoxy-9-hydroxy-4,7,12,12a-tetrahydro-5H-benzo[g]furo[3,2-a]quinolizine (AF006)

The titled product was prepared by the same procedure as that in example 1, except that 5-(2-chloroethyl)-2-furfural was used to replace 2-thienal.

$^1$H NMR (CDCl$_3$, 400 MHz): δ 6.60 (d, J=8.0, 1H), 6.49 (d, J=8.0, 1H), 6.12 (s, 1H), 3.93 (d, J=14.4 Hz, 1H), 3.81 (s, 3H), 3.70-3.58 (m, 3H), 3.54 (d, J=14.4 Hz, 1H), 3.29-3.24 (m, 1H), 3.16-3.08 (m, 2H), 2.85-2.75 (m, 5H). ESI-MS m/z: 334.1 [M+H]$^+$.

EXAMPLE 59

(S)-2-methyl-8-methoxy-9-hydroxy-4,7,12,12a-tetrahydro-5H-benzo[g]furo[2,3-a]quinolizine (AF007)

The titled product was prepared by the same procedure as that in example 45, except that 5-methyl-3-furfural was used.

$^1$H NMR (CDCl$_3$, 400 MHz): δ 6.62 (d, J=8.1, 1H), 6.56 (d, J=8.1, 1H), 6.14 (s, 1H), 4.11 (d, J=14.8 Hz, 1H), 3.83 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 3H), 2.36 (s, 3H). ESI-MS m/z: 286.0 [M+H]$^+$.

EXAMPLE 60

(S)-2-ethyl-8-methoxy-9-hydroxy-4,7,12,12a-tetrahydro-5H-benzo[g]furo[2,3-a]quinolizine (AF008)

The titled product was prepared by the same procedure as that in example 1, except that 5-ethyl-3-furfural was used to replace 2-thienal.

$^1$H NMR (CDCl$_3$, 400 MHz): δ 6.62 (d, J=8.1, 1H), 6.56 (d, J=8.1, 1H), 6.14 (s, 1H), 4.11 (d, J=14.8 Hz, 1H), 3.83 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 5H), 1.25 (t, J=7.0 Hz, 3H). ESI-MS m/z: 300.1 [M+H]$^+$.

EXAMPLE 61

(S)-2-(2-chloroethyl)-8-methoxy-9-hydroxy-4,7,12,12a-tetrahydro-5H-benzo[g]furo[2,3-a]quinolizine (AF009)

The titled product was prepared by the same procedure as that in example 1, except that 5-(2-chloroethyl)-3-furfural was used to replace 2-thienal.

$^1$H NMR (CDCl$_3$, 400 MHz): δ 6.62 (d, J=8.1, 1H), 6.56 (d, J=8.1, 1H), 6.14 (s, 1H), 4.11 (d, J=14.8 Hz, 1H), 3.83 (s, 3H), 3.71 (m, 2H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 5H). ESI-MS m/z: 350.1 [M+H]$^+$.

EXAMPLE 62

(S)-2,3-dimethoxy-5,7,8,13,13b,14-hexahydroindolo[2',3':3,4]pyrido[1,2-b]isoquinoline (A1001)

The titled product was prepared by the same procedure as that in example 31, except that tryptamine was used to replace thiophene-2-ethylamine and 3,4-dimethoxyphenylacetic acid was used to replace 2,5-dimethoxyphenylacetic acid.

$^1$H NMR (CDCl$_3$, 400 MHz): δ 7.13-7.08 (m, 4H), 6.82 (s, 1H), 6.76 (s, 1H), 4.11 (d, J=14.8 Hz, 1H), 3.90 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H). ESI-MS m/z: 335.2 [M+H]$^+$.

EXAMPLE 63

(S)-3-hydroxy-4-methoxy-5,7,8,13,13b,14-hexahydroindolo[2',3':3,4]pyrido[1,2-b]isoquinoline (A1002)

The titled product was prepared by the same procedure as that in example 1, except that tryptamine was used to replace thiophene-2-ethylamine.

$^1$H NMR (CDCl$_3$, 400 MHz): δ 7.13-7.08 (m, 4H), 6.66 (d, J=8.0 Hz, 1H), 6.60 (d, J=8.0 Hz, 1H), 4.11 (d, J=14.8 Hz, 1H), 3.90 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H). ESI-MS m/z: 335.2 [M+H]$^+$.

EXAMPLE 64

(S)-3-hydroxy-4,10-dimethoxy-5,7,8,13,13b,14-hexahydroindolo[2',3':3,4]pyrido[1,2-b]isoquinoline (A1003)

The titled product was prepared by the same procedure as that in example 1, except that 5-methoxytryptamine was used to replace thiophene-2-ethylamine.

$^1$H NMR (CDCl$_3$, 400 MHz): δ 7.06 (dd, J=8.0 Hz, 1H), 6.89 (dd, J=8.0 Hz, 1H), 6.66 (d, J=8.0 Hz, 1H), 6.60 (m, 2H), 4.11 (d, J=14.8 Hz, 1H), 3.90 (s, 3H), 3.85 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H). ESI-MS m/z: 351.1 [M+H]$^+$.

EXAMPLE 65

(S)-3-hydroxy-4-methoxy-10-methyl-5,7,8,13,13b,14-hexahydroindolo[2',3':3,4]pyrido[1,2-b]isoquinoline (A1004)

The titled product was prepared by the same procedure as that in example 1, except that 5-methyltryptamine was used to replace thiophene-2-ethylamine.

$^1$H NMR (CDCl$_3$, 400 MHz): δ 7.03 (dd, J=8.0 Hz, 1H), 6.99 (dd, J=8.0 Hz, 1H), 6.92 (s, 1H), 6.60 (m, 2H), 4.11 (d, J=14.8 Hz, 1H), 3.85 (s, 3H), 3.70 (dd, J=10.8 Hz, J=3.8 Hz,

1H), 3.62 (d, J=14.5 Hz, 1H), 3.27-3.24 (m, 1H), 3.16-3.08 (m, 2H), 2.85-2.70 (m, 3H), 2.33 (s, 3H). ESI-MS m/z: 335.1 [M+H]$^+$.

EXAMPLE 66

(S)-3-hydroxy-4-methoxy-10-fluoro-5,7,8,13,13b, 14-hexahydroindolo[2',3': 3,4]pyrido[1,2-b]isoquinoline (AIM)

The titled product was prepared by the same procedure as that in example 1, except that 5-fluorotryptamine was used to replace thiophene-2-ethylamine.

$^1$H NMR (CDCl$_3$, 400 MHz): δ 7.20 (dd, J=8.0 Hz, 1H), 6.99 (dd, J=8.0 Hz, 1H), 6.70 (s, 1H), 6.62 (d, J=8.1, 1H), 6.56 (d, J=8.1, 1H), 4.11 (d, J=14.8 Hz, 1H), 3.85 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H), 2.33 (s, 3H). ESI-MS m/z: 339.1 [M+H]$^+$.

EXAMPLE 67

(S)-3-hydroxy-4-methoxy-11-methyl-5,7,8,13,13b, 14-hexahydroindolo[2',3':3,4]pyrido[1,2-b]isoquinoline (A1006)

The titled product was prepared by the same procedure as that in example 1, except that 6-methyltryptamine was used to replace thiophene-2-ethylamine.

$^1$H NMR (CDCl$_3$, 400 MHz): δ 7.11 (dd, J=8.0 Hz, 1H), 6.99 (dd, J=8.0 Hz, 1H), 6.70 (s, 1H), 6.60 (m, 2H), 4.08 (d, J=14.8 Hz, 1H), 3.85 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H), 2.25 (s, 3H). ESI-MS m/z: 335.1 [M+H]$^+$.

EXAMPLE 68

(S)-3-hydroxy-4,11-dimethoxy-5,7,8,13,13b,14-hexahydroindolo[2',3':3,4]pyrido[1,2-b]isoquinoline (AI007)

The titled product was prepared by the same procedure as that in example 1, except that 6-methoxytryptamine was used to replace thiophene-2-ethylamine.

$^1$H NMR (CDCl$_3$, 400 MHz): δ 6.99 (dd, J=8.0 Hz, 1H), 6.89 (dd, J=8.0 Hz, 1H), 6.60-6.56 (m, 2H), 6.43 (s, 1H), 4.15 (d, J=14.8 Hz, 1H), 3.90 (s, 3H), 3.85 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H). ESI-MS m/z: 351.1 [M+H]$^+$.

EXAMPLE 69

(S)-5,6,8,14,14a,15-hexahydro-[1,3]dioxolo[4,5-g] indolo[2',3':3,4]pyrido[1,2-b]isoquinoline (AI008)

The titled product was prepared by the same procedure as that in example 62, except that 3,4-methylenedioxyphenylacetic acid was used to replace 3,4-dimethoxyphenylacetic acid.

$^1$H NMR (CDCl$_3$, 400 MHz): δ 7.13-7.08 (m, 4H), 6.82 (s, 1H), 6.76 (s, 1H), 4.11 (d, J=14.8 Hz, 1H), 3.90 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H). ESI-MS m/z: 336.2 [M+H]$^+$.

EXAMPLE 70

(S)-3-hydroxy-2-methoxy-5,7,8,13,13b,14-hexahydroindolo[2',3':3,4]pyrido[1,2-b]isoquinoline (A1009)

The titled product was prepared by the same procedure as that in example 69, except that 3-methoxy 4-hydroxy phenylacetic acid was used to replace 3,4-methenedioxy phenylacetic acid.

$^1$H NMR (CDCl$_3$, 400 MHz): δ 7.13-7.08 (m, 4H), 6.82 (s, 1H), 6.76 (s, 1H), 4.11 (d, J=14.8 Hz, 1H), 3.92 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H). ESI-MS m/z: 321.3 [M+H]$^+$.

EXAMPLE 71

(S)-2-hydroxy-3-methoxy-5,7,8,13,13b,14-hexahydroindolo[2',3':3,4]pyrido[1,2-b]isoquinoline (AI010)

The titled product was prepared by the same procedure as that in example 69, except that 3-hydroxy 4-methoxy phenylacetic acid was used to replace 3,4-methenedioxy phenylacetic acid.

$^1$H NMR (CDCl$_3$, 400 MHz): δ 7.13-7.08 (m, 4H), 6.82 (s, 1H), 6.76 (s, 1H), 4.11 (d, J=14.8 Hz, 1H), 3.90 (s, 3H), 3.70 (dd, J=10.8 Hz, J=3.8 Hz, 1H), 3.62 (d, J=14.5 Hz, 1H), 3.27-3.24 (m, 1H), 3.16-3.08 (m, 2H), 2.85-2.70 (m, 3H). ESI-MS m/z: 321.3 [M+H]$^+$.

EXAMPLE 72

(S)-2,8-dimethoxy-9-hydroxy-4,7,12,12a-tetrahydro-5H-benzo[g]pyrrolo[2,3-a]quinolizine (AP001)

The titled product was prepared by the same procedure as that in example 1, except that 5-methoxy-3-pyrrolecarboxaldehyde was used to replace 2-thienal.

$^1$H NMR (CDCl$_3$, 400 MHz): δ 6.65 (d, J=7.5, 1H), 6.54 (d, J=7.5, 1H), 5.76 (s, 1H), 4.11 (d, J=14.8 Hz, 1H), 3.85 (s, 3H), 3.80 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 3H). ESI-MS m/z: 301.1 [M+H]$^+$.

EXAMPLE 73

(S)-3,9-dimethoxy-10-hydroxy-5,8,13,13a-tetrahydro-6H-benzo[g]pyrido[2,3-a]quinolizine (AP002)

The titled product was prepared by the same procedure as that in example 1, except that 5-methoxy-3-pyridinecarboxaldehyde was used to replace 2-thienal.

$^1$H NMR (CDCl$_3$, 400 MHz): δ 8.12 (d, J=7.4, 1H), 7.40 (s, 1H), 6.65 (d, J=8.0, 1H), 6.54 (d, J=8.0, 1H), 5.76 (s, 1H), 4.11 (d, J=14.8 Hz, 1H), 3.85 (s, 3H), 3.80 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 3H). ESI-MS m/z: 313.1 [M+H]$^+$.

EXAMPLE 74

(S)-2,10-dihydroxy-3,9-dimethoxy-5,8,13,13a-tetrahydro-6H-benzo[g]pyrido[2,3-a]quinolizine (AP003)

The titled product was prepared by the same procedure as that in example 1, except that 5-methoxy-6-hydroxy-3-pyridinecarboxaldehyde was used to replace 2-thienal.
$^1$H NMR (CDCl$_3$, 400 MHz): δ 7.33 (s, 1H), 6.65 (d, J=8.0, 1H), 6.54 (d, J=8.0, 1H), 4.11 (d, J=14.8 Hz, 1H), 3.85 (s, 3H), 3.80 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 3H). ESI-MS m/z: 329.1 [M+H]$^+$.

EXAMPLE 75

(S)-2,8-dimethoxy-9-hydroxy-4,7,12,12a-tetrahydro-5H-benzo[g]pyrrolo[3,2-a]quinolizine (AP004)

The titled product was prepared by the same procedure as that in example 1, except that 5-methoxy-2-pyrrolecarboxaldehyde was used to replace 2-thienal.
$^1$H NMR (CDCl$_3$, 400 MHz): δ 6.68 (d, J=7.4, 1H), 6.60 (d, J=7.4, 1H), 5.98 (s, 1H), 4.11 (d, J=14.8 Hz, 1H), 3.85 (s, 3H), 3.80 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 3H). ESI-MS m/z: 301.1 [M+H]$^+$.

EXAMPLE 76

(S)-3,9-dimethoxy-6,8,13,13a-tetrahydro-5H-isoquinolino[3,2-1][1,6]naphthyridin-10-ol (AP005)

The titled product was prepared by the same procedure as that in example 1, except that 6-methoxy-2-pyridinecarboxaldehyde was used to replace 2-thienal.
$^1$H NMR (CDCl$_3$, 400 MHz): δ 7.68 (d, J=7.4, 1H), 6.65 (d, J=8.0, 1H), 6.54 (d, J=8.0, 1H), 6.43 (d, J=7.4, 1H), 4.11 (d, J=14.8 Hz, 1H), 3.85 (s, 3H), 3.80 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 3H). ESI-MS m/z: 313.1 [M+H]$^+$.

EXAMPLE 77

(S)-3,9-dimethoxy-6,8,13,13a-tetrahydro-5H-isoquinolino[3,2-1][1,6]naphthyridine-2,10-diol (AP006)

The titled product was prepared by the same procedure as that in example 1, except that 5-hydroxy-6-methoxy-2-pyridinecarboxaldehyde was used to replace 2-thienal.
$^1$H NMR (CDCl$_3$, 400 MHz): δ 7.43 (s, 1H), 6.65 (d, J=8.0, 1H), 6.54 (d, J=8.0, 1H), 4.11 (d, J=14.8 Hz, 1H), 3.85 (s, 3H), 3.80 (s, 3H), 3.68 (dd, J=10.8 Hz, J=3.8 Hz, 1H), 3.54 (d, J=14.5 Hz, 1H), 3.27-3.24 (m, 1H), 3.16-3.08 (m, 2H), 2.85-2.70 (m, 3H). ESI-MS m/z: 329.1 [M+H]$^+$.

EXAMPLE 78

(S)-2-hydroxy-3-methoxy-5,8,12,12a-tetrahydro-6H-benzo[a]thieno[3,2-g]quinolizine (DS001)

78.1 Preparation of thiophene-2-acetic acid 1 g of ethyl thiophene-2-acetate was dissolved in 4 mL of ethanol, added with 8 ml of 4N NaOH aqueous solution, and agitated at room temperature for 1 hour. The reaction mixture was adjusted with 1N HCl aqueous solution to a pH of 1, and extracted with dichloromethane. The organic phase was evaporated to dryness to give an oily product, thiophene-2-acetic acid. Yield, about 100%.
ESI-MS m/z: 141.0 [M–H]$^-$.

78.2 Preparation of 3-methoxy-4-benzyloxybenzaldehyde 10 g of 3-methoxy-4-hydroxybenzaldehyde was dissolved in 100 mL of acetone, added with anhydrous K$_2$CO$_3$ (3 eq), followed by dropwise addition of benzylbromide (1.1 eq) under agitating. Then, the mixture was placed in an oil bath and refluxed for 6 hours. After the reaction was completed, the reaction mixture was vacuum filtered and the filtrate was evaporated to dryness. Saturated NaHCO$_3$ aqueous solution was added, and the resultant mixture was extracted with dichloromethane. The organic phase was evaporated to dryness to give the product. Yield, 95%.
$^1$H NMR (CDCl$_3$, 400 MHz): δ7.50-7.40 (m, 5H), 7.25 (s, 1H), 7.10 (s, 1H), 5.11 (s, 2H), 3.85 (s, 3H). ESI-MS m/z: 243.0 [M+H]$^+$.

78.3 Preparation of 1-benzyloxy-2-methoxy-4-(2-nitrovinyl)benzene

The titled product was prepared by the same procedure as that in step 1.1 of example 1, except that the product obtained from the last step was used to replace 2-thienal.
$^1$H NMR (CDCl$_3$, 400 MHz): δ 7.50-7.40 (m, 5H), 7.25 (s, 1H), 7.20 (d, J=11.8 Hz, 1H), 7.09 (d, J=11.8 Hz, 1H), 6.95 (s, 1H), 5.11 (s, 2H), 3.85 (s, 3H). ESI-MS m/z: 286.0 [M+H]$^+$.

78.4 Preparation of 3-methoxy-4-benzyloxy phenylethylamine

The titled product was prepared by the same procedure as that in step 1.2 of example 1, except that the product obtained from the last step was used to replace 2-(2-nitrovinyl)thiophene.
$^1$H NMR (CDCl$_3$, 400 MHz): δ 7.50-7.40 (m, 5H), 6.83 (d, J=8.0 Hz, 1H), 6.74 (d, J=8.0 Hz, 1H), 6.77 (s, 1H), 6.95 (s, 1H), 5.11 (s, 2H), 3.85 (s, 3H), 2.88 (t, J=12.0 Hz, 2H), 2.57 (t, J=12.0 Hz, 2H). ESI-MS m/z: 258.1 [M+H]$^+$.

78.5 Preparation of N-(3-methoxy-4-benzyloxy phenylethyl)thiophene-2-acetamide The titled product was prepared by the same procedure as that in step 31.1 of example 31, except that the product obtained from the last step was used to replace thiophene-2-ethylamine and 3-methoxy-4-benzyloxyphenylacetic acid was used to replace 2,5-dimethoxyphenylacetic acid.
$^1$H NMR (CDCl$_3$, 400 MHz): δ 7.43-7.35 (m, 6H), 6.93 (d, J=7.8 Hz, 1H), 6.84 (m, 2H), 6.80 (s, 1H), 6.74 (s, 1H), 5.21 (s, 6H), 3.87 (s, 3H), 3.45 (s, 1H), 3.32 (t, J=12.0 Hz, 2H), 2.78 (t, J=12.0 Hz, 2H). ESI-MS m/z: 382.1 [M+H]$^+$.

78.6 Preparation of 6-methoxy-7-benzyloxy-(thiophene-2-methyl)-3,4-dihydro-isoquinoline The titled product was prepared by the same procedure as that in step 1.10 of example 1, except that the product obtained from the last step was used to replace N-thienyl-ethyl-2-acetyloxy-3-methoxy-4-benzyloxyphenylacetamide.
ESI-MS m/z: 364.1 [M+H]$^+$.

78.7 Preparation of (S)-6-methoxy-7-benzyloxy-1-(thiophene-2-methyl)-1,2,3,4-tetrahydro-isoquinoline The titled product was prepared by the same procedure as that in step 1.11 of example 1, except that the product obtained from the last step was used to replace 2-methoxy-3-benzyloxy-6-((6,7-dihydro-thieno(3,2-c)pyridin-4-yl)-methyl)-benzyl acetate.
ESI-MS m/z: 366.1 [M+H]$^+$.

78.8 Preparation of (S)-2-benzyloxy-3-methoxy-5,8,12,12a-tetrahydro-6H-benzo[a]thieno[3,2-g]quinolizine The titled product was prepared by the same procedure as that in step 31.2 of example 31, except that the product obtained from the last step was used to replace (S)-4-(2,5-dimethoxy benzyl)-4,5,6,7-tetrahydro-thieno(3,2-c)pyridine.
$^1$H NMR (CDCl$_3$, 400 MHz): δ 7.45-7.38 (m, 5H), 6.68 (s, 1H), 6.58 (s, 1H), 6.42 (s, 1H), 6.74 (s, 1H), 5.21 (s, 2H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 378.1 [M+H]$^+$.

78.9 Preparation of (S)-2-hydroxy-3-methoxy-5,8,12,12a-tetrahydro-6H-benzo[a]thieno[3,2-g]quinolizine (DS001)

The titled product was prepared by the same procedure as that in step 1.14 of example 1, except that the product obtained from the last step was used to replace (S)-4-(2-chloromethyl-3-methoxy-4-benzyloxy)-4,5,6,7-tetrahydro-thieno(3,2-c)pyridine).
$^1$H NMR (CDCl$_3$, 400 MHz): δ 710 (d, J=5.1 Hz, 1H), 6.79 (s, 1H), 6.75 (s, 1H), 6.59 (d, J=5.1 Hz, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 288.1 [M+H]$^+$.

EXAMPLE 79

(R)-2-hydroxy-3-methoxy-5,8,12,12a-tetrahydro-6H-benzo[a]thieno[3,2-g]quinolizine (DS002)

The titled product was prepared by the same procedure as that in example 78, except that (S,S)-Noyori catalyst was used to replace (R,R)-Noyori catalyst.
$^1$H NMR (CDCl$_3$, 400 MHz): δ 7.10 (d, J=5.1 Hz, 1H), 6.78 (s, 1H), 6.74 (s, 1H), 6.59 (d, J=5.1 Hz, 1H), 4.00 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 288.1 [M+H]$^+$.

EXAMPLE 80

(S)-2-hydroxy-3-methoxy-10-ethyl-5,8,12,12a-tetrahydro-6H-benzo[a]thieno[3,2-g]quinolizine (DS003)

80.1 Preparation of ethyl 5-acetylthiophene-2-acetate

Ethyl thiophene-2-acetate (1.7 g) and acetyl chloride (1.2 eq) were dissolved in anhydours dichloromethane (50 mL), cooled to 0° C., and added with anhydrous AlCl$_3$ (1.2 eq) in batches. After that, the reaction mixture was placed at room temperature to further react for 2 hours. After the reaction was completed, the reaction mixture was cooled to 0° C., added slowly with a certain amount of 1N HCl aqueous solution, and extracted triply with dichloromethane. The organic phase was evaporated to dryness to give the product.
$^1$H NMR (300 MHz, CDCl$_3$): δ 7.54 (d, J=3.6 Hz, 1H), 6.96 (d, J=3.6 Hz, 1H), 4.18 (q, J=7.2 Hz, 2H), 3.83 (s, 2H), 2.51 (s, 3H), 1.27 (t, J=7.2 Hz, 3H). ESI-MS m/z: 213.0 [M+H]$^+$.

80.2 Preparation of ethyl 5-ethylthiophene-2-acetate 1.06 g of ethyl 5-acetylthiophene-2-acetate was dissolved in 5 mL trifluoroacetic acid, added slowly with 4 eq of triethylsilane at room temperature and reacted overnight. After the reaction was completed, the solvent was evaporated and purification was preformed by column chromatography.
$^1$H NMR (300 MHz, CDCl$_3$): δ 6.84 (d, J=3.6 Hz, 1H), 6.76 (d, J=3.6 Hz, 1H), 4.16 (q, J=7.2 Hz, 2H), 3.83 (s, 2H), 2.82 (q, J=7.2, 2H), 1.29-1.26 (m, 6H). ESI-MS m/z: 199.0 [M+H]$^+$.

80.3 Preparation of 5-ethylthiophene-2-acetic acid

The titled product was prepared by the same procedure as that in step 78.1 of example 78, except that the product obtained from the last step was used to replace ethyl thiophene-2-acetate.
$^1$H NMR (300 MHz, CDCl$_3$): δ 6.84 (d, J=3.6 Hz, 1H), 6.76 (d, J=3.6 Hz, 1H), 3.53 (s, 2H), 2.82 (q, J=7.2 Hz, 2H), 1.26 (t, J=7.2 Hz, 3H). ESI-MS m/z: 169.0 [M−H]$^+$.

80.4 Preparation of (S)-2-hydroxy-3-methoxy-10-ethyl-5,8,12,12a-tetrahydro-6H-benzo[a]thieno[3,2-g]quinolizine (DS003)

The titled product was prepared by the same procedure as that in example 78, except that the product obtained from the last step was used to replace thiophene-2-acetic acid.
$^1$H NMR (CDCl$_3$, 400 MHz): δ 6.80 (s, 1H), 6.75 (s, 1H), 6.59 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 3H), 2.69-2.60 (m, 2H), 1.25 (t, J=7.2 Hz, 3H). ESI-MS m/z: 316.1 [M+H]$^+$.

EXAMPLE 81

(R)-2-hydroxy-3-methoxy-10-ethyl-5,8,12,12a-tetrahydro-6H-benzo[a]thieno[3,2-g]quinolizine (DS004)

The titled product was prepared by the same procedure as that in example 80, except that (S,S)-Noyori catalyst was used to replace (R,R)-Noyori catalyst.
$^1$H NMR (CDCl$_3$, 400 MHz): δ 6.79 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.90-2.81 (m, 3H), 2.69-2.60 (m, 2H), 1.25 (t, J=7.2 Hz, 3H). ESI-MS m/z: 316.1 [M+H]$^+$.

EXAMPLE 82

(S)-2-hydroxy-3-methoxy-10-n-propyl-5,8,12,12a-tetrahydro-6H-benzo[a]thieno[3,2-g]quinolizine (DS005)

The titled product was prepared by the same procedure as that in example 80, except that propionyl chloride was used to replace acetyl chloride.

$^1$H NMR (CDCl$_3$, 400 MHz): δ 6.78 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.90-2.81 (m, 3H), 2.69-2.60 (m, 2H), 1.65 (m, 2H), 1.25 (t, J=7.2 Hz, 3H). ESI-MS m/z: 330.1 [M+H]$^+$.

EXAMPLE 83

(S)-2-hydroxy-3-methoxy-10-(2-methylpropyl)-5,8,12,12a-tetrahydro-6H-benzo[a]thieno[3,2-g]quinolizine (DS006)

The titled product was prepared by the same procedure as that in example 80, except that 2-methylpropionyl chloride was used to replace acetyl chloride.

$^1$H NMR (CDCl$_3$, 400 MHz): δ 6.79 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.90-2.81 (m, 3H), 2.69-2.60 (m, 2H), 1.82 (m, 1H), 0.91-0.89 (m, 6H). ESI-MS m/z: 344.1 [M+H]$^+$.

EXAMPLE 84

(S)-2-hydroxy-3-methoxy-10-n-butyl-5,8,12,12a-tetrahydro-6H-benzo[a]thieno[3,2-g]quinolizine (DS007)

The titled product was prepared by the same procedure as that in example 80, except that n-butyryl chloride was used to replace acetyl chloride.

$^1$H NMR (CDCl$_3$, 400 MHz): δ 6.81 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.85-2.74 (m, 3H), 2.69-2.60 (m, 2H), 1.62 (m, 2H), 1.32 (m, 2H), 0.90 (t, J=7.2 Hz, 3H). ESI-MS m/z: 344.1

EXAMPLE 85

(S)-2-hydroxy-3-methoxy-10-(3-methylbutyl)-5,8,12,12a-tetrahydro-6H-benzo[a]thieno[3,2-g]quinolizine (DS008)

The titled product was prepared by the same procedure as that in example 80, except that 3-methylbutyryl chloride was used to replace acetyl chloride.

$^1$H NMR (CDCl$_3$, 400 MHz): δ 6.80 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.85-2.74 (m, 3H), 2.69-2.60 (m, 2H), 1.62-1.58 (m, 3H), 0.90 (m, 6H). ESI-MS m/z: 358.1 [M+H]$^+$.

EXAMPLE 86

(S)-2-hydroxy-3-methoxy-10-n-amyl-5,8,12,12a-tetrahydro-6H-benzo[a]thieno[3,2-g]quinolizine (DS009)

The titled product was prepared by the same procedure as that in example 80, except that valeryl chloride was used to replace acetyl chloride.

$^1$H NMR (CDCl$_3$, 400 MHz): δ 6.79 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.85-2.74 (m, 3H), 2.69-2.60 (m, 2H), 1.62-1.58 (m, 2H), 1.32-1.28 (m, 4H), 0.90 (t, J=7.2 Hz, 3H). ESI-MS m/z: 358.1 [M+H]$^+$.

EXAMPLE 87

(S)-2-hydroxy-3-methoxy-10-(4-methylamyl)-5,8,12,12a-tetrahydro-6H-benzo[a]thieno[3,2-g]quinolizine (DS010)

The titled product was prepared by the same procedure as that in example 80, except that 4-methylvaleryl chloride was used to replace acetyl chloride.

$^1$H NMR (CDCl$_3$, 400 MHz): δ 6.79 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.85-2.74 (m, 3H), 2.69-2.60 (m, 2H), 1.62-1.58 (m, 3H), 1.28-1.25 (m, 2H), 0.90 (t, J=7.2 Hz, 6H). ESI-MS m/z: 372.1 [M+H]$^+$.

EXAMPLE 88

(S)-2-hydroxy-3-methoxy-10-cyclopropylmethyl-5,8,12,12a-tetrahydro-6H-benzo[a]thieno[3,2-g]quinolizine (DS011)

The titled product was prepared by the same procedure as that in example 80, except that cyclopropylformyl chloride was used to replace acetyl chloride.

$^1$H NMR (CDCl$_3$, 400 MHz): δ 6.79 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.85-2.74 (m, 3H), 2.69-2.60 (m, 2H), 0.94 (m, 1H), 0.51-0.55 (m, 2H), 0.19-0.47 (m, 2H). ESI-MS m/z: 342.1 [M+H]$^+$.

EXAMPLE 89

(S)-2-hydroxy-3-methoxy-10-cyclobutylmethyl-5,8,12,12a-tetrahydro-6H-benzo[a]thieno[3,2-g]quinolizine (DS012)

The titled product was prepared by the same procedure as that in example 80, except that cyclobutylformyl chloride was used to replace acetyl chloride.

$^1$H NMR (CDCl$_3$, 400 MHz): δ 6.79 (s, 1H), 6.75 (s, 1H), 6.59 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.85-2.74 (m, 3H), 2.69-2.60 (m, 2H), 2.34 (m, 1H), 2.05-1.78 (m, 6H). ESI-MS m/z: 356.1 [M+H]$^+$.

EXAMPLE 90

(S)-2-hydroxy-3-methoxy-10-(2-chloroethyl)-5,8,12,12a-tetrahydro-6H-benzo[a]thieno[3,2-g]quinolizine (DS013)

The titled product was prepared by the same procedure as that in example 80, except that 2-chloroacetyl chloride was used to replace acetyl chloride.

$^1$H NMR (CDCl$_3$, 400 MHz): δ 6.79 (s, 1H), 6.74 (s, 1H), 6.59 (s, 1H), 4.00 (d, J=14.8 Hz, 1H), 3.87 (s, 3H), 3.56 (m, 3H), 3.51 (d, J=14.8 Hz, 1H), 2.85-2.74 (m, 3H), 2.69-2.60 (m, 2H), 2.34 (m, 1H), 1.90 (m, 2H). ESI-MS m/z: 350.1 [M+H]$^+$.

EXAMPLE 91

(12aS)-2-hydroxy-3-methoxy-10-(2-chloropropyl)-5,8,12,12a-tetrahydro-6H-benzo[a]thieno[3,2-g]quinolizine (DS014)

The titled product was prepared by the same procedure as that in example 80, except that 2-chloropropionyl chloride was used to replace acetyl chloride.

$^1$H NMR (CDCl$_3$, 400 MHz): δ 6.79 (s, 1H), 6.74 (s, 1H), 6.59 (s, 1H), 4.00 (d, J=14.8 Hz, 1H), 3.87 (s, 3H), 3.56 (m, 3H), 3.51 (d, J=14.8 Hz, 1H), 3.25-3.08 (m, 3H), 2.85-2.74 (m, 3H), 2.69-2.60 (m, 2H), 2.34 (m, 1H), 2.05-1.78 (m, 6H), 1.64 (t, J=7.2 Hz, 3H). ESI-MS m/z: 364.1 [M+H]$^+$.

EXAMPLE 92

(S)-2-hydroxy-3-methoxy-10-(3-chloropropyl)-5,8,12,12a-tetrahydro-6H-benzo[a]thieno[3,2-g]quinolizine (DS015)

The titled product was prepared by the same procedure as that in example 80, except that 3-chloropropionyl chloride was used to replace acetyl chloride.

$^1$H NMR (CDCl$_3$, 400 MHz): δ 6.79 (s, 1H), 6.74 (s, 1H), 6.59 (s, 1H), 4.00 (d, J=14.8 Hz, 1H), 3.87 (s, 3H), 3.56 (m, 3H), 3.51 (d, J=14.8 Hz, 1H), 3.25-3.08 (m, 3H), 2.85-2.74 (m, 5H), 2.69-2.60 (m, 2H), 1.90 (m, 2H). ESI-MS m/z: 364.1 [M+H]$^+$.

EXAMPLE 93

(S)-2-hydroxy-3-methoxy-10-(4-chlorobutyl)-5,8,12,12a-tetrahydro-6H-benzo[a]thieno[3,2-g]quinolizine (DS016)

The titled product was prepared by the same procedure as that in example 80, except that 4-chlorobutyryl chloride was used to replace acetyl chloride.

$^1$H NMR (CDCl$_3$, 400 MHz): δ 6.79 (s, 1H), 6.74 (s, 1H), 6.59 (s, 1H), 4.00 (d, J=14.8 Hz, 1H), 3.87 (s, 3H), 3.56 (m, 3H), 3.51 (d, J=14.8 Hz, 1H), 3.25-3.08 (m, 3H), 2.85-2.74 (m, 5H), 2.69-2.60 (m, 2H), 1.77 (m, 2H), 1.59 (m, 2H). ESI-MS m/z: 378.1 [M+H]$^+$.

EXAMPLE 94

(S)-2-hydroxy-3-methoxy-10-(2,2,2-trifluoroethyl)-5,8,12,12a-tetrahydro-6H-benzo[a]thieno[3,2-g]quinolizine (DS017)

The titled product was prepared by the same procedure as that in example 80, except that 2,2,2-trifluoroacetyl chloride was used to replace acetyl chloride.

$^1$H NMR (CDCl$_3$, 400 MHz): δ 6.80 (s, 1H), 6.73 (s, 1H), 6.59 (s, 1H), 4.00 (d, J=14.8 Hz, 1H), 3.87 (s, 3H), 3.54 (d, J=10.8 Hz, 1H), 3.51 (d, J=14.8 Hz, 1H), 3.25-3.08 (m, 3H), 2.85-2.70 (m, 5H). ESI-MS m/z: 370.1 [M+H]$^+$.

EXAMPLE 95

(S)-2-hydroxy-3-methoxy-10-(3,3,3-trifluoropropyl)-5,8,12,12a-tetrahydro-6H-benzo[a]thieno[3,2-g]quinolizine (DS018)

The titled product was prepared by the same procedure as that in example 80, except that 3,3,3-trifluoropropionyl chloride was used to replace acetyl chloride.

$^1$H NMR (CDCl$_3$, 400 MHz): δ 6.80 (s, 1H), 6.73 (s, 1H), 6.59 (s, 1H), 4.00 (d, J=14.8 Hz, 1H), 3.87 (s, 3H), 3.54 (d, J=10.8 Hz, 1H), 3.51 (d, J=14.8 Hz, 1H), 3.25-3.08 (m, 3H), 2.85-2.70 (m, 5H), 2.14 (m, 2H). ESI-MS m/z: 370.1 [M+H]$^+$.

EXAMPLE 96

(S)-2-hydroxy-3-methoxy-10-(3,3-difluoropropyl)-5,8,12,12a-tetrahydro-6H-benzo[a]thieno[3,2-g]quinolizine (DS019)

The titled product was prepared by the same procedure as that in example 80, except that 3,3-difluoropropionyl chloride was used to replace acetyl chloride.

$^1$H NMR (CDCl$_3$, 400 MHz): δ 6.80 (s, 1H), 6.73 (s, 1H), 6.59 (s, 1H), 5.15 (m, 1H), 4.11 (d, J=14.8 Hz, 1H), 3.87 (s, 3H), 3.54 (d, J=10.8 Hz, 1H), 3.51 (d, J=14.8 Hz, 1H), 3.25-3.08 (m, 3H), 2.85-2.70 (m, 5H), 1.98 (m, 2H). ESI-MS m/z: 366.1 [M+H]$^+$.

EXAMPLE 97

(S)-2,3-dimethoxy-5,8,12,12a-tetrahydro-6H-benzo[a]thieno[3,2-g]quinolizine (DS020)

The titled product was prepared by the same procedure as that in example 78, except that 3,4-dimethoxyphenylacetic acid was used to replace 3-methoxy-4-benzyloxy-phenylacetic acid.

$^1$H NMR (CDCl$_3$, 400 MHz): δ 7.10 (s, 1H), 6.79 (s, 1H), 6.75 (s, 1H), 6.59 (s, 1H), 4.05 (d, J=14.8 Hz, 1H), 3.87 (s, 6H), 3.56 (d, J=10.8 Hz, 1H), 3.48 (d, J=14.9 Hz, 1H), 325-3.08 (m, 3H), 2.90-2.81 (m, 1H), 2.69-2.60 (m, 2H). ESI-MS m/z: 302.1 [M+H]$^+$.

EXAMPLE 98

(S)-2,3-dimethoxy-10-ethyl-5,8,12,12a-tetrahydro-6H-benzo[a]thieno[3,2-g]quinolizine (DS021)

The titled product was prepared by the same procedure as that in example 80, except that 3,4-dimethoxyphenylacetic acid was used to replace 3-methoxy-4-benzyloxyphenylacetic acid.

$^1$H NMR (CDCl$_3$, 400 MHz): δ 6.80 (s, 1H), 6.75 (s, 1H), 6.59 (s, 1H), 4.05 (d, J=14.8 Hz, 1H), 3.87 (s, 6H), 3.56 (d, J=10.8 Hz, 1H), 3.48 (d, J=14.9 Hz, 1H), 3.25-3.08 (m, 3H), 2.90-2.81 (m, 3H), 2.69-2.60 (m, 2H), 1.25 (t, J=7.2 Hz, 3H). ESI-MS m/z: 330.1 [M+H]⁺.

EXAMPLE 99

(S)-2,3-dimethoxy-10-(2-methylpropyl)-5,8,12,12a-tetrahydro-6H-benzo[a]thieno[3,2-g]quinolizine (DS022)

The titled product was prepared by the same procedure as that in example 98, except that 2-methylpropionyl chloride was used to replace acetyl chloride.

$^1$H NMR (CDCl$_3$, 400 MHz): δ 6.79 (s, 1H), 6.75 (s, 1H), 6.59 (s, 1H), 4.00 (d, J=14.8 Hz, 1H), 3.87 (s, 6H), 3.56 (d, J=10.8 Hz, 1H), 3.51 (d, J=14.8 Hz, 1H), 3.25-3.08 (m, 3H), 2.90-2.81 (m, 3H), 2.69-2.60 (m, 2H), 1.82 (m, 1H), 0.91-0.89 (m, 6H). ESI-MS m/z: 358.1 [M+H]⁺.

EXAMPLE 100

(S)-2,3-dimethoxy-10-(2-chloroethyl)-5,8,12,12a-tetrahydro-6H-benzo[a]thieno[3,2-g]quinolizine (DS023)

The titled product was prepared by the same procedure as that in example 98, except that 2-chloroacetyl chloride was used to replace acetyl chloride.

$^1$H NMR (CDCl$_3$, 400 MHz): δ 6.79 (s, 1H), 6.74 (s, 1H), 6.59 (s, 1H), 4.00 (d, J=14.8 Hz, 1H), 3.87 (s, 6H), 3.56 (m, 3H), 3.51 (d, J=14.8 Hz, 1H), 2.85-2.74 (m, 3H), 2.69-2.60 (m, 2H), 2.34 (m, 1H), 1.90 (m, 2H). ESI-MS m/z: 364.1 [M+H]⁺.

EXAMPLE 101

(S)-2,3-methylenedioxy-5,8,12,12a-tetrahydro-6H-benzo[a]thieno[3,2-g]quinolizine (DS024)

The titled product was prepared by the same procedure as that in example 78, except that 3,4-methylenedioxyphenylacetic acid was used to replace 3-methoxy-4-benzyloxyphenylacetic acid.

$^1$H NMR (CDCl$_3$, 400 MHz): δ 7.12 (s, 1H), 6.88 (s, 1H), 6.81 (s, 1H), 6.59 (s, 1H), 6.07 (s, 2H), 4.05 (d, J=14.8 Hz, 1H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 286.0 [M+H]⁺.

EXAMPLE 102

(S)-2,3-methylenedioxy-10-ethyl-5,8,12,12a-tetrahydro-6H-benzo[a]thieno[3,2-g]quinolizine (DS025)

The titled product was prepared by the same procedure as that in example 98, except that 3,4-methylenedioxyphenylacetic acid was used to replace 3,4-dimethoxyphenylacetic acid.

$^1$H NMR (CDCl$_3$, 400 MHz): δ 6.88 (s, 1H), 6.81 (s, 1H), 6.29 (s, 1H); 6.07 (s, 2H), 4.05 (d, J=14.8 Hz, 1H), 3.56 (d, J=10.8 Hz, 1H), 3.48 (d, J=14.9 Hz, 1H), 3.25-3.08 (m, 3H), 2.90-2.81 (m, 3H), 2.69-2.60 (m, 2H), 1.24 (t, J=7.2 Hz, 3H). ESI-MS m/z: 314.1 [M+H]⁺.

EXAMPLE 103

(S)-2,3-methylenedioxy-10-(2-methylpropyl)-5,8,12,12a-tetrahydro-6H-benzo[a]thieno[3,2-g]quinolizine (DS026)

The titled product was prepared by the same procedure as that in example 102, except that 2-methylpropionyl chloride was used to replace acetyl chloride.

$^1$H NMR (CDCl$_3$, 400 MHz): δ 6.88 (s, 1H), 6.81 (s, 1H), 6.29 (s, 1H), 6.07 (s, 2H), 4.05 (d, J=14.8 Hz, 1H), 3.56 (d, J=10.8 Hz, 1H), 3.48 (d, J=14.9 Hz, 1H), 3.25-3.08 (m, 3H), 2.90-2.81 (m, 3H), 2.69-2.60 (m, 2H), 1.81 (m, 1H), 0.94 (d, J=7.2 Hz, 6H). ESI-MS m/z: 342.1 [M+H]⁺.

EXAMPLE 104

(S)-2,3-methylenedioxy-10-(2-chloroethyl)-5,8,12,12a-tetrahydro-6H-benzo[a]thieno[3,2-g]quinolizine (DS027)

The titled product was prepared by the same procedure as that in example 102, except that 2-chloroacetyl chloride was used to replace acetyl chloride.

$^1$H NMR (CDCl$_3$, 400 MHz): δ 6.88 (s, 1H), 6.81 (s, 1H), 6.30 (s, 1H), 6.07 (s, 2H), 4.05 (d, J=14.8 Hz, 1H), 3.65-3.56 (m, 3H), 3.48 (d, J=14.9 Hz, 1H), 3.25-3.08 (m, 3H), 2.90-2.81 (m, 3H), 2.69-2.60 (m, 2H). ESI-MS m/z: 348.1 [M+H]⁺.

EXAMPLE 105

(S)-2-hydroxy-3-methoxy-10-methyl-5,8,12,12a-tetrahydro-6H-benzo[a]thieno[3,2-g]quinolizine (DS028)

The titled product was prepared by the same procedure as that in example 80, except that ethyl 5-methylthiophene-2-acetate was used to replace ethyl 5-ethylthiophene-2-acetate.

$^1$H NMR (CDCl$_3$, 400 MHz): δ 6.78 (s, 1H), 6.75 (s, 1H), 6.59 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H), 2.35 (s, 3H). ESI-MS m/z: 302.0 [M+H]⁺.

EXAMPLE 106

(S)-2-hydroxy-3-methoxy-10-(2-chloromethyl)-5,8,12,12a-tetrahydro-6H-benzo[a]thieno[3,2-g]quinolizine (DS029)

The titled product was prepared by the same procedure as that in example 80, except that ethyl 5-chloromethylthiophene-2-acetate was used to replace ethyl 5-ethylthiophene-2-acetate.

$^1$H NMR (CDCl$_3$, 400 MHz): δ 6.79 (s, 1H), 6.75 (s, 1H), 6.59 (s, 1H), 4.64 (s, 2H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 302.0 [M+H]⁺.

EXAMPLE 107

(S)-2-hydroxy-3-methoxy-10-(2-fluoro methyl)-5,8,12,12a-tetrahydro-6H-benzo[a]thieno[3,2-g]quinolizine (DS030)

The titled product was prepared by the same procedure as that in example 80, except that ethyl 5-fluoromethylthiophene-2-acetate was used to replace ethyl 5-ethylthiophene-2-acetate.

¹H NMR (CDCl₃, 400 MHz): δ 6.79 (s, 1H), 6.75 (s, 1H), 6.59 (s, 1H), 5.18 (d, J=16 Hz, 2H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 320.0 [M+H]⁺.

EXAMPLE 108

(S)-2-hydroxy-3-methoxy-10-(2-methylol)-5,8,12,12a-tetrahydro-6H-benzo[a]thieno[3,2-g]quinolizine (DS031)

The titled product was prepared by the same procedure as that in example 80, except that ethyl 5-methylolthiophene-2-acetate was used to replace ethyl 5-ethylthiophene-2-acetate.

¹H NMR (CDCl₃, 400 MHz): δ 6.79 (s, 1H), 6.75 (s, 1H), 6.59 (s, 1H), 4.80 (s, 2H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 318.1 [M+H]⁺.

EXAMPLE 109

(S)-2-hydroxy-3-methoxy-10-(methoxymethyl)-5,8,12,12a-tetrahydro-6H-benzo[a]thieno[3,2-g]quinolizine (DS032)

The titled product was prepared by the same procedure as that in example 80, except that ethyl 5-methoxymethylthiophene-2-acetate was used to replace ethyl 5-ethylthiophene-2-acetate.

¹H NMR (CDCl₃, 400 MHz): δ 6.79 (s, 1H), 6.75 (s, 1H), 6.59 (s, 1H), 4.63 (s, 2H), 4.05 (d, J=14.8 Hz, 1H), 3.87 (s, 3H), 3.56 (d, J=10.8 Hz, 1H), 3.48 (d, J=14.9 Hz, 1H), 3.30 (s, 3H), 3.25-108 (m, 3H), 2.90-2.81 (m, 1H), 2.69-2.60 (m, 2H). ESI-MS m/z: 332.1 [M+H]⁺.

EXAMPLE 110

(S)-2-hydroxy-3,10-dimethoxy-5,8,12,12a-tetrahydro-6H-benzo[a]thieno[3,2-g]quinolizine (DS033)

The titled product was prepared by the same procedure as that in example 80, except that ethyl 5-methoxythiophene-2-acetate was used to replace ethyl 5-ethylthiophene-2-acetate.

¹H NMR (CDCl₃, 400 MHz): δ 6.79 (s, 1H), 6.75 (s, 1H), 6.59 (s, 1H), 4.05 (d, J=14.8 Hz, 1H), 3.87 (s, 3H), 3.80 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 318.1 [M+H]+.

EXAMPLE 111

(S)-2-hydroxy-3-methoxy-9,10-dimethyl-5,8,12,12a-tetrahydro-6H-benzo[a]thieno[3,2-g]quinolizine (DS034)

The titled product was prepared by the same procedure as that in example 80, except that ethyl 4,5-dimethylthiophene-2-acetate was used to replace ethyl 5-ethylthiophene-2-acetate.

¹H NMR (CDCl₃, 400 MHz): δ 7.10 (s, 1H), 6.79 (s, 1H), 6.75 (s, 1H), 6.59 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H), 2.36 (s, 3H), 2.22 (s, 3H). ESI-MS m/z: 316.1 [M+H]⁺.

EXAMPLE 112

(S)-2-hydroxy-3-methoxy-9-methyl-5,8,12,12a-tetrahydro-6H-benzo[a]thieno[3,2-g]quinolizine (DS035)

The titled product was prepared by the same procedure as that in example 80, except that ethyl 4-methylthiophene-2-acetate was used to replace ethyl 5-ethylthiophene-2-acetate.

¹H NMR (CDCl₃, 400 MHz): δ 7.02 (s, 1H), 6.79 (s, 1H), 6.75 (s, 1H), 6.59 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H), 2.20 (s, 3H). ESI-MS m/z: 302.0 [M+H]⁺.

EXAMPLE 113

(S)-2-hydroxy-3-methoxy-9-ethyl-5,8,12,12a-tetrahydro-6H-benzo[a]thieno[3,2-g]quinolizine (DS036)

The titled product was prepared by the same procedure as that in example 80, except that ethyl 4-ethylthiophene-2-acetate was used to replace ethyl 5-ethylthiophene-2-acetate.

¹H NMR (CDCl₃, 400 MHz): δ 7.02 (s, 1H), 6.79 (s, 1H), 6.75 (s, 1H), 6.59 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 4H), 1.23 (t, J=7.2 Hz, 3H). ESI-MS m/z: 302.0 [M+H]⁺.

EXAMPLE 114

(12aS)-2-hydroxy-3-methoxy-8-methyl-10-(2-methylpropyl)-5,8,12,12a-tetrahydro-6H-benzo[a]thieno[3,2-g]quinolizine (DS037)

The titled product was prepared by the same procedure as that in example 103, except that acetaldehyde was used to replace formaldehyde.

¹H NMR (CDCl₃, 400 MHz): δ 6.79 (s, 1H), 6.75 (s, 1H), 6.59 (s, 1H), 4.08 (d, J=14.8 Hz, 1H), 3.99 (q, J=6.8 Hz, 1H), 3.87 (s, 3H), 3.56 (d, J=10.8 Hz, 1H), 3.51 (d, J=14.8 Hz, 1H), 3.25-3.08 (m, 2H), 2.90-2.81 (m, 2H), 2.69-2.60 (m, 2H), 1.82 (m, 1H), 1.28 (d, J=6.8 Hz, 3H), 0.91-0.89 (m, 6H). ESI-MS m/z: 358.1 [M+H]⁺.

EXAMPLE 115

(12aS)-2-hydroxy-3-methoxy-5-methyl-10-(2-methylpropyl)-5,8,12,12a-tetrahydro-6H-benzo[a]thieno[3,2-g]quinolizine (DS038)

The titled product was prepared by the same procedure as that in example 83, except that 2-methyl-2-(3-methoxy-4-hydroxyphenyl)ethylamine was used to replace 3-methoxy-4-hydroxyphenylethylamine.

¹H NMR (CDCl₃, 400 MHz): δ 6.79 (s, 1H), 6.75 (s, 1H), 6.59 (s, 1H), 4.08 (d, J=14.8 Hz, 1H), 3.87 (s, 3H), 3.56 (d, J=10.8 Hz, 1H), 3.51 (d, J=14.8 Hz, 1H), 3.25-3.08 (m, 2H), 2.90-2.81 (m, 2H), 2.69-2.60 (m, 3H), 1.82 (m, 1H), 1.24 (d, J=6.8 Hz, 3H), 0.91-0.89 (m, 6H). ESI-MS m/z: 358.1 [M+H]⁺.

EXAMPLE 116

(12aS)-2-hydroxy-3-methoxy-6-methyl-10-(2-methylpropyl)-5,8,12,12a-tetrahydro-6H-benzo[a]thieno[3,2-g]quinolizine (DS039)

The titled product was prepared by the same procedure as that in example 83, except that 1-methyl-2-(3-methoxy-4-hydroxyphenyl)ethylamine was used to replace 3-methoxy-4-hydroxyphenylethyl amine.

1H NMR (CDCl$_3$, 400 MHz): δ 6.79 (s, 1H), 6.75 (s, 1H), 6.59 (s, 1H), 4.08 (d, J=14.8 Hz, 1H), 3.87 (s, 3H), 3.56 (d, J=10.8 Hz, 1H), 3.51 (d, J=14.8 Hz, 1H), 3.25-3.08 (m, 2H), 2.90-2.81 (m, 2H), 2.69-2.46 (m, 3H), 1.82 (m, 1H), 1.24 (d, J=6.8 Hz, 3H), 0.91-0.89 (m, 6H). ESI-MS m/z: 358.1 [M+H]$^+$.

EXAMPLE 117

(12aS)-2-hydroxy-3-methoxy-5-fluoro-10-(2-methylpropyl)-5,8,12,12a-tetrahydro-6H-benzo[a]thieno[3,2-g]quinolizine (DS040)

The titled product was prepared by the same procedure as that in example 83, except that 2-fluoro-2-(3-methoxy-4-hydroxyphenyl)ethylamine was used to replace 3-methoxy-4-hydroxyphenylethylamine.

$^1$H NMR (CDCl$_3$, 400 MHz): δ 6.78 (s, 1H), 6.74 (s, 1H), 6.56 (s, 1H), 4.72 (dt, J=17.8 Hz, J=6.9 Hz, 1H), 4.03 (d, J=14.8 Hz, 1H), 3.84 (s, 3H), 3.53 (d, J=10.8 Hz, 1H), 3.46 (d, J=14.8 Hz, 1H), 3.08-2.90 (m, 2H), 2.79-2.64 (m, 4H), 1.82 (m, 1H), 0.91-0.89 (m, 6H). ESI-MS m/z: 362.1 [M+H]$^+$.

EXAMPLE 118

(S)-2-hydroxy-3-methoxy-10-ethyl-5,8,12,12a-tetrahydro-6H-benzo[a]thieno[2,3-g]quinolizine (DS041)

The titled product was prepared by the same procedure as that in example 80, except that 5-ethylthiophene-3-acetic acid was used to replace 5-ethylthiophene-3-acetic acid.

$^1$H NMR (CDCl$_3$, 400 MHz): δ 6.65 (d, J=8.1, 1H), 6.54 (d, J=8.1, 1H), 6.24 (s, 1H), 3.95 (d, J=14.8 Hz, 1H), 3.88 (s, 3H), 3.68 (dd, J=10.8 Hz, J=3.8 Hz, 1H), 3.54 (d, J=14.5 Hz, 1H), 3.29-3.24 (m, 1H), 3.16-3.08 (m, 2H), 2.85-2.65 (m, 5H), 1.23 (t, J=7.2 Hz, 3H). ESI-MS m/z: 316.0 [M+H]$^+$.

EXAMPLE 119

(S)-2-hydroxy-3-methoxy-10-(2-chloroethyl)-5,8,12,12a-tetrahydro-6H-benzo[a]thieno[2,3-g]quinolizine (DS042)

The titled product was prepared by the same procedure as that in example 80, except that 5-(2-chloroethyl)thiophene-3-acetic acid was used to replace 5-ethylthiophene-2-acetic acid.

$^1$H NMR (CDCl$_3$, 400 MHz): δ 6.65 (d, J=8.1, 1H), 6.54 (d, J=8.1, 1H), 6.24 (s, 1H), 3.95 (d, J=14.8 Hz, 1H), 3.88 (s, 3H), 3.68-3.70 (m, 3H), 3.54 (d, J=14.5 Hz, 1H), 3.29-3.24 (m, 1H), 3.16-3.08 (m, 2H), 2.85-2.65 (m, 5H). ESI-MS m/z: 350.1 [M+H]$^+$.

EXAMPLE 120

(S)-2-hydroxy-3-methoxy-10-(2-methylpropyl)-5,8,12,12a-tetrahydro-6H-benzo[a]thieno[2,3-g]quinolizine (DS043)

The titled product was prepared by the same procedure as that in example 80, except that 5-(2-methyl propyl)thiophene-3-acetic acid was used to replace 5-ethylthiophene-2-acetic acid.

$^1$H NMR (CDCl$_3$, 400 MHz): δ 6.79 (s, 1H), 6.75 (s, 1H), 6.19 (s, 1H), 4.04 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.90-2.81 (m, 3H), 2.69-2.60 (m, 2H), 1.82 (m, 1H), 0.91-0.89 (m, 6H). ESI-MS m/z: 344.1 [M+H]$^+$.

EXAMPLE 121

(S)-2-hydroxy-3,10-dimethoxy-5,8,12,12a-tetrahydro-6H-benzo[a]thieno[3,2-g]quinolizine (DS044)

The titled product was prepared by the same procedure as that in example 80, except that 5-methoxythiophene-3-acetic acid was used to replace 5-ethylthiophene-2-acetic acid.

$^1$H NMR (CDCl$_3$, 400 MHz): δ 6.79 (s, 1H), 6.75 (s, 1H), 5.79 (s, 1H), 4.05 (d, J=14.8 Hz, 1H), 3.87 (s, 3H), 3.80 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 318.1 [M+H]$^+$.

EXAMPLE 122

(S)-2-hydroxy-3-methoxy-5,8,12,12a-tetrahydro-6H-benzo[a]furo[3,2-g]quinolizine (DF001)

The titled product was prepared by the same procedure as that in example 80, except that furan-2-acetic acid was used to replace 5-ethylthiophene-2-acetic acid.

$^1$H NMR (CDCl$_3$, 400 MHz): δ 7.10 (d, J=5.1 Hz, 1H), 6.79 (s, 1H), 6.75 (s, 1H), 6.19 (d, J=5.1 Hz, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 272.1 [M+H]$^+$.

EXAMPLE 123

(S)-2-hydroxy-3-methoxy-10-ethyl-5,8,12,12a-tetrahydro-6H-benzo[a]furo[3,2-g]quinolizine (DF002)

The titled product was prepared by the same procedure as that in example 80, except that 5-ethylfuran-2-acetic acid was used to replace 5-ethylthiophene-2-acetic acid.

$^1$H NMR (CDCl$_3$, 400 MHz): δ 6.80 (s, 1H), 6.75 (s, 1H), 6.19 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 3H), 2.69-2.60 (m, 2H), 1.25 (t, J=7.2 Hz, 3H). ESI-MS m/z: 300.1 [M+H]$^+$.

EXAMPLE 124

(S)-2-hydroxy-3-methoxy-10-(2-methylpropyl)-5,8,12,12a-tetrahydro-6H-benzo[a]furo[3,2-g]quinolizine (DF003)

The titled product was prepared by the same procedure as that in example 80, except that 5-(2-methylpropyl)furan-2-acetic acid was used to replace 5-ethylthiophene-2-acetic acid.

¹H NMR (CDCl₃, 400 MHz): δ 6.79 (s, 1H), 6.75 (s, 1H), 6.22 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.90-2.81 (m, 3H), 2.69-2.60 (m, 2H), 1.82 (m, 1H), 0.91-0.89 (m, 6H). ESI-MS m/z: 328.1 [M+H]⁺.

EXAMPLE 125

(S)-2-hydroxy-3-methoxy-10-cyclopropylmethyl-5,8,12,12a-tetrahydro-6H-benzo[a]furo[3,2-g]quinolizine (DF004)

The titled product was prepared by the same procedure as that in example 80, except that 5-cyclopropylmethylfuran-2-acetic acid was used to replace 5-ethylthiophene-2-acetic acid.

¹H NMR (CDCl₃, 400 MHz): δ 6.79 (s, 1H), 6.75 (s, 1H), 6.20 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.85-2.74 (m, 3H), 2.69-2.60 (m, 2H), 0.94 (m, 1H), 0.51-0.55 (m, 2H), 0.19-0.47 (m, 2H). ESI-MS m/z: 326.1 [M+H]⁺.

EXAMPLE 126

(S)-2-hydroxy-3-methoxy-10-(2-chloroethyl)-5,8,12,12a-tetrahydro-6H-benzo[a]furo[3,2-g]quinolizine (DF005)

The titled product was prepared by the same procedure as that in example 80, except that 5-(2-chloroethyl)furan-2-acetic acid was used to replace 5-ethylthiophene-2-acetic acid.

¹H NMR (CDCl₃, 400 MHz): δ 6.79 (s, 1H), 6.74 (s, 1H), 6.19 (s, 1H), 4.00 (d, J=14.8 Hz, 1H), 3.87 (s, 3H), 3.56 (m, 3H), 3.51 (d, J=14.8 Hz, 1H), 2.85-2.74 (m, 3H), 2.69-2.60 (m, 2H), 2.34 (m, 1H), 1.90 (m, 2H). ESI-MS m/z: 334.1 [M+H]⁺.

EXAMPLE 127

(S)-2-hydroxy-3,10-dimethoxy-5,8,12,12a-tetrahydro-6H-benzo[a]furo[3,2-g]quinolizine (DF006)

The titled product was prepared by the same procedure as that in example 80, except that 5-methoxyfuran-2-acetic acid was used to replace 5-ethylthiophene-2-acetic acid.

¹H NMR (CDCl₃, 400 MHz): δ 6.79 (s, 1H), 6.75 (s, 1H), 6.20 (s, 1H), 4.05 (d, J=14.8 Hz, 1H), 3.87 (s, 3H), 3.80 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 302.1 [M+H]⁺.

EXAMPLE 128

(S)-2-hydroxy-3-methoxy-10-ethyl-5,8,12,12a-tetrahydro-6H-benzo[a]furo[2,3-g]quinolizine (DF007)

The titled product was prepared by the same procedure as that in example 80, except that 5-ethylfuran-3-acetic acid was used to replace 5-ethylthiophene-2-acetic acid.

¹H NMR (CDCl₃, 400 MHz): δ 6.80 (s, 1H), 6.75 (s, 1H), 5.94 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 3H), 2.69-2.60 (m, 2H), 1.25 (t, J=7.2 Hz, 3H). ESI-MS m/z: 300.1 [M+H]⁺.

EXAMPLE 129

(S)-2-hydroxy-3-methoxy-10-(2-methylpropyl)-5,8,12,12a-tetrahydro-6H-benzo[a]furo[2,3-g]quinolizine (DF008)

The titled product was prepared by the same procedure as that in example 80, except that 5-(2-methylpropyl)furan-3-acetic acid was used to replace 5-ethylthiophene-2-acetic acid.

¹H NMR (CDCl₃, 400 MHz): δ 6.79 (s, 1H), 6.75 (s, 1H), 5.99 (s, 1H), 4.00 (d, J=14.8 Hz, 1H), 3.87 (s, 3H), 3.56 (d, J=10.8 Hz, 1H), 3.51 (d, J=14.8 Hz, 1H), 3.25-3.08 (m, 3H), 2.90-2.81 (m, 3H), 2.69-2.60 (m, 2H), 1.82 (m, 1H), 0.91-0.89 (m, 6H). ESI-MS m/z: 328.1 [M+H]⁺.

EXAMPLE 130

(S)-2-hydroxy-3-methoxy-10-(2-chloroethyl)-5,8,12,12a-tetrahydro-6H-benzo[a]furo[2,3-g]quinolizine (DF009)

The titled product was prepared by the same procedure as that in example 80, except that 5-(2-chloroethyl)furan-3-acetic acid was used to replace 5-ethylthiophene-2-acetic acid.

¹H NMR (CDCl₃, 400 MHz): δ 6.79 (s, 1H), 6.74 (s, 1H), 5.99 (s, 1H), 4.00 (d, J=14.8 Hz, 1H), 3.87 (s, 3H), 3.56 (m, 3H), 3.51 (d, J=14.8 Hz, 1H), 2.85-2.74 (m, 3H), 2.69-2.60 (m, 2H), 2.34 (m, 1H), 1.90 (m, 2H). ESI-MS m/z: 350.1 [M+H]⁺.

EXAMPLE 131

(S)-2-hydroxy-3-methoxy-5,8,12,12a-tetrahydro-6H-benzo[a]pyrrolo[3,2-g]quinolizine (DP001)

The titled product was prepared by the same procedure as that in example 80, except that pyrrole-2-acetic acid was used to replace 5-ethylthiophene-2-acetic acid.

¹H NMR (CDCl₃, 400 MHz): δ 6.79 (s, 1H), 6.75 (s, 1H), 6.50 (d, J=5.1 Hz, 1H), 5.89 (d, J=5.1 Hz, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 271.1 [M+H]⁺.

EXAMPLE 132

(S)-2-hydroxy-3,10-dimethoxy-5,8,12,12a-tetrahydro-6H-benzo[a]pyrrolo[3,2-g]quinolizine (DP002)

The titled product was prepared by the same procedure as that in example 80, except that 5-methoxypyrrole-2-acetic acid was used to replace 5-ethylthiophene-2-acetic acid.

¹H NMR (CDCl₃, 400 MHz): δ 6.79 (s, 1H), 6.75 (s, 1H), 6.10 (s, 1H), 4.05 (d, J=14.8 Hz, 1H), 3.87 (s, 3H), 3.80 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 301.1 [M+H]⁺.

EXAMPLE 133

(S)-2-hydroxy-3,10-dimethoxy-5,8,12,12a-tetrahydro-6H-benzo[a]pyrrolo[2,3-g]quinolizine (DP003)

The titled product was prepared by the same procedure as that in example 80, except that 5-methoxypyrrole-3-acetic acid was used to replace 5-ethylthiophene-2-acetic acid.

¹H NMR (CDCl₃, 400 MHz): δ 6.79 (s, 1H), 6.75 (s, 1H), 6.02 (s, 1H), 4.05 (d, J=14.8 Hz, 1H), 3.87 (s, 3H), 3.80 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 301.1 [M+H]⁺.

EXAMPLE 134

(S)-2-hydroxy-3-methoxy-5,8,13,13a-tetrahydro-6H-benzo[a]pyrido[3,2-g]quinolizine (DP004)

The titled product was prepared by the same procedure as that in example 80, except that pyridine-2-acetic acid was used to replace 5-ethylthiophene-2-acetic acid.

¹H NMR (CDCl₃, 400 MHz): δ 8.33 (d, J=9.1 Hz, 1H), 7.73 (d, J=7.3 Hz, 1H), 7.03 (m, 1H), 6.79 (s, 1H), 6.75 (s, 1H), 6.02 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (in, 2H). ESI-MS m/z: 283.1 [M+H]⁺.

EXAMPLE 135

(S)-2,10-dihydroxy-3,9-dimethoxy-5,8,13,13a-tetrahydro-6H-benzo[a]pyrido[3,2-g]quinolizine (DP005)

The titled product was prepared by the same procedure as that in example 80, except that 4-methoxy-5-hydroxypyridine-2-acetic acid was used to replace 5-ethylthiophene-2-acetic acid.

¹H NMR (CDCl₃, 400 MHz): δ 8.33 (d, J=9.1 Hz, 1H), 6.79 (s, 1H), 6.75 (s, 1H), 4.05 (d, J=14.8 Hz, 1H), 3.87 (s, 3H), 3.84 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 329.1 [M+H]⁺.

EXAMPLE 136

(S)-2-hydroxy-3,10-dimethoxy-5,8,13,13a-tetrahydro-6H-benzo[a]pyrido[2,3-g]quinolizine (DP006)

The titled product was prepared by the same procedure as that in example 80, except that 6-methoxypyridine-3-acetic acid was used to replace 5-ethylthiophene-2-acetic acid.

¹H NMR (CDCl₃, 400 MHz): δ 7.63 (d, J=7.1 Hz, 1H), 6.79 (s, 1H), 6.75 (s, 1H), 6.43 (d, J=7.1 Hz, 1H), 4.05 (d, J=14.8 Hz, 1H), 3.87 (s, 3H), 3.84 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 2H). ESI-MS m/z: 313.1 [M+H]⁺.

EXAMPLE 137

(S)-2-methyl-9-(2-methylpropyl)-4,7,11,11a-tetrahydro-5H-thieno[3,2-a]thieno[3,2-g]quinolizine (SS001)

The titled product was prepared by the same procedure as that in example 78, except that 5-methyl-2-thienal was used to replace 3-methoxy-4-benzyloxybenzaldehyde and 5-(2-methyl propyl)thiophene-2-acetic acid was used to replace thiophene-2-acetic acid.

¹H NMR (CDCl₃, 400 MHz): δ 6.15 (s, 1H), 6.10 (s, 1H), 4.05 (d, J=14.8 Hz, 1H), 3.87 (s, 3H), 3.56 (d, J=10.8 Hz, 1H), 3.48 (d, J=14.9 Hz, 1H), 3.25-3.08 (m, 3H), 2.90-2.81 (m, 1H), 2.69-2.60 (m, 4H), 2.36 (s, 3H), 1.82 (m, 1H), 0.91-0.89 (m, 6H). ESI-MS m/z: 318.1 [M+H]⁺.

EXAMPLE 138

(S)-2-methyl-9-(2-chloroethyl)-4,7,11,11a-tetrahydro-5H-thieno[3,2-a]thieno[3,2-g]quinolizine (SS002)

The titled product was prepared by the same procedure as that in example 78, except that 5-(2-chloroethyl)thiophene-2-acetic acid was used to replace thiophene-2-acetic acid.

¹H NMR (CDCl₃, 400 MHz): δ 6.15 (s, 1H), 6.10 (s, 1H), 4.05 (d, J=14.8 Hz, 1H), 3.87 (s, 3H), 3.60-3.55 (m, 3H), 3.48 (d, J=14.9 Hz, 1H), 3.25-3.08 (m, 3H), 2.90-2.81 (m, 1H), 2.69-2.60 (m, 4H), 2.36 (s, 3H). ESI-MS m/z: 324.0 [M+H]⁺.

EXAMPLE 139

(S)-2-methyl-9-(2-chloroethyl)-4,7,11,11a-tetrahydro-5H-thieno[3,2-a]furo[3,2-g]quinolizine (SF001)

The titled product was prepared by the same procedure as that in example 78, except that 5-(2-chloroethyl)furan-2-acetic acid was used to replace thiophene-2-acetic acid.

¹H NMR (CDCl₃, 400 MHz): δ 6.16 (s, 1H), 6.11 (s, 1H), 4.00 (d, J=14.8 Hz, 1H), 3.84 (s, 3H), 3.63-3.56 (m, 3H), 3.48 (d, J=14.9 Hz, 1H), 3.25-3.08 (m, 3H), 2.90-2.81 (m, 1H), 2.69-2.60 (m, 4H), 2.36 (s, 3H). ESI-MS m/z: 308.0 [M+H]⁺.

EXAMPLE 140

(S)-2-methyl-9-(2-chloroethyl)-4,7,11,11a-tetrahydro-5H-furo[3,2-a]thieno[3,2-g]quinolizine (FS001)

The titled product was prepared by the same procedure as that in example 78, except that 5-methyl-2-furfural was used to replace 3-methoxy-4-benzyloxybenzaldehyde and 5-(2-chloroethyl)thiophene-2-acetic acid was used to replace thiophene-2-acetic acid.

¹H NMR (CDCl₃, 400 MHz): δ 6.15 (s, 1H), 6.09 (s, 1H), 4.04 (d, J=14.8 Hz, 1H), 3.84 (s, 3H), 3.60-3.56 (m, 3H), 3.48 (d, J=14.9 Hz, 1H), 3.25-3.08 (m, 3H), 2.90-2.81 (m, 1H), 2.69-2.60 (m, 4H), 2.37 (s, 3H). ESI-MS m/z: 308.0 [M+H]⁺.

EXAMPLE 141

(S)-11-(2-methylpropyl)-6,9,13,13a-tetrahydro-5H-indolo[2,3-a]thieno[3,2-g]quinolizine (IS001)

The titled product was prepared by the same procedure as that in example 78, except that tryptamine was used to replace 3-methoxy-4-benzyloxyphenylethylamine and 5-(2-methylpropyl)thiophene-2-acetic acid was used to replace thiophene-2-acetic acid.

¹H NMR (CDCl₃, 400 MHz): δ 7.20-7.13 (m, 4H), 6.56 (s, 1H), 4.04 (d, J=14.8 Hz, 1H), 3.64 (d, J=10.8 Hz, 1H), 3.47 (d, J=14.8 Hz, 1H), 3.25-3.08 (m, 4H), 2.69-2.60 (m, 2H), 1.82-1.77 (m, 1H), 0.96 (s, 6H). ESI-MS m/z: 337.4 [M+H]⁺.

EXAMPLE 142

(S)-11-(2-chloroethyl)-6,9,13,13a-tetrahydro-5H-indolo[2,3-a]thieno[3,2-g]quinolizine (IS002)

The titled product was prepared by the same procedure as that in example 78, except that tryptamine was used to replace 3-methoxy-4-benzyloxyphenylethylamine and 5-(2-chloroethyl)thiophene-2-acetic acid was used to replace thiophene-2-acetic acid.

$^1$H NMR (CDCl$_3$, 400 MHz): δ 7.20-7.13 (m, 411), 6.56 (s, 1H), 4.08 (d, J=14.8 Hz, 1H), 3.70-3.64 (m, 3H), 3.47 (d, J=14.8 Hz, 1H), 3.25-3.08 (m, 4H), 2.69-2.60 (m, 4H), 1.82-1.77 (m, 1H). ESI-MS m/z: 343.7 [M+H]$^+$.

EXAMPLE 143

(S)-3-methoxy-11-(2-methylpropyl)-6,9,13,13a-tetrahydro-5H-indolo[2,3-a]thieno[3,2-g]quinolizine (IS003)

The titled product was prepared by the same procedure as that in example 78, except that 6-methoxytryptamine was used to replace 3-methoxy-4-benzyloxyphenylethylamine and 5-(2-methylpropyl)thiophene-2-acetic acid was used to replace thiophene-2-acetic acid.

$^1$H NMR (CDCl$_3$, 400 MHz): δ 7.08-7.03 (m, 311), 6.56 (s, 1H), 4.04 (d, J=14.8 Hz, 1H), 3.64 (d, J=10.8 Hz, 1H), 3.47 (d, J=14.8 Hz, 1H), 3.25-3.08 (m, 411), 2.69-2.60 (m, 2H), 1.82-1.77 (m, 1H), 0.96 (s, 611). ESI-MS m/z: 367.4 [M+H]$^+$.

EXAMPLE 144

(S)-3-methoxy-11-(2-chloroethyl)-6,9,13,13a-tetrahydro-5H-indolo[2,3-a]thieno[3,2-g]quinolizine (IS004)

The titled product was prepared by the same procedure as that in example 78, except that 6-methoxytryptamine was used to replace 3-methoxy-4-benzyloxy phenylethylamine and 5-(2-chloroethyl)thiophene-2-acetic acid was used to replace thiophene-2-acetic acid.

$^1$H NMR (CDCl$_3$, 400 MHz): δ 7.08 (d, J=8.0 Hz, 1H), 6.98 (d, J=8.0 Hz, 1H), 6.56 (s, 1H), 6.21 (s, 1H), 4.04 (d, J=14.8 Hz, 1H), 3.86 (s, 1H), 3.64 (d, J=10.8 Hz, 1H), 3.70-3.64 (m, 3H), 3.25-3.08 (m, 411), 2.69-2.60 (m, 4H), 1.82-1.77 (m, 1H). ESI-MS m/z: 373.8 [M+H]$^+$.

EXAMPLE 145

(S)-2-hydroxy-3-methoxy-10-(2'-hydroxyethoxymethyl)-5,8,12,12a-tetra hydro-6H-benzo[a]thieno[3,2-g]quinolizine (DS045)

The titled product was prepared by the same procedure as that in example 80, except that ethyl 5-(2'-hydroxyethoxymethyl)thiophene-2-acetate was used to replace ethyl 5-ethylthiophene-2-acetate.

$^1$H NMR (CDCl$_3$, 400 MHz): δ 6.79 (s, 1H), 6.75 (s, 1H), 6.59 (s, 1H), 4.49 (d, J=13.6 Hz, 1H), 4.05 (d, J=14.8 Hz, 1H), 3.80 (s, 3H), 3.67-3.55 (m, 6H), 3.25-3.08 (m, 3H), 2.90-2.81 (m, 1H), 2.69-2.60 (m, 2H). ESI-MS m/z: 373.1 [M+H]$^+$.

EXAMPLE 146

(S)-2-hydroxy-3-methoxy-10-(dimethylaminomethyl)-5,8,12,12a-tetrahydro-6H-benzo[a]thieno[3,2-g]quinolizine (DS046)

The titled product was prepared by the same procedure as that in example 80, except that ethyl 5-(dimethylaminomethyl)thiophene-2-acetate was used to replace ethyl 5-ethylthiophene-2-acetate.

$^1$H NMR (CDCl$_3$, 400 MHz): δ 6.79 (s, 1H), 6.75 (s, 1H), 6.59 (s, 1H), 4.05 (d, J=14.8 Hz, 1H), 3.80 (s, 3H), 3.67-3.55 (m, 4H), 3.25-3.08 (m, 3H), 2.90-2.81 (m, 1H), 2.69-2.60 (m, 2H), 2.10 (s, 6H). ESI-MS m/z: 345.1 [M+H]$^+$.

EXAMPLE 147

(S)-2-hydroxy-3-methoxy-10-(morpholine-N-methyl)-5,8,12,12a-tetrahydro-6H-benzo[a]thieno[3,2-g]quinolizine (DS047)

The titled product was prepared by the same procedure as that in example 80, except that ethyl 5-(morpholine-N-methyl)thiophene-2-acetate was used to replace ethyl 5-ethylthiophene-2-acetate.

$^1$H NMR (CDCl$_3$, 400 MHz): δ 6.79 (s, 1H), 6.75 (s, 1H), 6.59 (s, 1H), 4.05 (d, J=14.8 Hz, 1H), 3.80 (s, 3H), 3.67-3.50 (m, 8H), 3.25-3.08 (m, 3H), 2.90-2.81 (m, 1H), 2.69-2.60 (m, 2H), 2.55-2.50 (t, J=12 Hz, 4H). ESI-MS m/z: 387.1 [M+H]$^+$.

EXAMPLE 148

(S)-2-hydroxy-3-methoxy-10-((N-methyl)-piperazine-N-methyl)-5,8,12,12a-tetrahydro-6H-benzo[a]thieno[3,2-g]quinolizine (DS048)

The titled product was prepared by the same procedure as that in example 80, except that ethyl 5-((N-methyl)piperazine-N-methyl)thiophene-2-acetate was used to replace ethyl 5-ethylthiophene-2-acetate.

$^1$H NMR (CDCl$_3$, 400 MHz): δ 6.79 (s, 1H), 6.75 (s, 1H), 6.59 (s, 1H), 4.05 (d, J=14.8 Hz, 1H), 3.80 (s, 3H), 3.67-3.50 (m, 4H), 3.25-3.08 (m, 3H), 2.90-2.81 (m, 1H), 2.69-2.60 (m, 2H), 2.55-2.50 (t, J=12 Hz, 4H), 2.42-2.38 (t, J=12 Hz, 4H), 2.17 (s, 3H). ESI-MS m/z: 400.2 [M+H]$^+$.

EXAMPLE 149

(S)-4,7,12,12a-tetrahydro-5H-thieno[3,2-a]benzooxazole[6,5-g]quinolizin e (SBE01)

The titled product was prepared by the same procedure as that in example 31, except that benzooxazole-5-acetic acid was used to replace 2,5-dimethoxyphenylacetic acid.

$^1$H NMR (CDCl$_3$, 400 MHz): δ 7.62 (s, 1H), 6.79 (d, J=7.8 Hz, 1H), 6.75 (s, 1H), 6.70 (d, J=7.8 Hz, 1H), 6.59 (s,

1H), 4.05 (d, J=14.8 Hz, 1H), 3.67-3.50 (m, 2H), 3.25-3.08 (m, 3H), 2.90-2.81 (m, 1H), 2.69-2.60 (m, 2H). ESI-MS m/z: 283.0 [M+H]$^+$.

EXAMPLE 150

(S)-10-(2-methylpropyl)-5,8,12,12a-tetrahydro-6H-benzofuro[6,5-a]thieno[3,2-g]quinolizine (FBS01)

The titled product was prepared by the same procedure as that in example 80, except that 2-methylpropionyl chloride was used to replace acetyl chloride and benzofuran-5-acetic acid was used to replace 3-methoxy-4-benzyloxyphenylethylamine.
$^1$H NMR (CDCl$_3$, 400 MHz): δ 7.42 (d, J=7.8 Hz, 1H), 7.30 (s, 1H), 7.12 (s, 1H), 6.75 (s, J=7.8 Hz, 1H), 6.14 (s, 1H), 4.10 (d, J=14.8 Hz, 1H), 3.56 (m, 2H), 3.25-3.08 (m, 3H), 2.78-2.70 (m, 2H), 2.60 (d, J=12.8 Hz, 2H), 1.82 (m, 1H), 0.91-0.89 (m, 6H). ESI-MS m/z: 338.0 [M+H]$^+$.

EXAMPLE 151

(S)-2-methyl-8-methoxy-9-((2-morpholino)ethoxy)-4,7,12,12a-tetrahydro-5H-benzo[g]thieno[3,2-a]quinolizine (AS053)

The titled product was prepared by the same procedure as that in example 3, except that 7-(morpholine-N-ethoxy)-8-methoxy-3-isochromanone was used to replace 7-benzyloxy-8-methoxy-3-isochromanone.
$^1$H NMR (CDCl$_3$, 400 MHz): δ 6.78 (d, J=8.1, 1H), 6.70 (d, J=8.1, 1H), 6.22 (s, 1H), 4.11 (t, J=13.0 Hz, 1H), 3.95 (d, J=14.8 Hz, 1H), 3.83 (s, 3H), 3.68-3.64 (m, 6H), 3.29-3.24 (m, 2H), 3.16-3.08 (m, 4H), 2.85-2.70 (m, 2H), 2.51 (t, J=13.0 Hz, 4H), 2.23 (s, 3H). ESI-MS m/z: 415.0 [M+H]$^+$.

EXAMPLE 152

(S)-2-hydroxy-3-methoxy-10-(acetyldimethylamino)-5,8,12,12a-tetrahydro-6H-benzo[a]thieno[3,2-g]quinolizine (DS049)

The titled product was prepared by the same procedure as that in example 80, except that ethyl 5-(acetyldimethylamino)thiophene-2-acetate was used to replace ethyl 5-ethylthiophene-2-acetate.
$^1$H NMR (CDCl$_3$, 400 MHz): δ 6.79 (s, 1H), 6.75 (s, 1H), 6.59 (s, 1H), 4.05 (d, J=14.8 Hz, 1H), 3.80 (s, 3H), 3.67-3.50 (m, 2H), 3.49 (s, 6H), 3.42 (s, 2H), 3.25-3.08 (m, 3H), 2.90-2.81 (m, 1H), 2.69-2.60 (m, 2H). ESI-MS m/z: 373.1 [M+H]$^+$.

EXAMPLE 153

(S)-2-hydroxy-3-methoxy-5,8,12,12a-tetrahydro-6H-benzo[a]thieno[3,2-g]quinolizine-10-acetic acid (DS050)

The titled product was prepared by the same procedure as that in example 80, except that 5-(carboxyethyl)thiophene-2-acetic acid was used to replace ethyl 5-ethylthiophene-2-acetate.
$^1$H NMR (CDCl$_3$, 400 MHz): δ 10.80 (b, 1H), 6.79 (s, 1H), 6.75 (s, 1H), 6.23 (s, 1H), 4.05 (d, J=14.8 Hz, 1H), 3.80 (s, 3H), 3.67-3.50 (m, 2H), 3.42 (s, 2H), 3.25-3.08 (m, 3H), 2.90-2.81 (m, 1H), 2.69-2.60 (m, 2H). ESI-MS m/z: 346.0 [M+H]$^+$.

EXAMPLE 154

(S)-2-hydroxy-3-methoxy-10-(ethylol)-5,8,12,12a-tetrahydro-6H-benzo[a]thieno[3,2-g]quinolizine-10-acetic acid (DS051)

The titled product was prepared by the same procedure as that in example 80, except that ethyl 5-(ethylol)thiophene-2-acetate was used to replace ethyl 5-ethylthiophene-2-acetate.
$^1$H NMR (CDCl$_3$, 400 MHz): δ 6.79 (s, 1H), 6.75 (s, 1H), 6.18 (s, 1H), 4.05 (d, J=14.8 Hz, 1H), 3.80 (s, 3H), 3.67-3.50 (m, 4H), 3.42 (s, 2H), 3.25-3.08 (m, 3H), 2.90-2.81 (m, 1H), 2.74-2.81 (t, J=12.8 Hz, 2H), 2.69-2.60 (m, 2H). ESI-MS m/z: 332.0 [M+H]$^+$.

EXAMPLE 155

Methyl(S)-2-hydroxy-3-methoxy-5,8,12,12a-tetrahydro-6H-benzo[a]thieno[3,2-g]quinolizine-10-acetate (DS052)

The titled product was prepared by the same procedure as that in example 80, except that 5-(methoxycarbonylethyl)thiophene-2-acetic acid was used to replace ethyl 5-ethylthiophene-2-acetate.
$^1$H NMR (CDCl$_3$, 400 MHz): δ 6.79 (s, 1H), 6.75 (s, 1H), 6.23 (s, 1H), 4.05 (d, J=14.8 Hz, 1H), 3.87 (s, 3H), 3.69 (s, 3H), 3.60-3.52 (m, 2H), 3.42 (s, 2H), 3.25-3.08 (m, 3H), 2.90-2.81 (m, 1H), 2.69-2.60 (m, 2H). ESI-MS m/z: 359.0 [M+H]$^+$.

Pharmacological Experiments

1. In the present invention, pharmacological experiments were conducted with respect to the affinity of diarylo[a,g] quinolizines of formulae (I) on dopamine D1, dopamine D2, 5-HT$_{1A}$ and 5-HT$_{2A}$ receptors. The experimental materials required for the pharmacological experiments were commercially purchased, unless otherwise specified.

(1) Determination of the affinity of the diarylo[a,g]quinolizines of formula (I) and derivatives thereof on dopamine D1, dopamine D2, 5-HT$_{1A}$ and 5-HT$_{2A}$ receptors.

1) The Experimental Method

The compound of the invention at different concentrations ($10^{-5}$ M-$10^{-11}$ M), an isotope receptor ligand and a receptor protein were loaded into a reaction tube, incubated at 30° C. in a water bath for 60 min, and then terminated in a refrigerator. The mixture was filtered through suction filtration using GF/C glass fiber paper on a Millipore filter (millipore) cell sample collector, and dried. The resulting sample was placed into a 0.5 mL tube, added with 500 μL of liquid scintillation fluid, and counted for measuring the intensity of radioactivity.

2) The Expertmental Materials (1) materials for receptor construction and cell culture: *Escherichia coli*. DH5αstrain; insect virus transfer vector pVL1393 plasmid; BaculoGold linear Chinese baculovirus DNA, purchased from ParMingen company; mkD1RcDNA; rD2R cDNA; various restriction endonucleases, TaqDNA polymerase, T4 ligase, etc., LB medium; insect cell culture TNM-FH.

(2) The Experimental Materials for Binding Receptor

For dopamine D1 receptor: isotope receptor ligand [$^3$H]-SCH23390 (85.0 Ci/mmol) (D1-selective, purchased from Amersham Corporation), D1 receptor protein expressed in HEK-293 cells;

For dopamine D2 dopamine receptor: isotope receptor ligand [³H]Spiperone (77.0 Ci/mmol) (D2-selective, purchased from Amersham Corporation), D2 receptor protein expressed in HEK-293 cells;

For 5-$HT_{1A}$ receptor: isotope receptor ligand [3H]8-OH-DPAT; 5-$HT_{1A}$ receptor protein expressed in HEK-293 cells;

For 5-$HT_{2A}$ receptor: isotope receptor ligand [3H]-Ketanserin; 5-$HT_{2A}$ receptor protein expressed in HEK-293 cells;

Firstly, the above receptor proteins were dissolved in DMSO and then diluted with double distilled water to the appropriate concentration ($10^{-5}$ M-$10^{-11}$ M).

(+) Butaclamo was purchased from RBI Company, GF/C glass fiber filter paper was purchased from Whatman Co., liquid scintillation fluid (dopamine D1, D2 receptors)/liposoluble scintillation fluid (5-$HT_{1A}$, 5-$HT_{2A}$ receptor), Beckman LS-6500 multi-function liquid scintillation counter.

3. The Test Results are Shown in Tables 1 and 2.

Table 1 results of the affinity of some representative compounds on dopamine D1 and D2 receptors It can be seen from the above that the tested compounds have very strong affinity on dopamine D1 and D2 receptors. Further, some compounds of the present invention exhibit a strong affinity on 5-$HT_{1A}$.

INDUSTRIAL APPLICATION

The diarylo[a,g]quinlizines of the invention have relatively low toxicity and good solubility.

The preparation method for the diarylo[a,g]quinlizines and derivatives of the invention has advantages of, for example, mild reaction condition, abundant and readily available raw materials, simple operation and post-treatment, good selectivity, etc.

The diarylo[a,g]quinlizines and derivatives thereof according to the invention have excellent selectivity among different subtypes of serotonin receptors and dopamine receptors.

Therefore, the compounds of the invention can be used in preparing a medicament for treating a disease relating to nervous system, especially to the dopamine receptors D1 and D2 as well as serotonin receptors 5-$HT_{1A}$ and 5-$HT_{2A}$.

|  | D1 receptor | | | D2 receptor | | |
|---|---|---|---|---|---|---|
| Compound | inhibition % | Ki (nM) | IC$_{50}$ (nM) | inhibition % | Ki (nM) | IC$_{50}$ (nM) |
| AS003 | 99.80 | 37.94 ± 2.21 | 73.99 ± 4.30 | 40.31 | ND | ND |
| AS004 | 86.32 | 114.84 ± 22.38 | 229.68 ± 44.76 | 6.97 | ND | ND |
| AS005 | 98.23 | 47.57 ± 6.18 | 86.81 ± 11.28 | 62.98 | ND | ND |
| AS022 | 69.25 | ND | ND | 5.21 | ND | ND |
| AS023 | 89.62 | 357.20 ± 7.83 | 714.40 ± 15.66 | 22.17 | ND | ND |
| AS032 | 96.00 | 158.94 ± 28.91 | 416.4 ± 26.87 | 13.75 | ND | ND |
| AS050 | 99.02 | 685.43 ± 72.20 | 1520.9 ± 356.52 | 22.63 | ND | ND |
| AS051 | 76.38 | ND | ND | 1.29 | ND | ND |
| DS001 | — | 86.98 ± 4.30 | 171.80 ± 8.49 | — | 88.02 ± 15.16 | 396.08 ± 68.22 |
| DS003 | 98.16 | 26.33 ± 0.37 | 48.06 ± 0.68 | 98.50 | 40.83 ± 3.80 | 180.33 ± 16.78 |
| DS005 | 96.74 | 61.75 ± 6.88 | 112.69 ± 12.57 | 96.31 | 38.63 ± 2.15 | 170.60 ± 9.50 |
| DS006 | 94.29 | 128.14 ± 9.53 | 233.85 ± 17.39 | 99.50 | 7.54 ± 0.23 | 32.66 ± 0.98 |
| DS007 | 97.62 | 62.19 ± 7.13 | 113.49 ± 13.00 | 99.53 | 17.61 ± 1.95 | 76.32 ± 8.46 |
| DS013 | 98.64 | 16.43 ± 2.81 | 112.69 ± 12.57 | 98.37 | 34.36 ± 2.72 | 145.64 ± 7.19 |
| DS015 | 96.10 | 77.00 ± 2.85 | 144.38 ± 5.35 | 97.19 | 18.38 ± 2.30 | 55.15 ± 6.89 |
| DS016 | 95.84 | 158.42 ± 10.70 | 297.04 ± 20.06 | 93.54 | 49.94 ± 7.8 | 149.81 ± 23.39 |
| DS008 | 88.78 | ND | ND | 90.45 | 79.54 ± 4.83 | 238.62 ± 14.67 |

—: no test data for the test.
ND: Not Dectected.

Table 2 results of the affinity of some representative compounds on 5-$HT_{1A}$ and 5-$HT_{2A}$ receptors

|  | 5-$HT_{1A}$ receptor | | | 5-$HT_{2A}$ receptor | | |
|---|---|---|---|---|---|---|
| Compound | inhibition % | Ki (nM) | IC$_{50}$ (nM) | inhibition % | Ki (nM) | IC$_{50}$ (nM) |
| AS003 | 91.91 | 405.01 ± 87.1 | 514.1 ± 110.6 | 90.43 | 1074.70 ± 22.4 | 2230.5 ± 46.5 |
| AS004 | 51.69 | ND | ND | 44.24 | ND | ND |
| AS005 | 98.58 | 129.82 ± 3.03 | 162.40 ± 3.80 | 76.11 | ND | ND |
| AS022 | 6.60 | ND | ND | 32.31 | ND | ND |
| AS023 | 76.45 | ND | ND | 60.08 | ND | ND |
| AS032 | 74.09 | ND | ND | 30.01 | ND | ND |
| AS050 | 49.26 | ND | ND | 74.25 | ND | ND |
| AS051 | 33.90 | ND | ND | 46.59 | ND | ND |
| AI001 | 88.22 | 728.23 ± 104.19 | 911.02 ± 130.36 | 50.46 | ND | ND |
| DS003 | 92.10 | 997.76 ± 189.57 | 1248.15 ± 237.09 | 45.15 | ND | ND |
| DS005 | 85.33 | 1966.00 ± 228.96 | 2459.45 ± 286.45 | 29.55 | ND | ND |
| DS006 | 83.71 | ND | ND | 50.31 | ND | ND |
| DS007 | 87.03 | 863.79 ± 77.32 | 1080.60 ± 96.73 | 53.34 | ND | ND |
| DS013 | 89.84 | 553.09 ± 81.59 | 691.92 ± 102.07 | 34.81 | ND | ND |
| DS015 | 92.24 | 118.7 ± 23.02 | 147.68 ± 28.64 | ND | ND | ND |

ND: Not detected

The invention claimed is:

1. A diarylo[a,g]quinolizine compound of formula (I), an enantiomer, a diastereoisomer, a racemate, a mixture, a pharmaceutically acceptable salt, a crystalline hydrate or a solvate thereof:

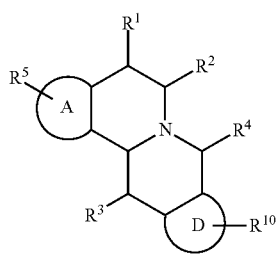

(I)

wherein ring A is one selected from the group consisting of benzene ring, pyrrole ring, furan ring, thiophene ring, pyridine ring, benzoxazole ring, benzofuran ring and indole ring;

ring D is one selected from the group consisting of benzene ring, pyrrole ring, furan ring, thiophene ring, pyridine ring, benzoxazole ring and benzofuran ring; the rings A and D are not simultaneously benzene ring, and ring A is not an indole ring when ring D is a benzene ring;

$R^5$ and $R^{10}$ each independently represent 1 to 4 substituents selected from the group consisting of halogen, C1-C6 straight or branched alkyl unsubstituted or substituted with 1-3 halogens, C3-C6 cycloalkyl unsubstituted or substituted with 1-3 halogens, C1-C6 straight or branched alkyl substituted with a C1-C6 alkoxy, C1-C6 straight or branched alkyl substituted with a C3-C6 cycloalkyl, —$OR^6$, —$NR^6R^7$, —$OR^9OR^6$, —$OR^9NR^6R^7$, —$R^9COOR^6$, —$R^9CONR^6R^7$, —$R^9OR^6$, —$R^9NR^6R^7$, and —$N(R^6)SO_2R^7$, alternatively, any two adjacent $R^5$s or adjacent $R^{10}$s, together with the carbon atom or the heteroatom to which they are adjacent, may form a 5-7 membered heterocycle containing 1 to 3 heteroatoms selected from the group consisting of N, O and S;

$R^1$, $R^2$ and $R^3$ are each independently hydrogen, halogen, hydroxy, oxo (=O), or C1-C6 straight or branched alkyl unsubstituted or substituted with 1-3 halogens, $R^4$ is hydrogen, halogen, hydroxy, or C1-C6 straight or branched alkyl unsubstituted or substituted with 1-3 halogens, $R^6$ and $R^7$ are each independently hydrogen, or C1-C6 straight or branched alkyl unsubstituted or substituted with 1-3 halogens or hydroxys, $R^9$ is C1-C6 straight or branched alkylene;

the halogen is F, Cl or Br; and the chiral carbon atom in the compound of formula (I) may be on R- or S- configuration.

2. A diarylo[a,g]quinolizine compound, enantiomer, diastereoisomer, racemate, mixture, pharmaceutically acceptable salt, crystalline hydrate or solvate thereof, wherein the diarylo[a,g]quinolizine compound is

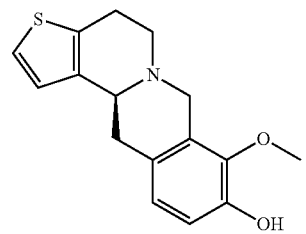

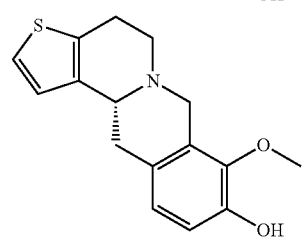

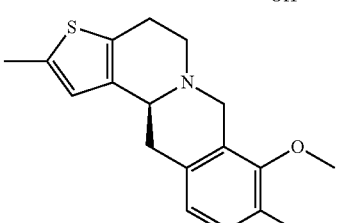

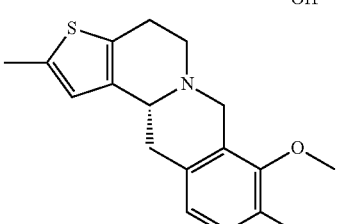

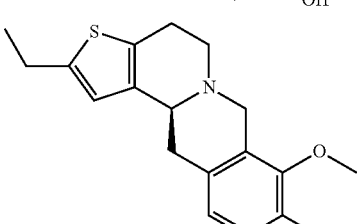

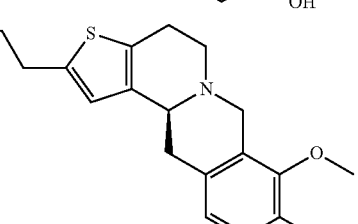

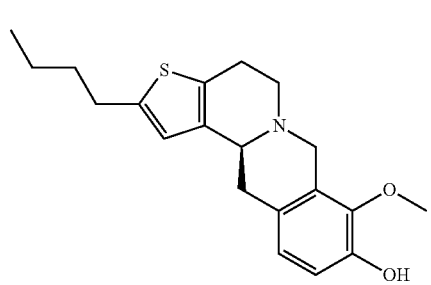

127
-continued
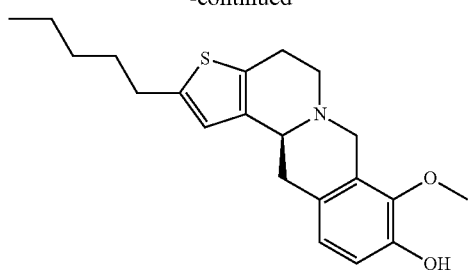
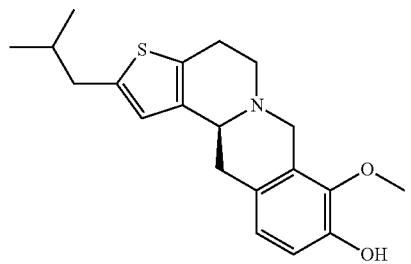
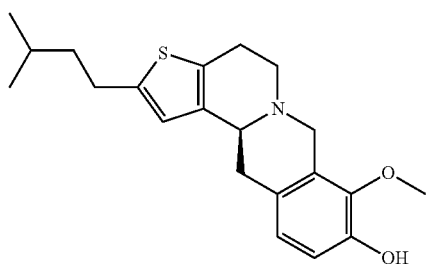
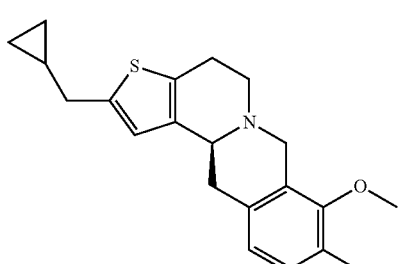
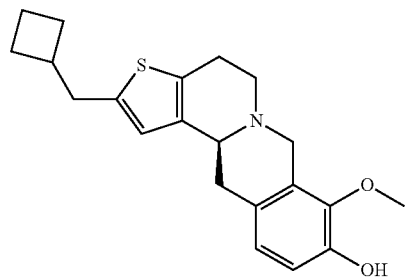
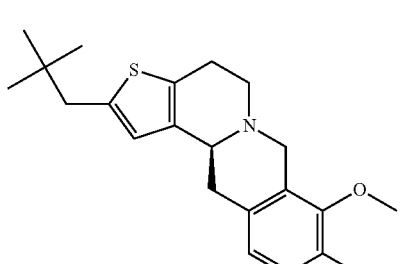
128
-continued
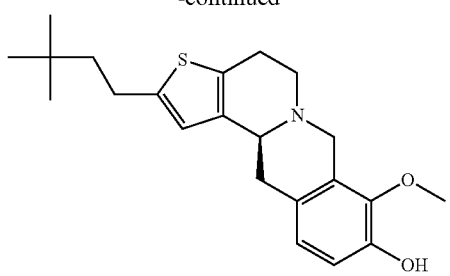
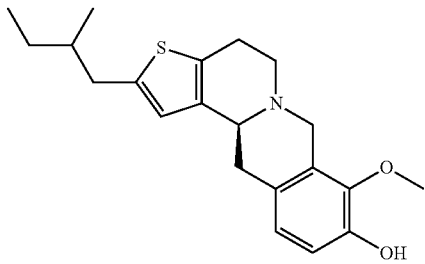
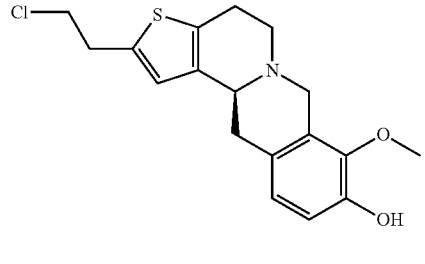
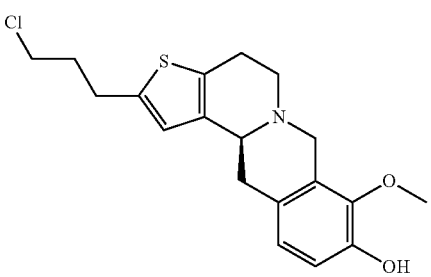
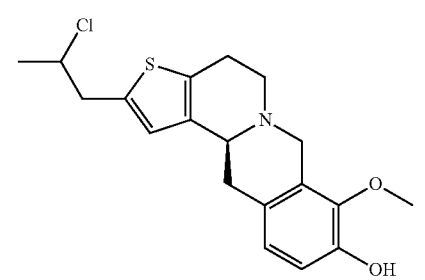
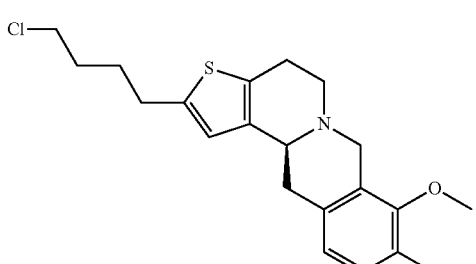

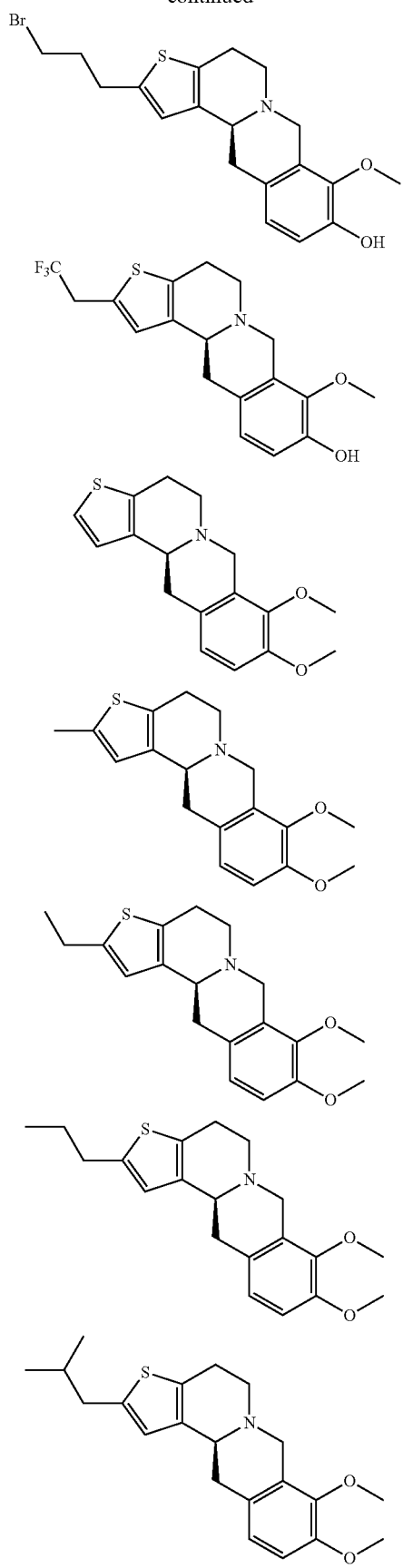
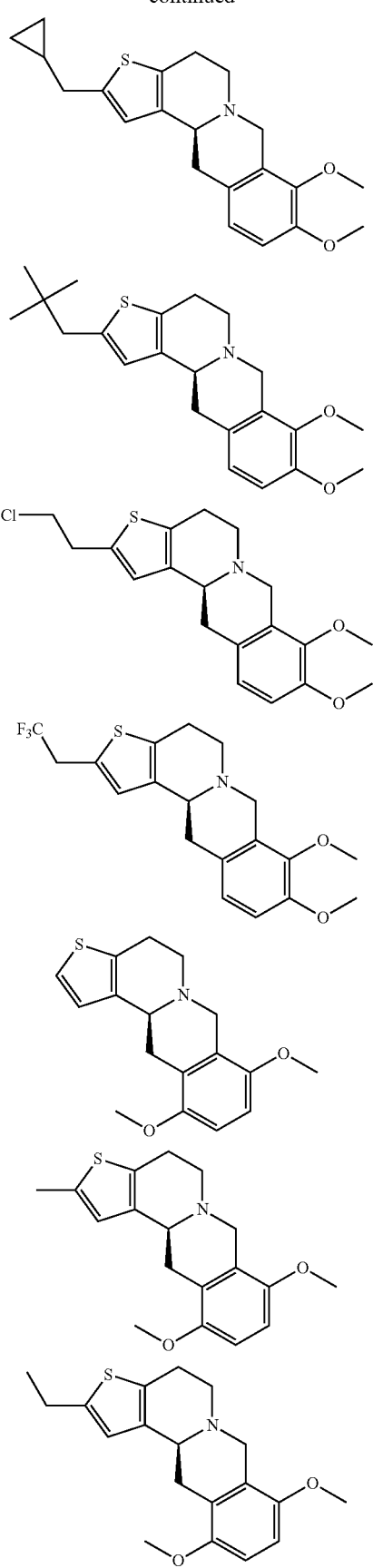

131
-continued
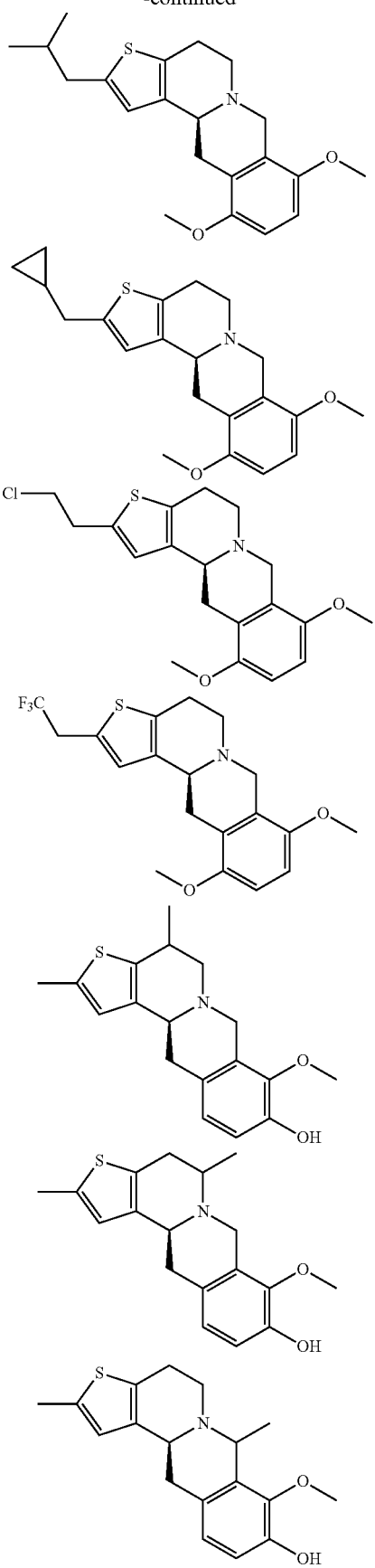
132
-continued
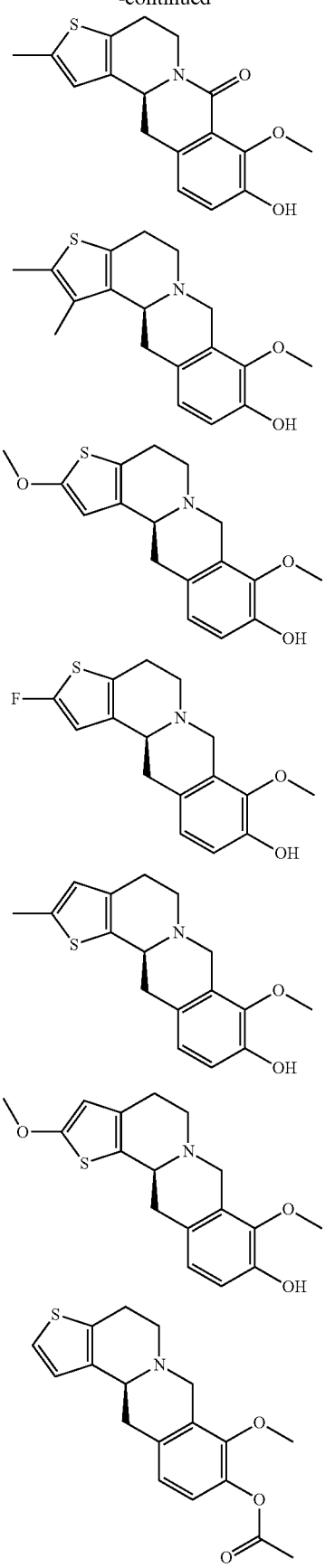

133
-continued
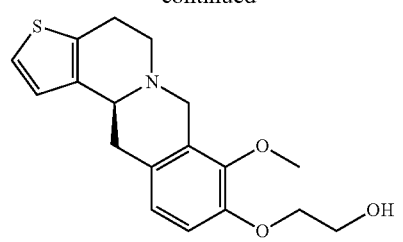
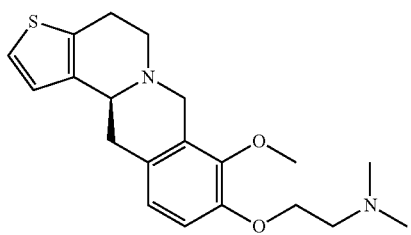
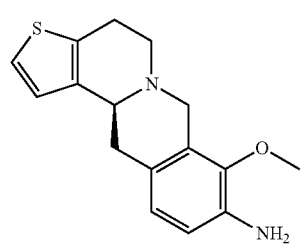
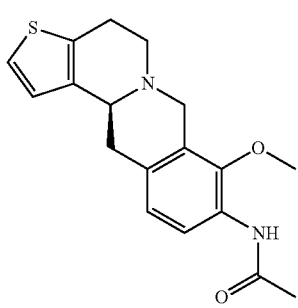
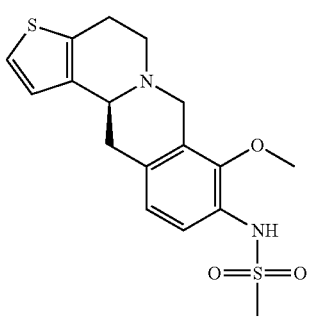
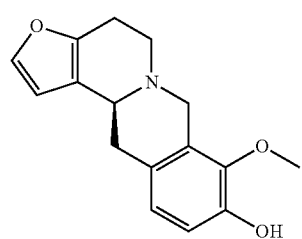
134
-continued
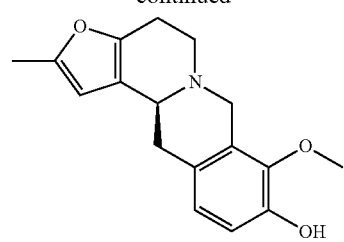
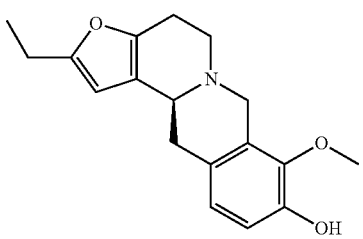
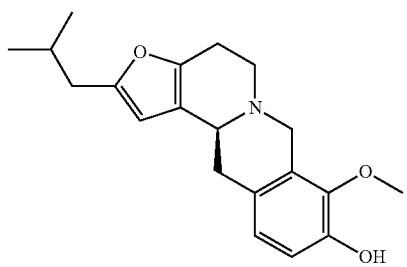
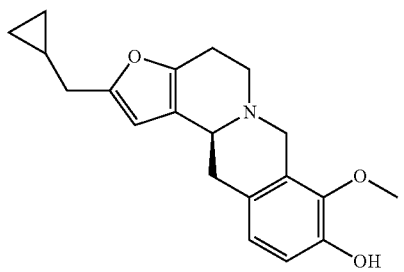
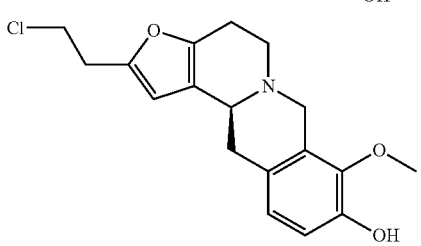
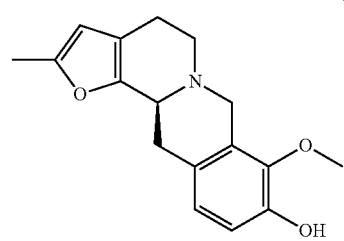
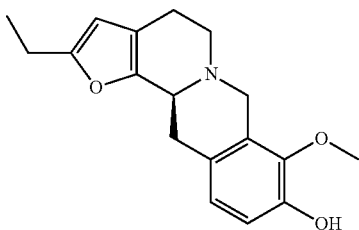

135
-continued
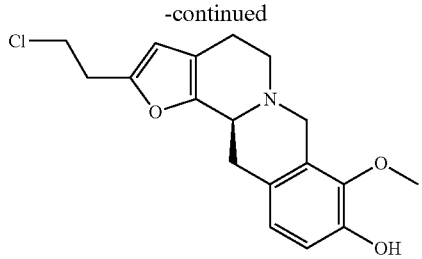
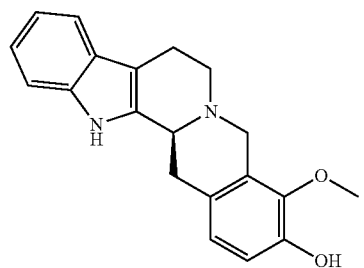
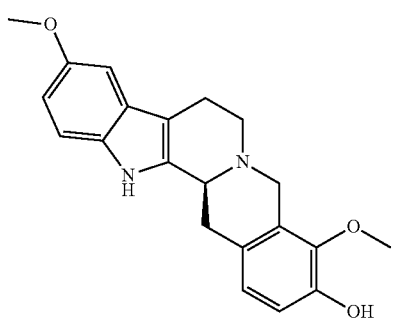
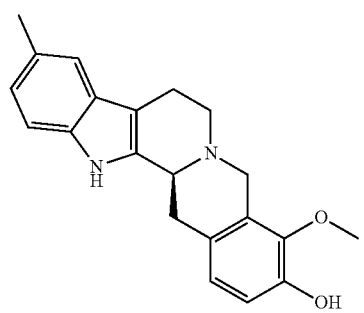
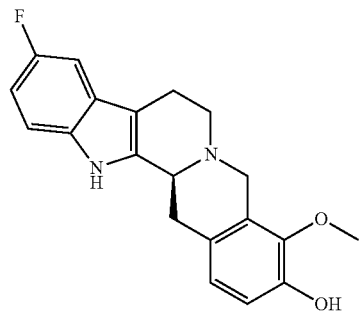
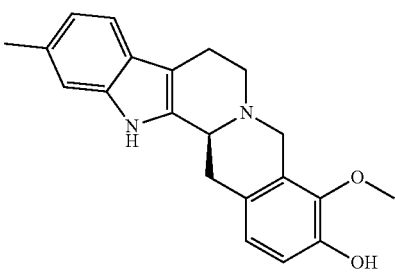
136
-continued
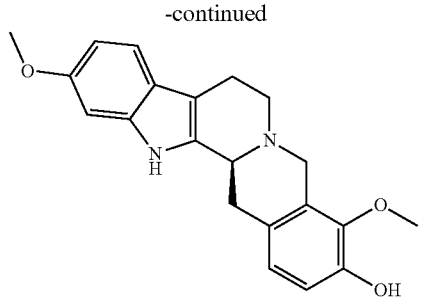
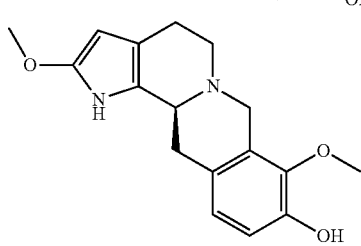
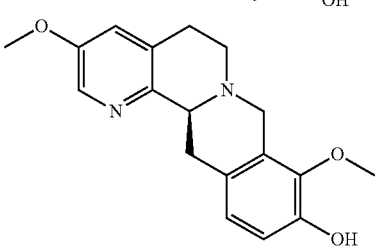
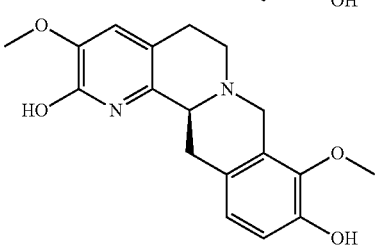
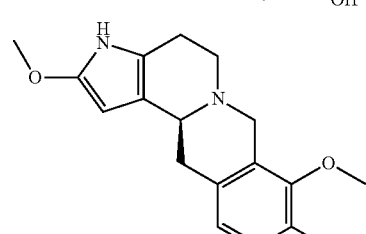
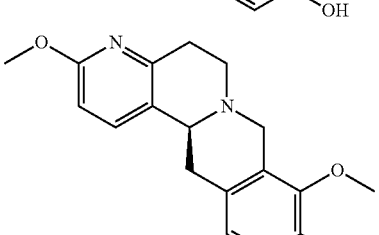
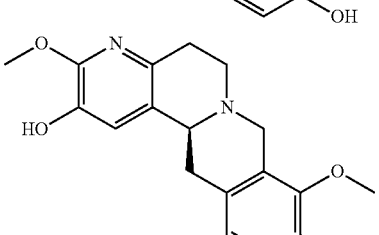

137
-continued
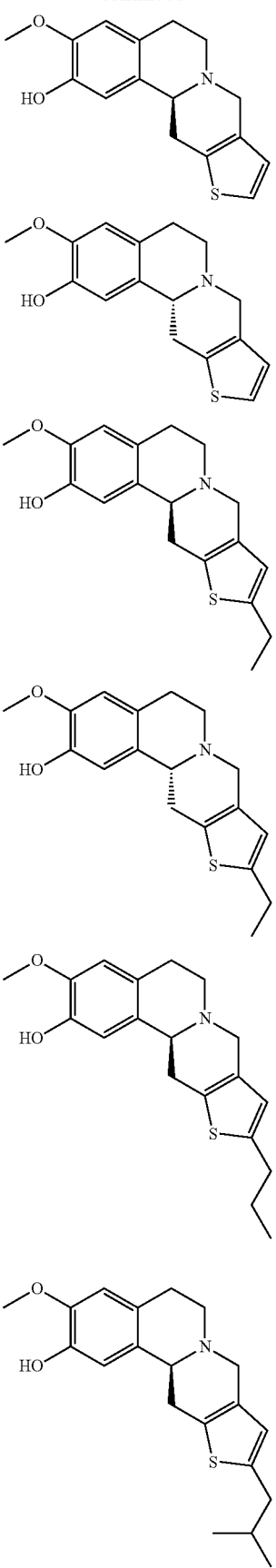
138
-continued
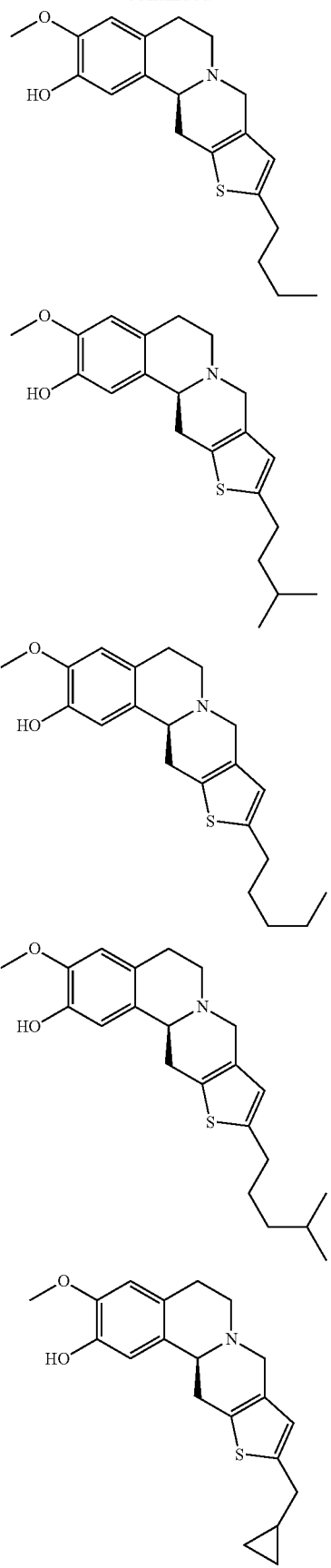

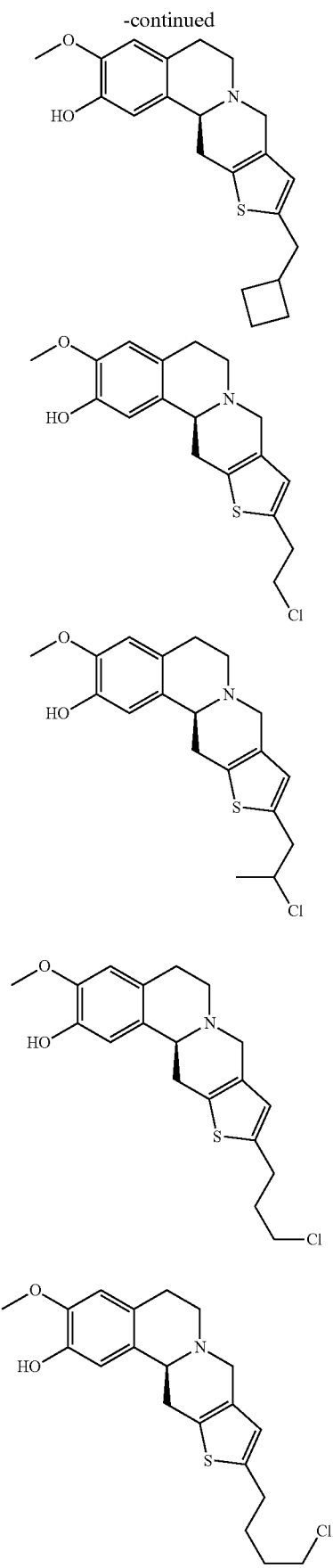

141
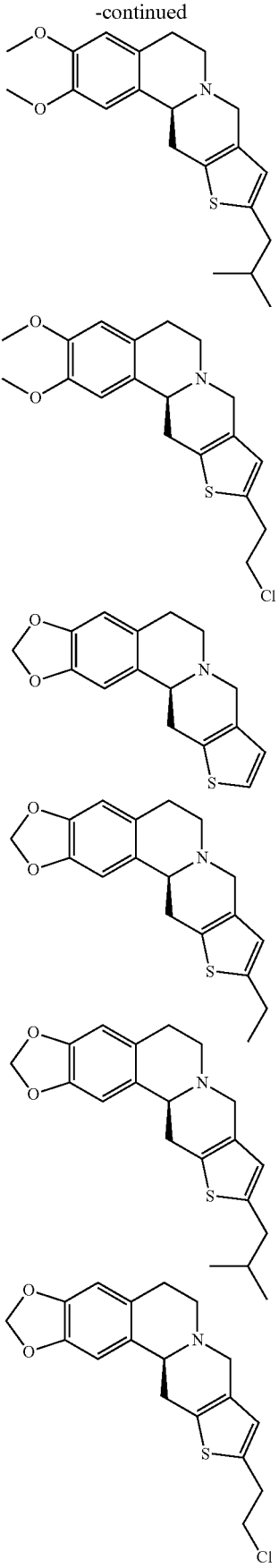
142
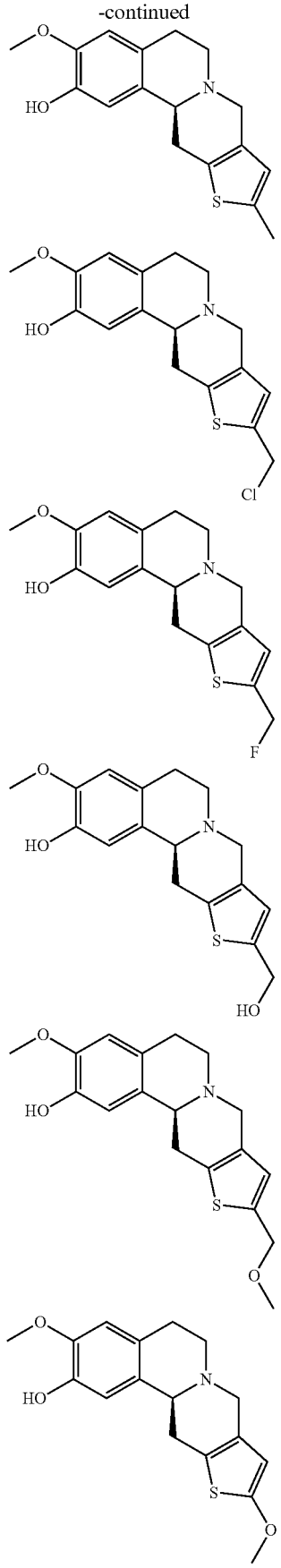

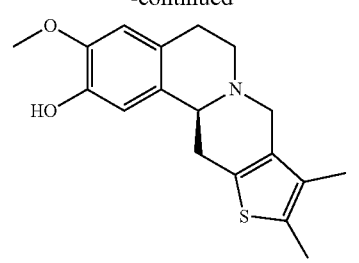
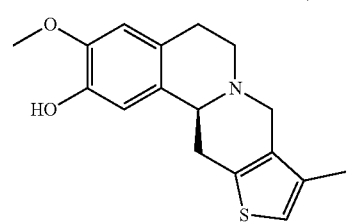
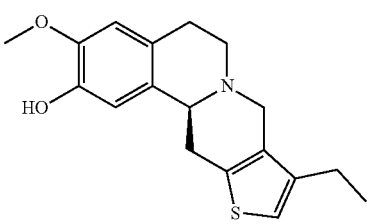
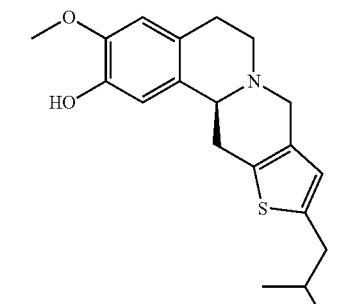
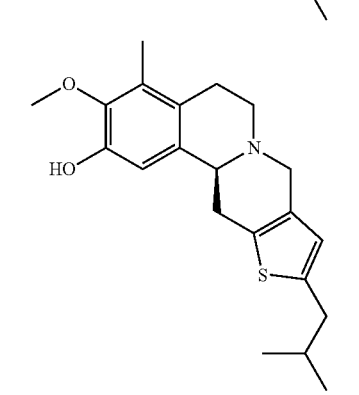
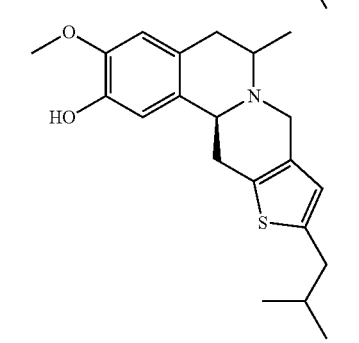
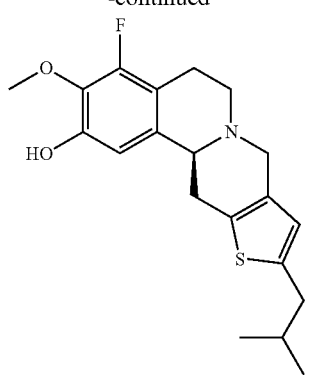
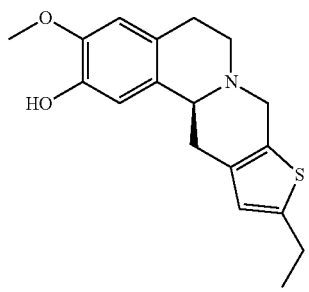
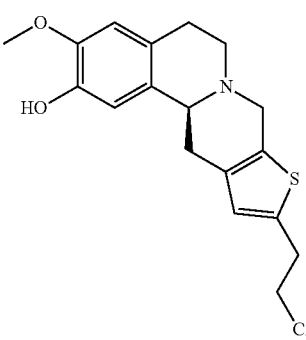
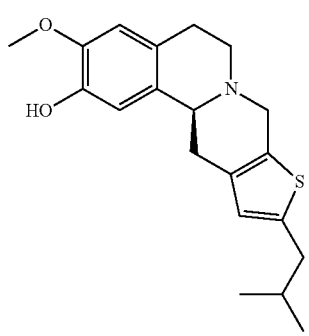
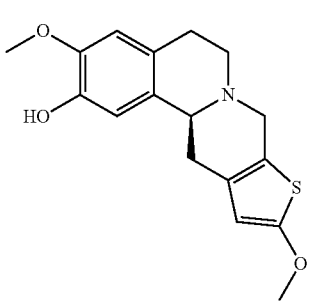

145
-continued
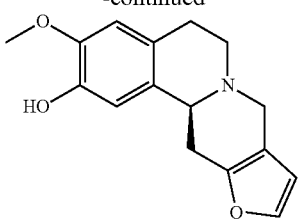
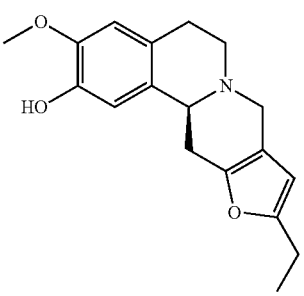
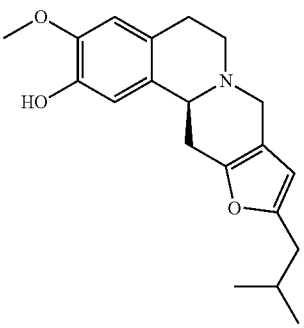
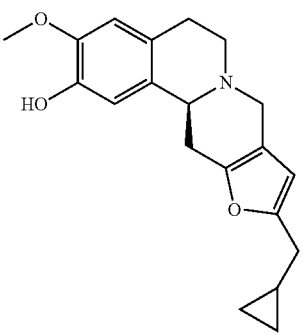
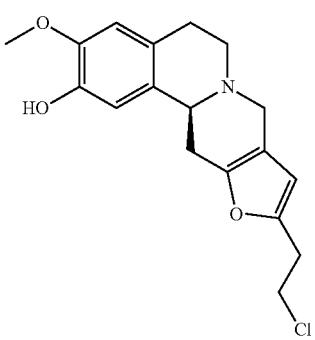
146
-continued
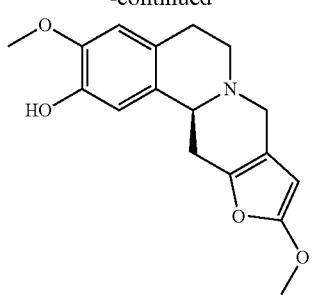
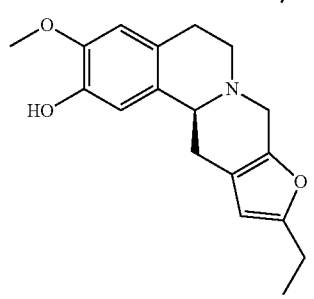
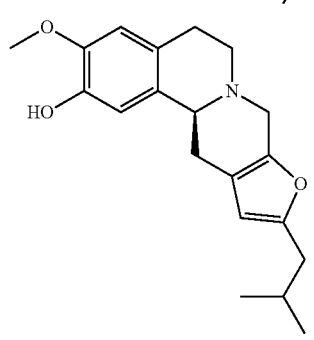
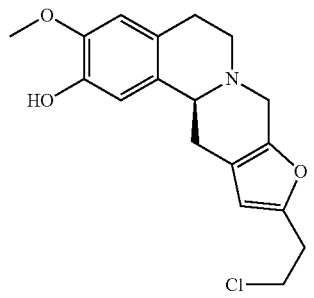
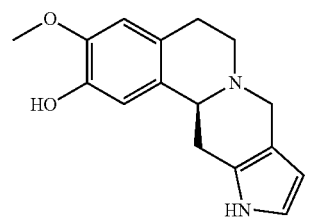
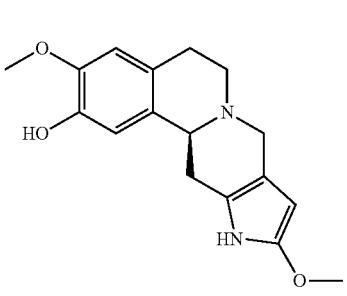

147
-continued
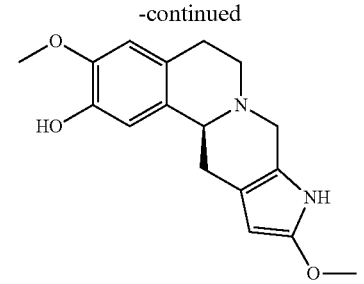
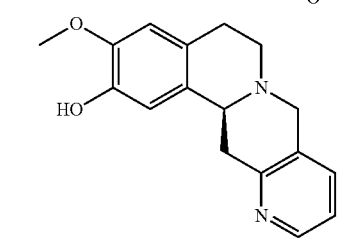
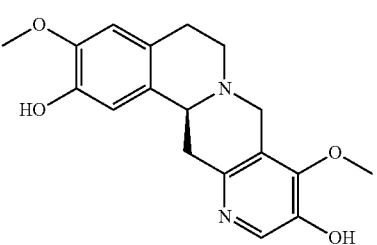
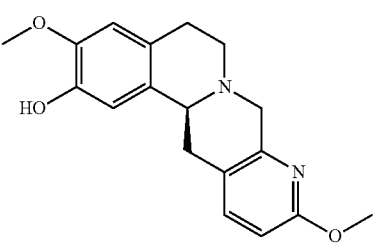
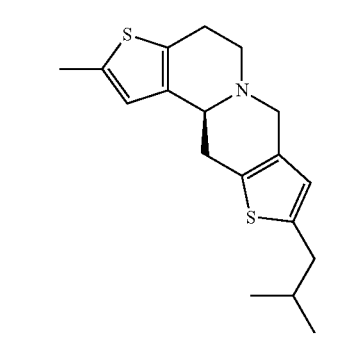
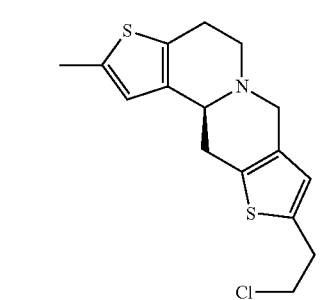
148
-continued
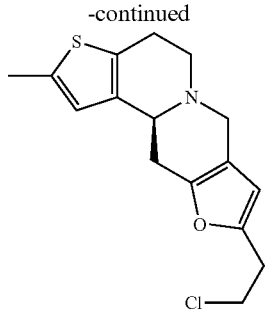
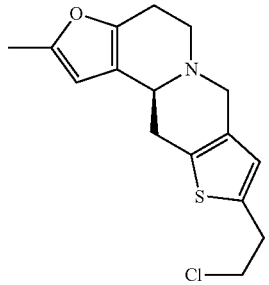
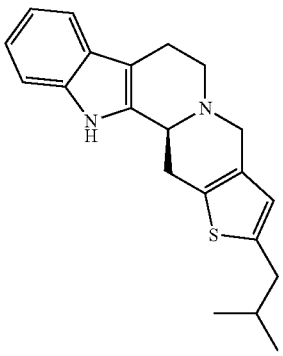
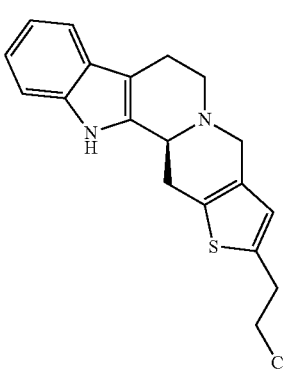
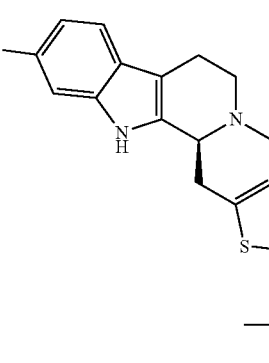

149
-continued
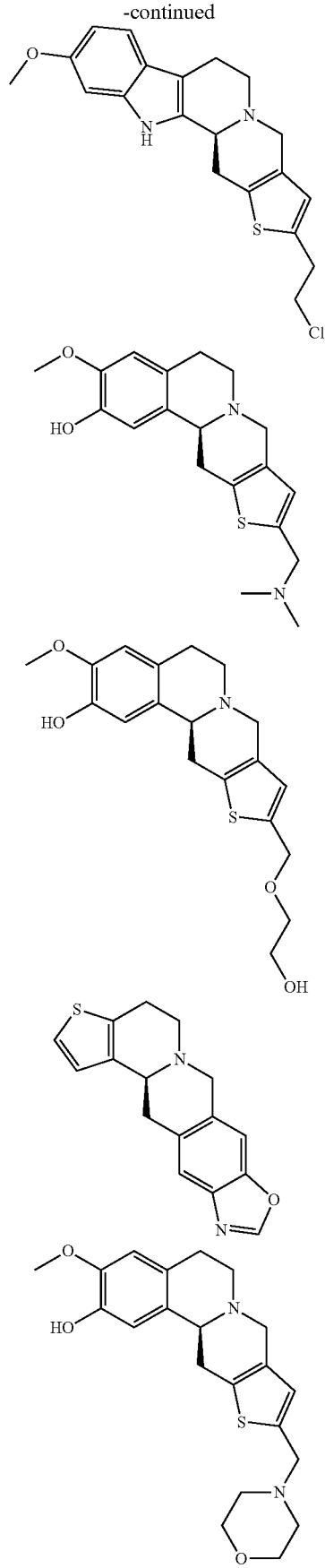
150
-continued
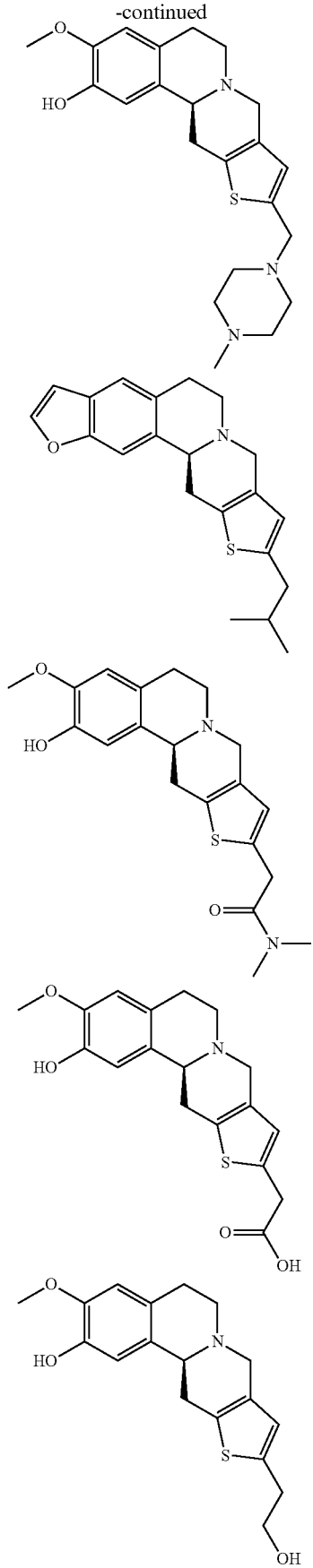

-continued

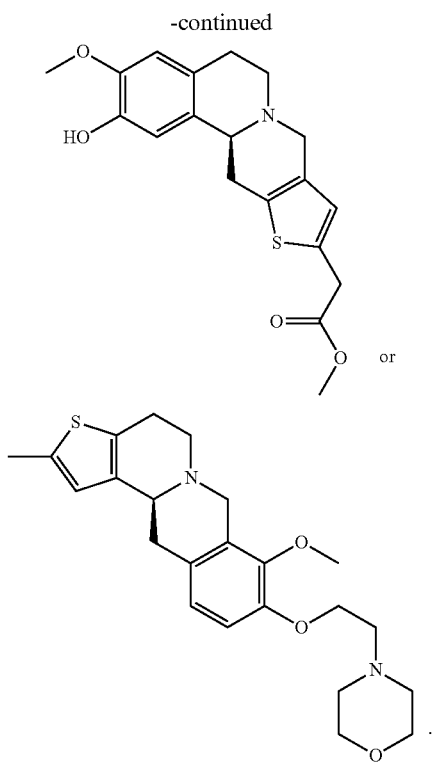

or

3. A process of preparing the diarylo[a,g]quinolizine compound, enantiomer, diastereoisomer, racemate, mixture, pharmaceutically acceptable salt, crystalline hydrate or solvate thereof according to claim 1, wherein the process is carried out as any one of the following methods:

Method A

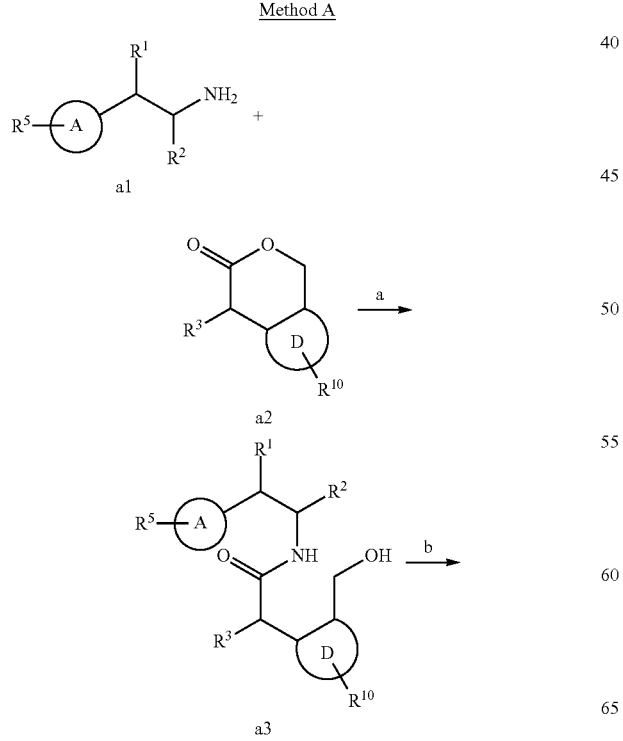

-continued

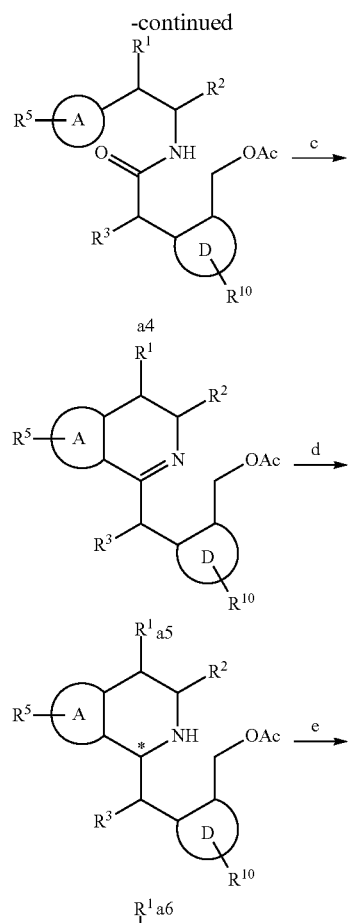

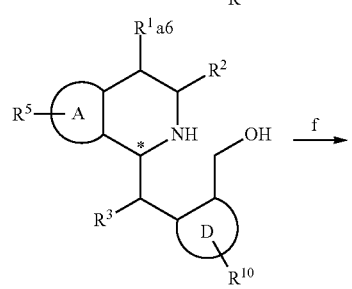

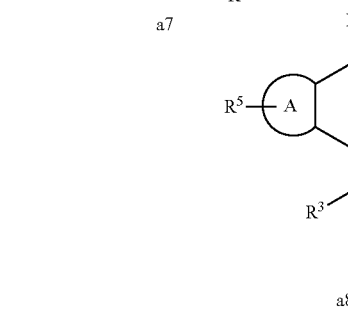

the method A comprises:
a) reacting a1 with a2 through an amino-ester exchange reaction in a polar protic solvent to give a3,
b) reacting a3 with an acylating agent through an acylation reaction in the presence of a base to give a4;
c) dehydrlating and cyclizing a4 in the presence of a condensing agent to give a5;
d) asymmetrically reducing a5 in the presence of a hydrogenation reagent and a chiral catalyst to give a6;
e) hydrolyzing a6 in the presence of a base to give a7;

f) halogenating a7 with a halogenating reagent, and then directly cyclizing it in the presence of a base to give a8;

g) optionally, when a8 has a protective group to be removed, a8 is deprotected to remove the protective group;

Method B:

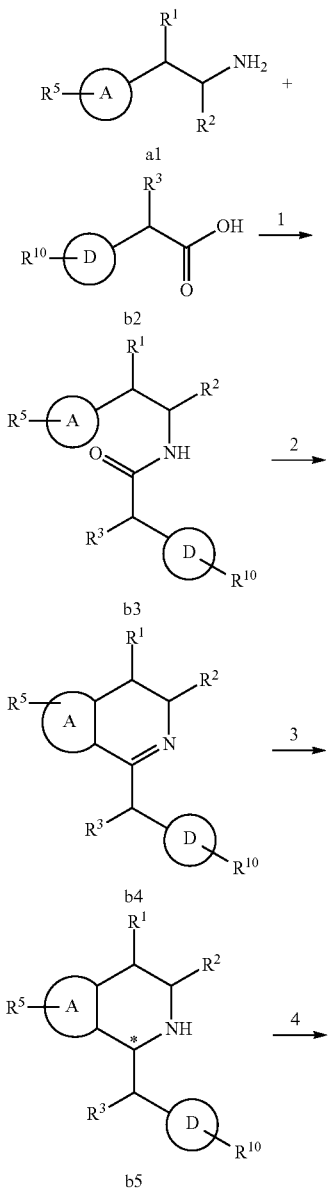

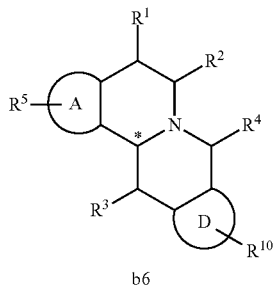

the method B comprises:

1) reacting a1 with b2 by a condensation reaction in the presence of a condensing agent to give b3;

2) dehydrlating and cyclizing b3 in the presence of a condensing agent to give b4;

3) asymmetrically reducing b4 in the presence of a chiral catalyst and a hydrogenation reagent to give b5; and 4) reacting b5 with a substituted aldehyde $R^4$CHO through a Pictet-Spengler reactionunder an acidic condition to give b6;

In the above methods A and B, rings A and D as well as the substituents are defined the same as those in claim 1.

4. A pharmaceutical composition comprising a therapeutically effective amount of one or more selected from the group consisting of the diarylo[a,g]quinolizine compound, enantiomer, diastereoisomer, racemate, mixture, pharmaceutically acceptable salt, crystalline hydrate or solvate thereof according to claim 1, and one or more pharmaceutically acceptable carriers.

5. A method for treating a disease related to dopamine receptors and 5-HT receptors in a subject, wherein the disease related to dopamine receptors and 5-HT receptors is schizophrenia, Parkinson's disease, mania, depression, drug addiction or migraine, comprising:

administering to the subject an effective amount of the diarylo[a,g]quinolizine compound, enantiomer, diastereoisomer, racemate, mixture, pharmaceutically acceptable salt, crystalline hydrate or solvate thereof according to claim 1.

* * * * *

UNITED STATES PATENT AND TRADEMARK OFFICE
CERTIFICATE OF CORRECTION

PATENT NO. : 9,751,882 B2  
APPLICATION NO. : 14/400203  
DATED : September 5, 2017  
INVENTOR(S) : Hong Liu et al.

Page 1 of 1

It is certified that error appears in the above-identified patent and that said Letters Patent is hereby corrected as shown below:

On the Title Page

Item (73), after "Assignee:" please delete "Kingsound & Partner, Beijing (CN)" and insert --Shanghai Institute of Materia Medica, Chinese Academy of Sciences, Pudong, Shanghai (CN)--.

Signed and Sealed this  
Twenty-ninth Day of January, 2019

Andrei Iancu  
*Director of the United States Patent and Trademark Office*